(12) United States Patent
Joo et al.

(10) Patent No.: US 10,177,317 B2
(45) Date of Patent: Jan. 8, 2019

(54) ORGANIC LIGHT EMITTING DISPLAY DEVICE

(71) Applicant: LG Display Co., Ltd., Seoul (KR)

(72) Inventors: Sunghoon Joo, Gyeonggi-do (KR); Hyoseok Kim, Daejeon (KR); Shinhan Kim, Seoul (KR); Seonkeun Yoo, Gyeonggi-do (KR); Min Yun, Gyeonggi-do (KR); Seunghee Yoon, Seoul (KR)

(73) Assignee: LG Display Co., Ltd., Seoul (KR)

( * ) Notice: Subject to any disclaimer, the term of this patent is extended or adjusted under 35 U.S.C. 154(b) by 245 days.

(21) Appl. No.: 15/156,551

(22) Filed: May 17, 2016

(65) Prior Publication Data
US 2017/0155055 A1    Jun. 1, 2017

(30) Foreign Application Priority Data
Nov. 27, 2015    (KR) .................... 10-2015-0167667

(51) Int. Cl.
| | |
|---|---|
| H01L 51/00 | (2006.01) |
| H01L 51/52 | (2006.01) |
| H01L 51/50 | (2006.01) |
| C07D 471/04 | (2006.01) |

(52) U.S. Cl.
CPC ........ H01L 51/0072 (2013.01); C07D 471/04 (2013.01); H01L 51/0054 (2013.01); H01L 51/0058 (2013.01); H01L 51/504 (2013.01); H01L 51/5072 (2013.01); H01L 51/5278 (2013.01); *H01L 51/5044* (2013.01)

(58) Field of Classification Search
CPC ............. H01L 51/0072; H01L 51/0054; H01L 51/0058; H01L 51/504; H01L 51/5072; H01L 51/5278; C07D 471/04
USPC .......................................................... 428/690
See application file for complete search history.

(56) References Cited

U.S. PATENT DOCUMENTS

| | | | |
|---|---|---|---|
| 2014/0061600 A1* | 3/2014 | Kim ................... | H01L 51/0072 257/40 |
| 2015/0162539 A1 | 6/2015 | Lee | |
| 2016/0197289 A1* | 7/2016 | Sado .................... | C07D 405/14 257/40 |

FOREIGN PATENT DOCUMENTS

| | | | |
|---|---|---|---|
| EP | 2 927 978 A1 | | 10/2015 |
| JP | WO 2014/097711 | * | 6/2014 |
| WO | 2014/097711 A1 | | 6/2014 |

OTHER PUBLICATIONS

Extended European Search Report dated Apr. 28, 2017 for corresponding European Patent Application No. 16168879.1.

* cited by examiner

*Primary Examiner* — Jayne L Mershon
(74) *Attorney, Agent, or Firm* — Morgan, Lewis & Bockius LLP

(57) ABSTRACT

An organic light emitting display device is provided. The organic light emitting display device includes at least two or more light emitting parts each having a light emitting layer and an electron transport layer; and a charge generation layer between the at least two or more light emitting parts. The charge generation layer comprises a compound that includes a core with two nitrogen atoms and a functional group having crystallinity.

7 Claims, 12 Drawing Sheets

ORGANIC LIGHT EMITTING DISPLAY DEVICE

This application claims the priority benefit of Korean Patent Application No. 10-2015-0167667 filed on Nov. 27, 2015, which is hereby incorporated herein by reference for all purposes as if fully set forth herein.

BACKGROUND

Field

The present disclosure relates to an organic light emitting display device, and more particularly, to an organic light emitting display device with improved operating voltage, light emission efficiency, external quantum efficiency, and lifetime characteristics.

Discussion of the Related Art

Image displays used for displaying a variety of information on the screen are one of the core technologies of the information and communication era. Such image displays have been developed to be thinner, lighter, and more portable, and furthermore to have high performance. With the development of the information society, various demands for display devices are on the rise. To meet these demands, research on panel displays such as liquid crystal displays (LCD), plasma display panels (PDP), electroluminescent displays (ELD), field emission displays (FED), organic light emitting diodes (OLED), etc is actively under way.

Among these types of flat panel displays, the OLED devices are advantageous in that they can be fabricated on a flexible substrate such as plastic, operate at a low voltage of 10 V or less, have lower power consumption, and deliver vivid color reproduction, as compared with plasma display panels or inorganic light emitting displays. Especially, white OLED devices are used for various purposes in lighting, thin light sources, backlights for liquid crystal displays, or full-color displays employing color filters.

In the development of white OLED devices, high efficiency, long lifetime, color purity, color stability against current and voltage variations, ease of manufacture, etc are important, so research and development are being done depending on which of these features should be taken into account. White OLED device structures may be roughly classified into a single-layer emitting structure and a multilayer emitting structure. Of these structures, the multilayer emitting structure having a blue fluorescent emitting layer and a yellow phosphorescent emitting layer stacked in tandem is mainly employed to realize white OLED devices with long lifetime.

Specifically, a stack structure of first and second light emitting parts is used, with the first light emitting part using a blue fluorescent diode as a light emitting layer, and the second light emitting part using a yellow phosphorescent diode as a light emitting layer. Such a white OLED device produces white light by mixing blue light emitted from the blue fluorescent diode and yellow light emitted from the yellow phosphorescent diode. A charge generation layer is formed between the first light emitting part and the second light emitting part to double the efficiency of current generated in the light emitting layers and facilitate charge distribution. The charge generation layer is a layer that generates a charge, i.e., electrons and holes, in it. The charge generation layer can prevent a rise in operating voltage because it doubles the efficiency of current generated in the light emitting layers and facilitates charge distribution.

However, the charge generation layer has a PN junction structure consisting of an N-type charge generation layer and a P-type charge generation layer. The difference in energy level between the P-type charge generation layer and the N-type charge generation layer deteriorates the property of injecting electrons generated at the interface between the P-type charge generation layer and an adjacent injection transport layer into the N-type charge generation layer. Also, if the N-type charge generation layer is doped with a dopant such as an alkali metal, the dopant is diffused into the P-type charge generation layer, thus leading to a decrease in the lifetime of the device.

SUMMARY

Accordingly, the present disclosure is directed to an organic light emitting display device that substantially obviates one or more of the problems due to limitations and disadvantages of the related art.

An object of the present disclosure is to provide an organic light emitting display device with improved operating voltage, light emission efficiency, external quantum efficiency, and lifetime characteristics.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the disclosure, as embodied and broadly described, an organic light emitting display device comprises at least two or more light emitting parts each comprising a light emitting layer and an electron transport layer; and a charge generation layer between the at least two or more light emitting parts, wherein the charge generation layer comprises a compound that includes a core with two nitrogen atoms and a functional group having crystallinity.

The charge generation layer comprises a P-type charge generation layer and an N-type charge generation layer, and the compound is included in the N-type charge generation layer.

The N-type charge generation layer further comprises a dopant, and the dopant includes one among an alkali metal, an alkali earth metal, an alkali metal compound, an alkali earth metal compound, an organic complex of alkali metals, or an organic complex of alkali earth metals.

The nitrogen atoms included in the core of the compound bind to the dopant to prevent the dopant from being diffused into another layer adjacent to the charge generation layer.

The core comprises triphenylene.

The functional group comprises phenanthroline.

One of the at least two or more light emitting parts comprises a blue light emitting part, and the another one of the at least two or more light emitting parts is a yellow-green light emitting part.

The compound is represented by the following Chemical Formula 1:

[Chemical Formula 1]

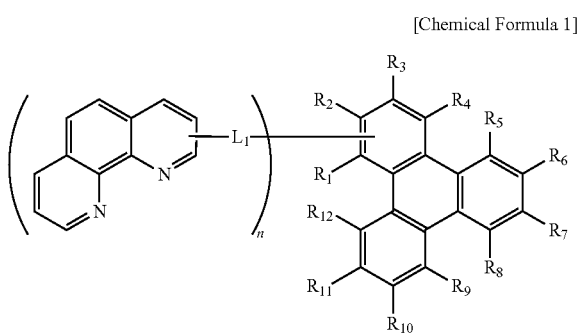

wherein $L_1$ includes one among a substituted or unsubstituted arylene group with 6 to 60 carbon atoms, a substituted or unsubstituted heteroarylene group with 3 to 60 carbon atoms, and a single bond, one among $R_1$ to $R_{12}$ binds to $L_1$, and the others among $R_1$ to $R_{12}$ that do not bind to $L_1$ include independently one among a substituted or unsubstituted aryl group with 5 to 30 carbon atoms, a substituted or unsubstituted heteroaryl group with 4 to 30 carbon atoms, a halogen group, a nitrile group, heavy hydrogen, and hydrogen, and n includes one among 1 and 2.

The compound represented by Chemical Formula 1 includes one among the following compounds:

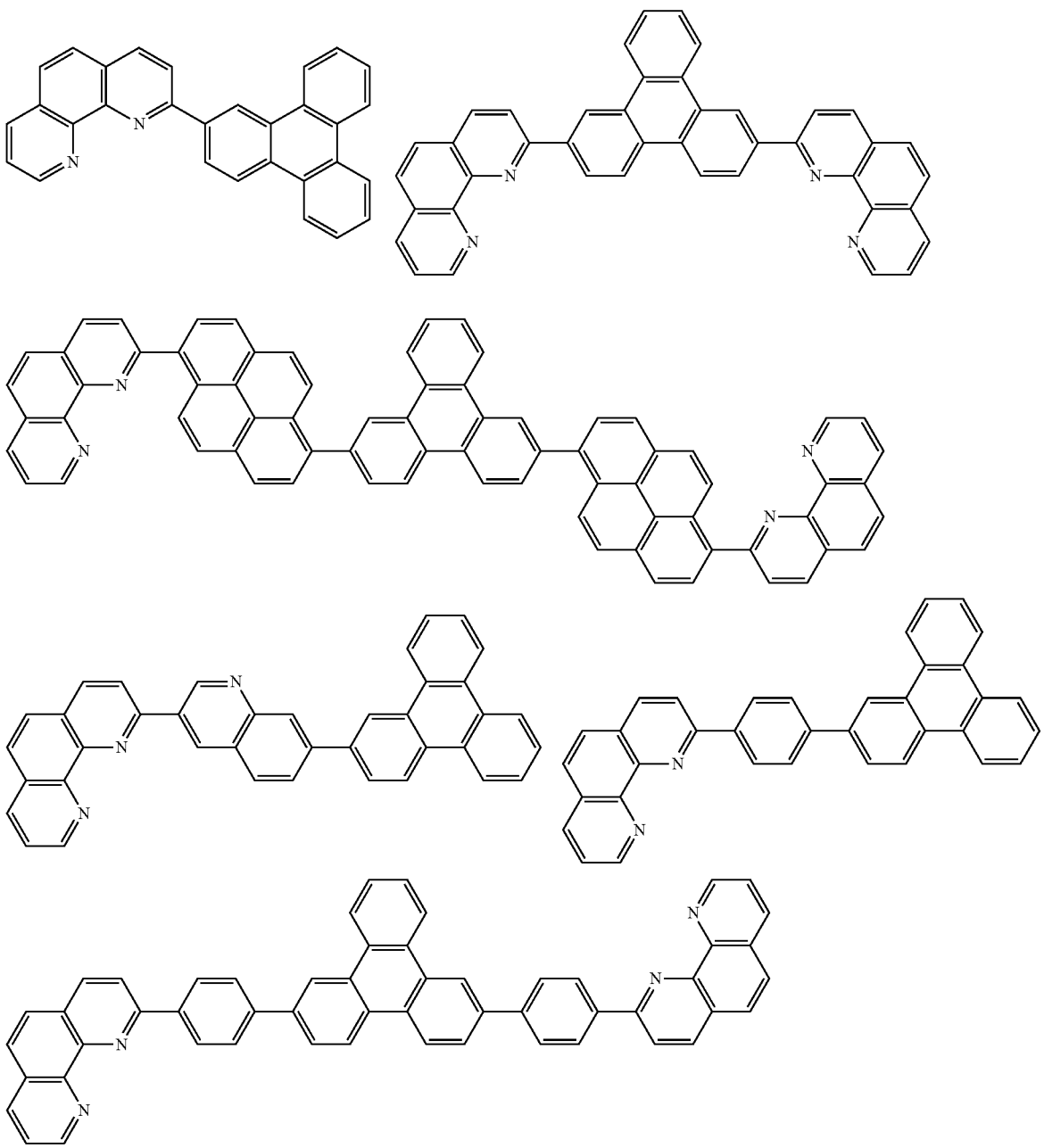

-continued
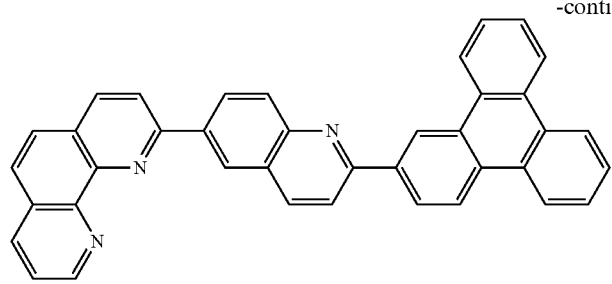
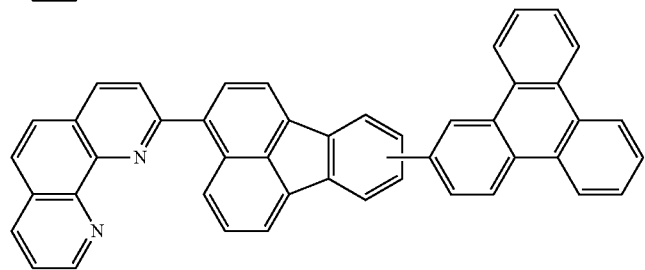
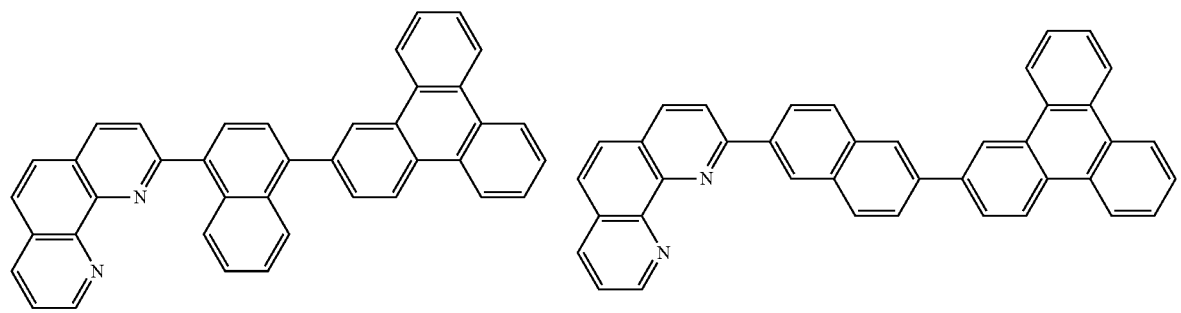
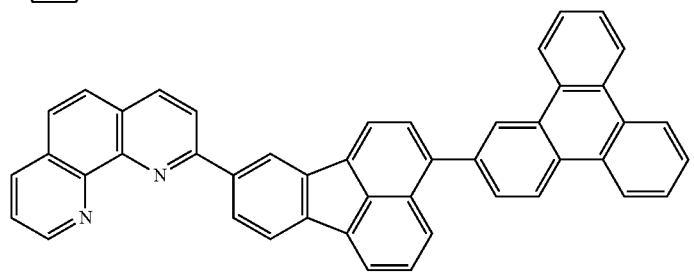
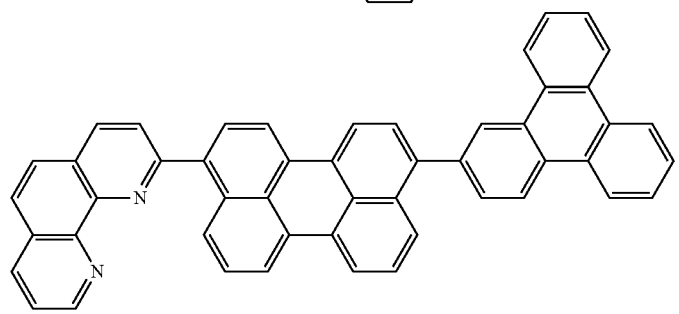
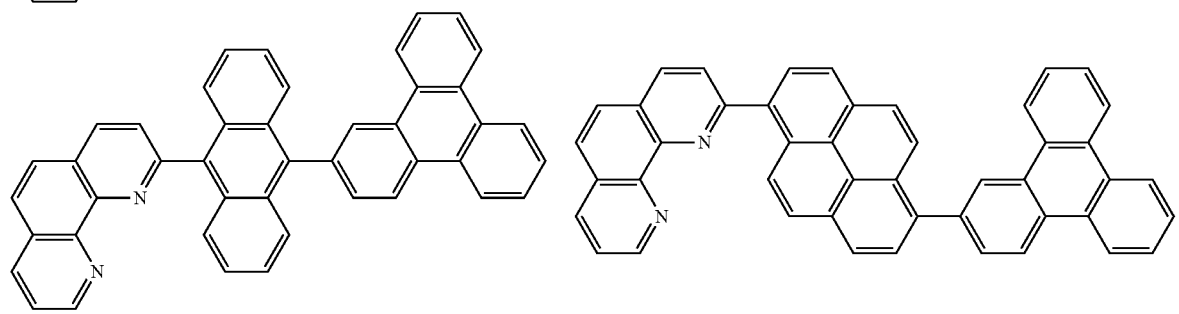

-continued
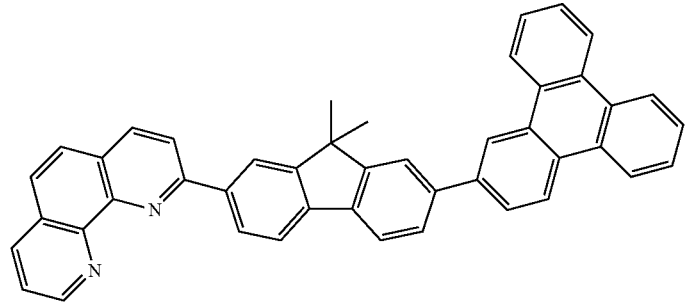
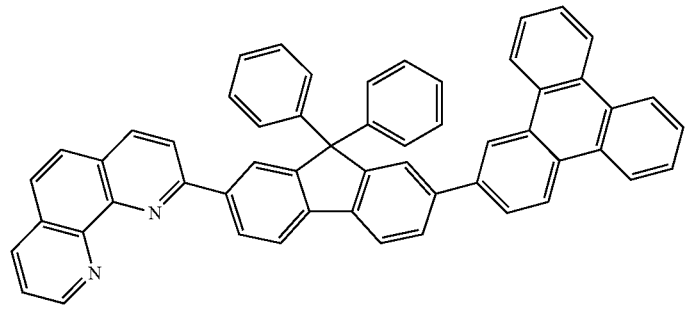
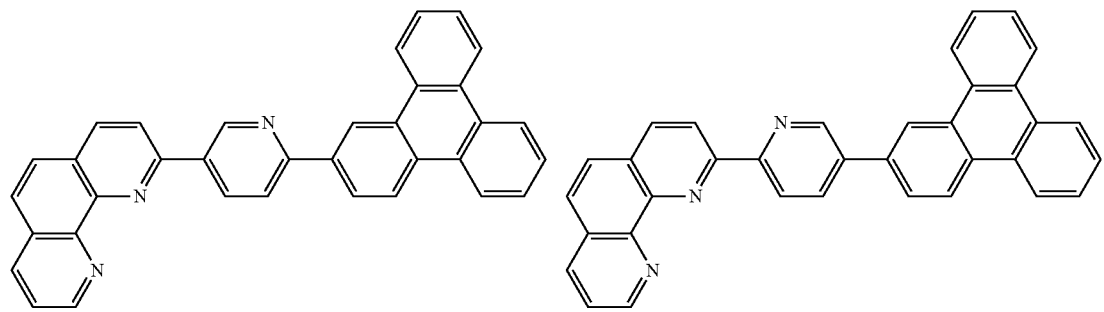
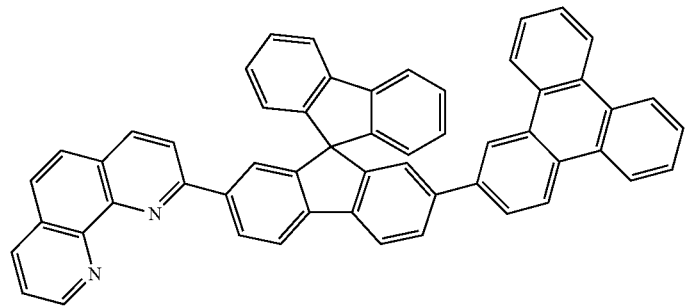
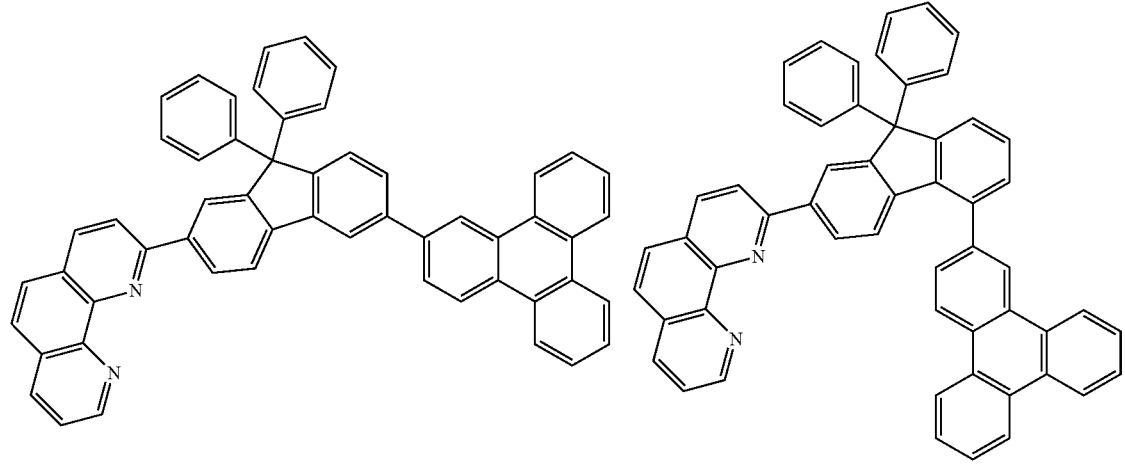

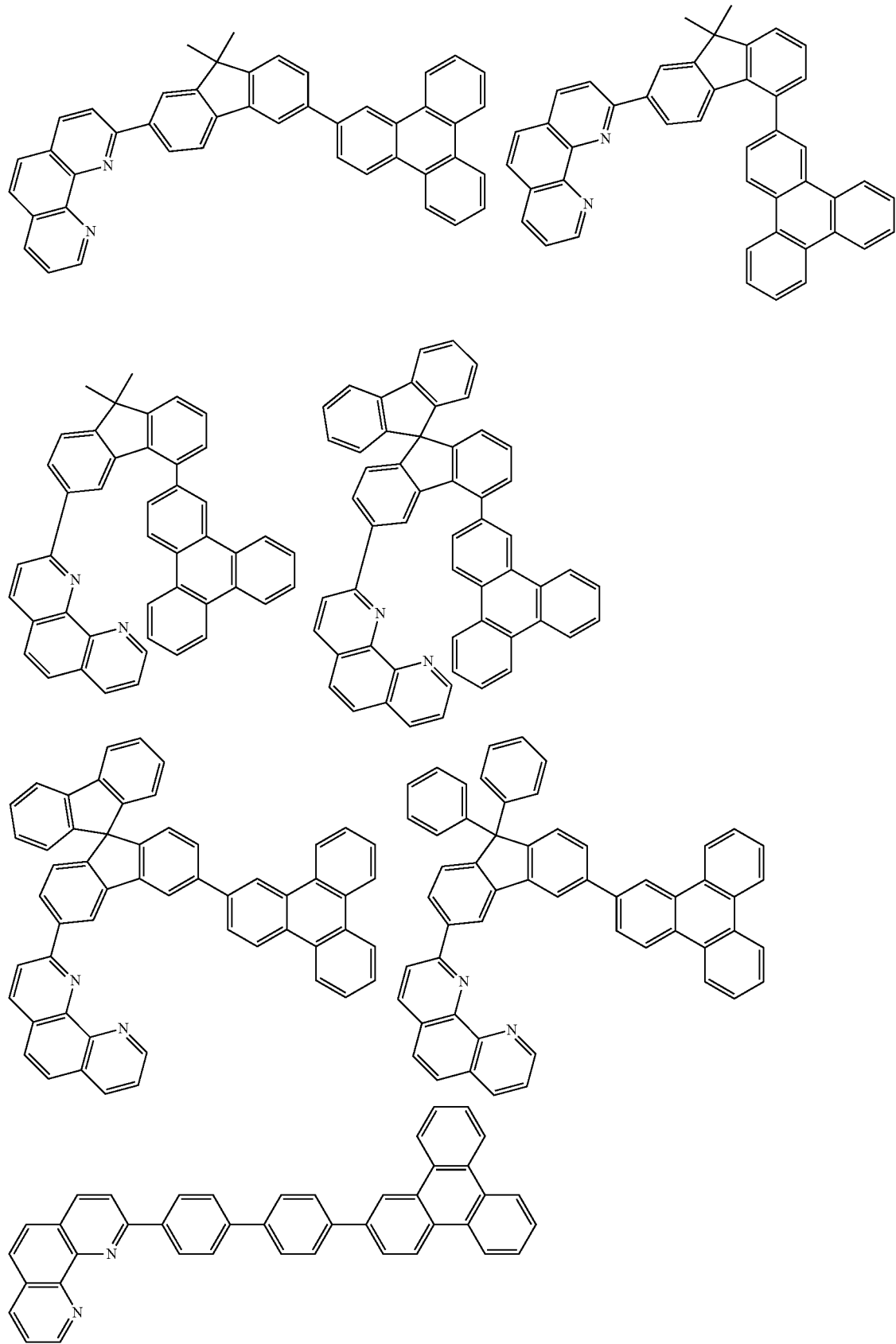

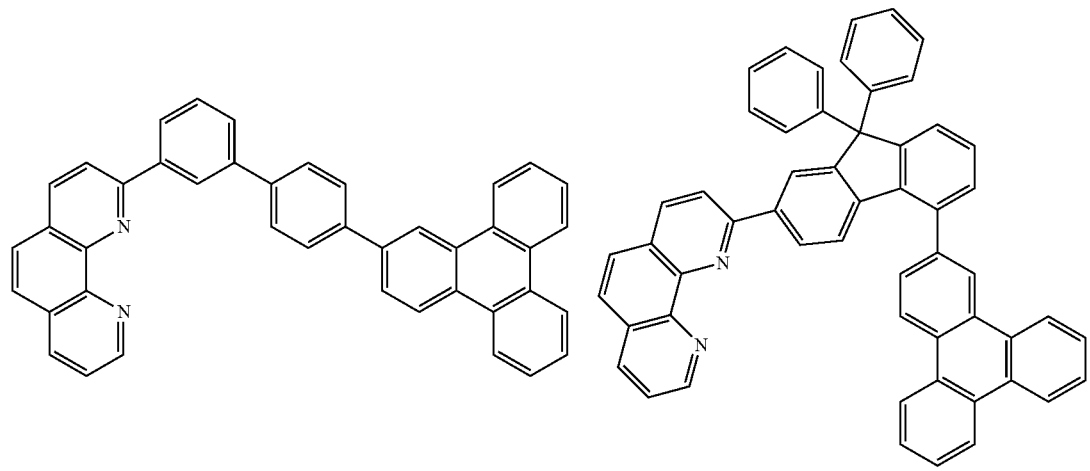
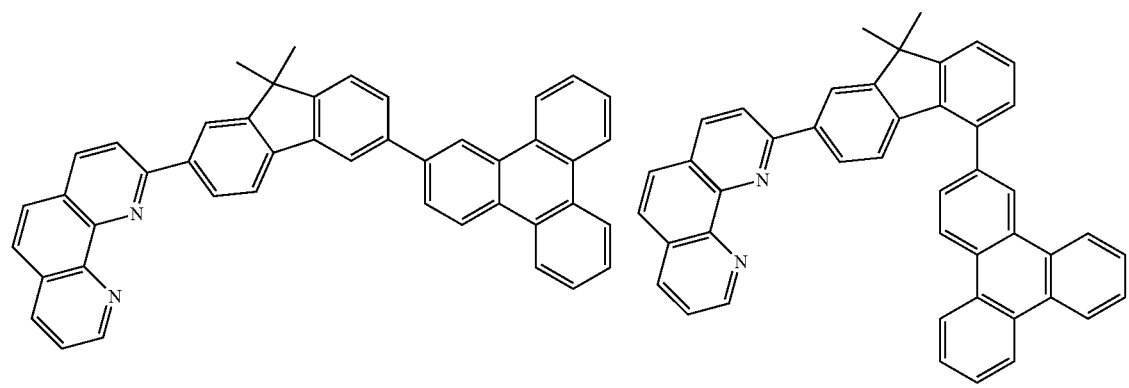
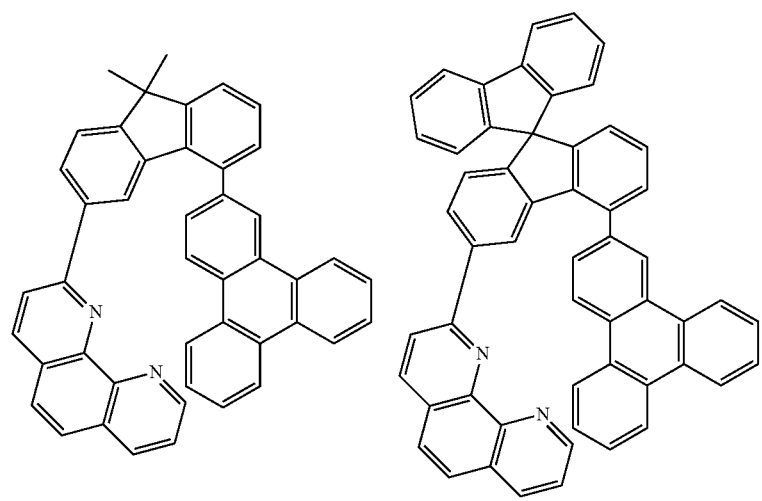

-continued
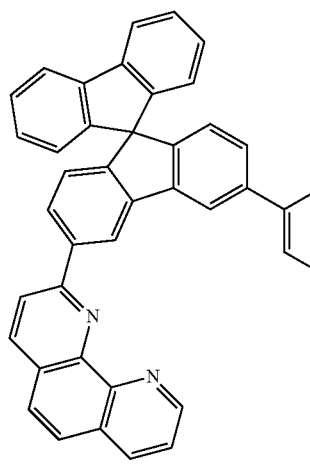
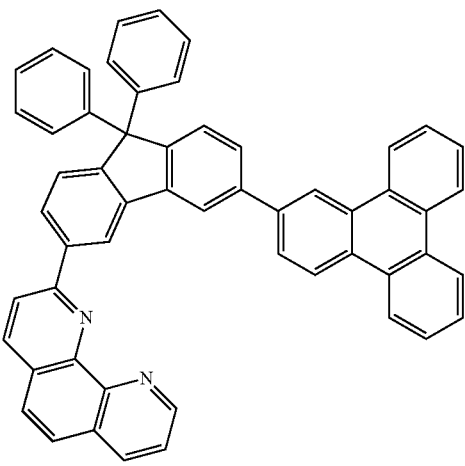
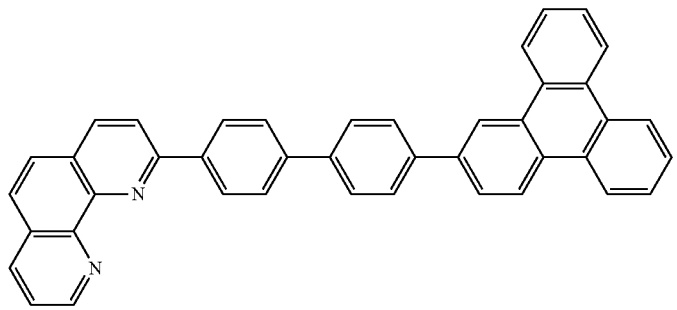
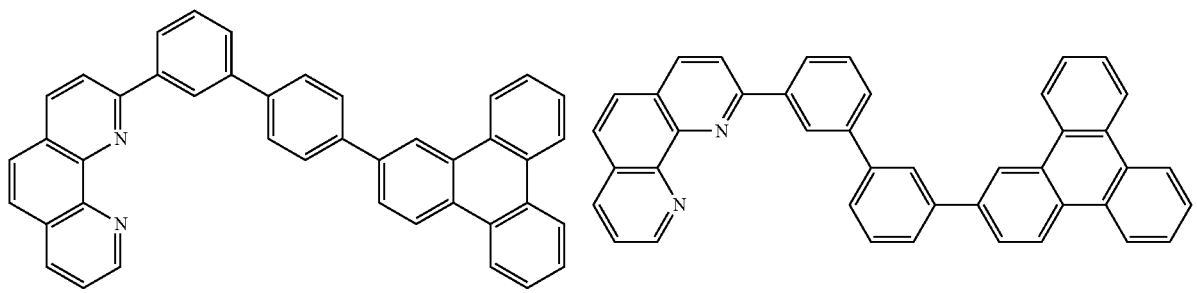
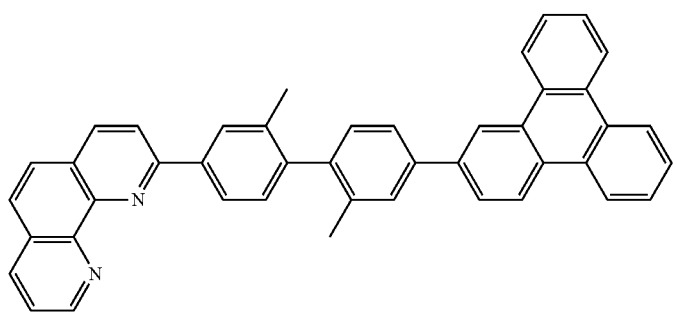
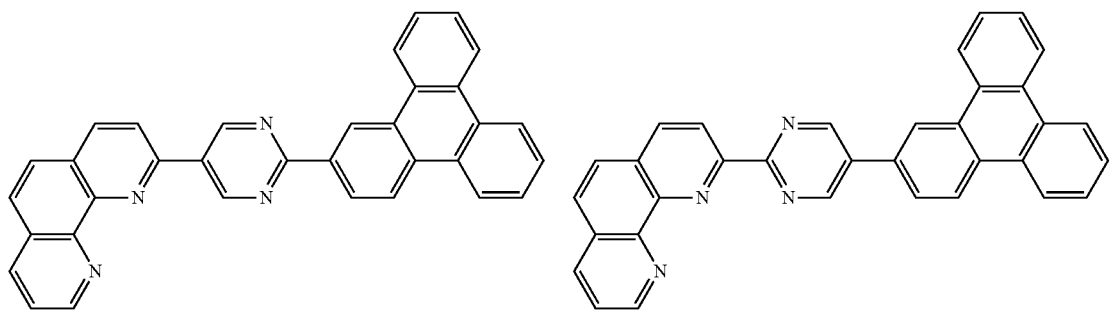

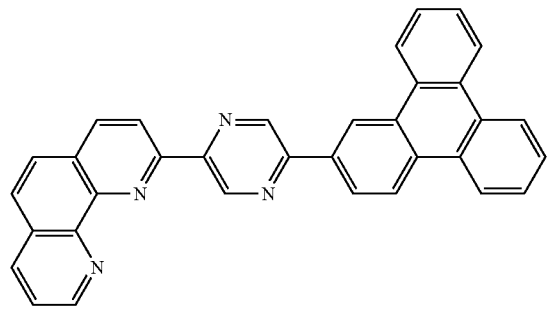
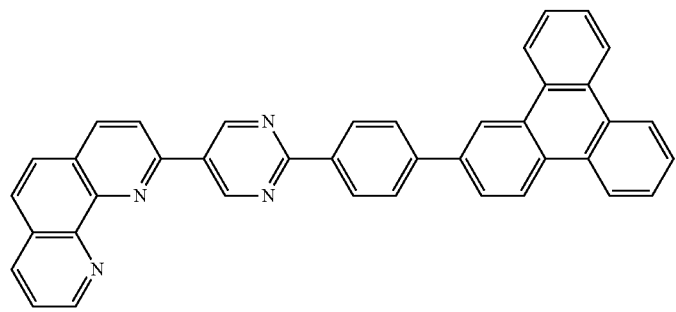
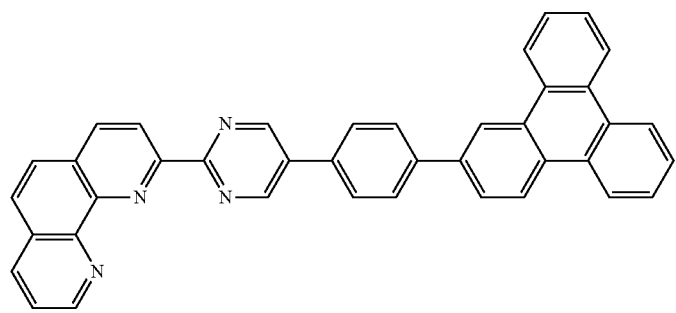
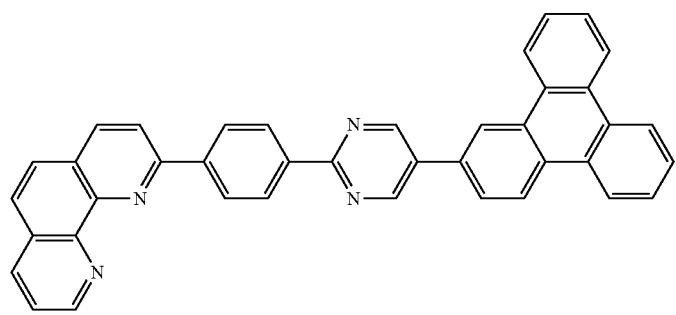
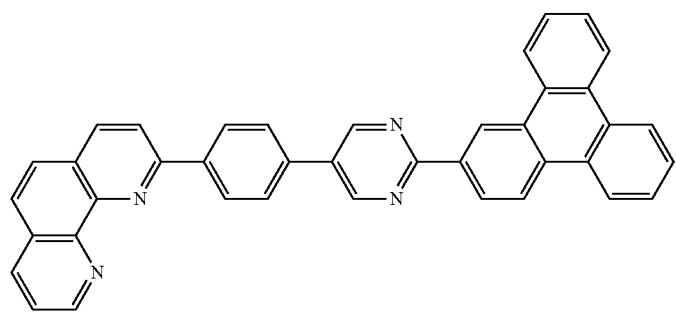

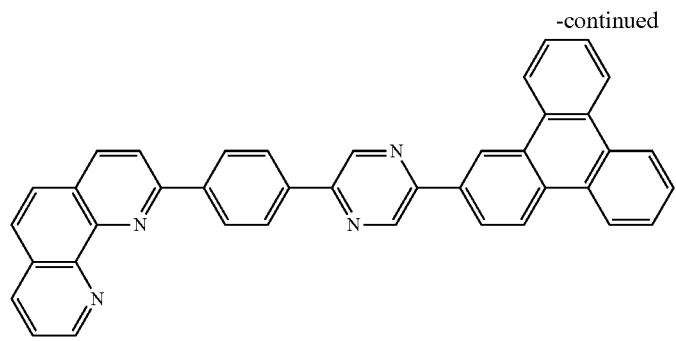
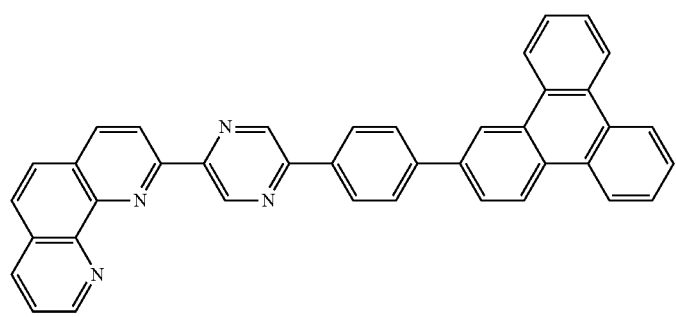
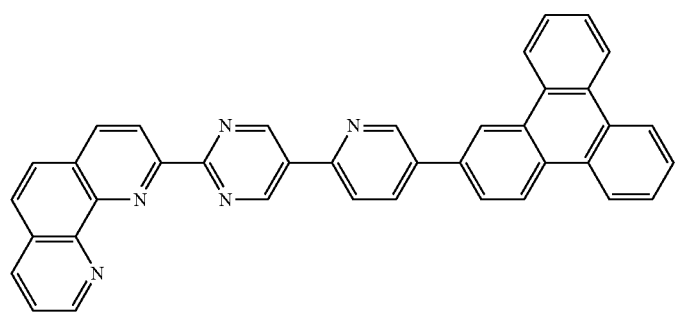
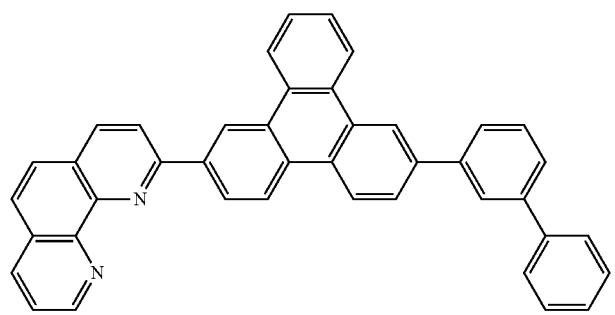
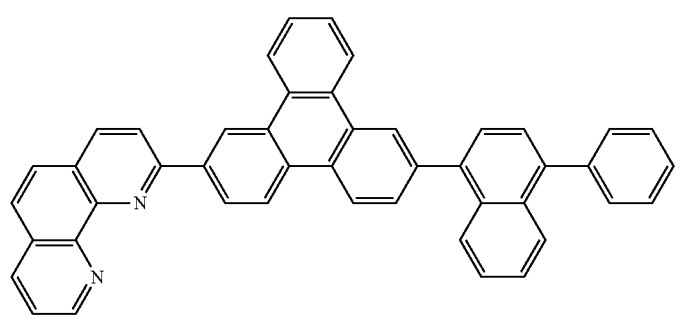

-continued
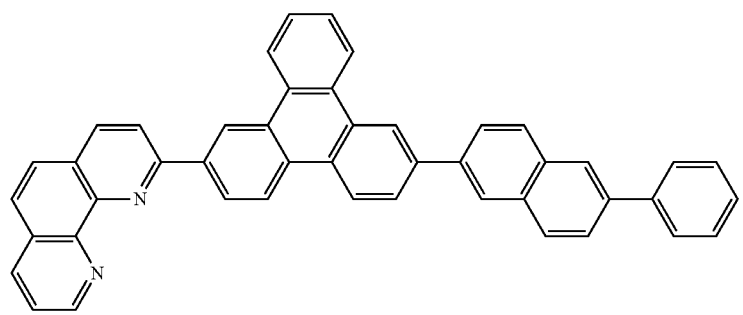
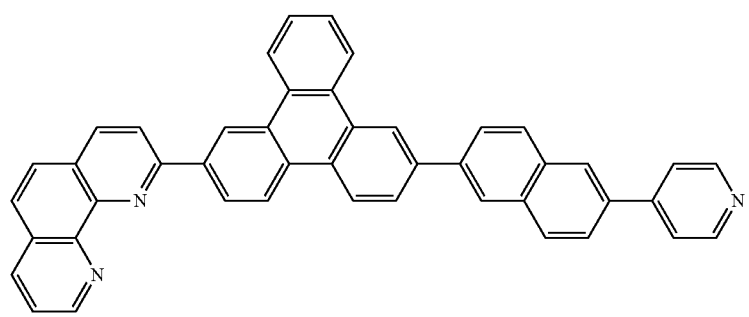
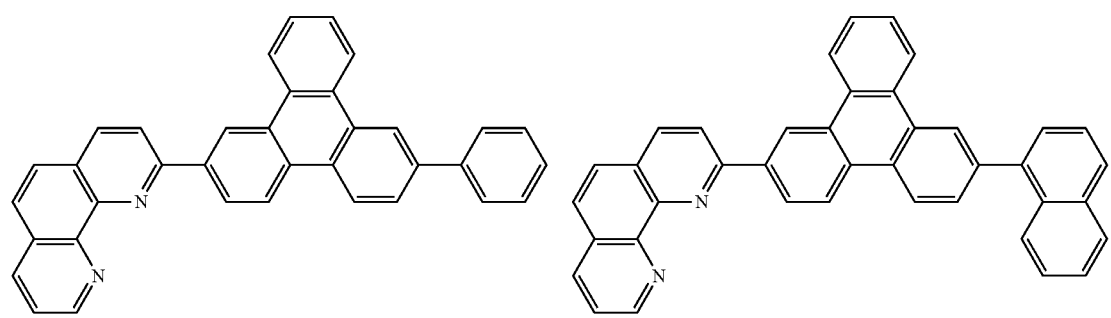
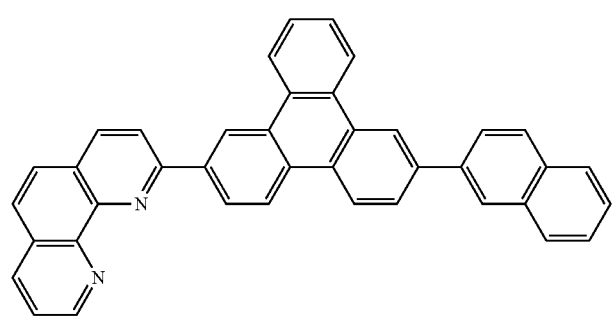
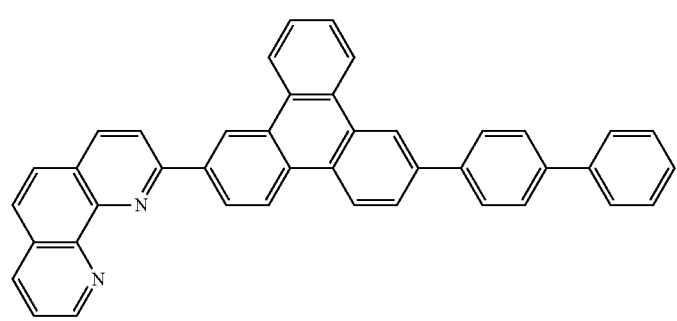

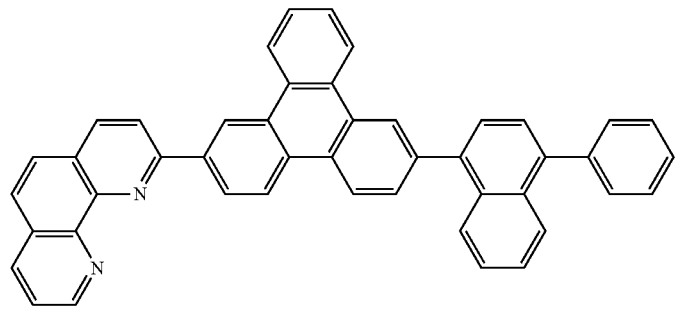
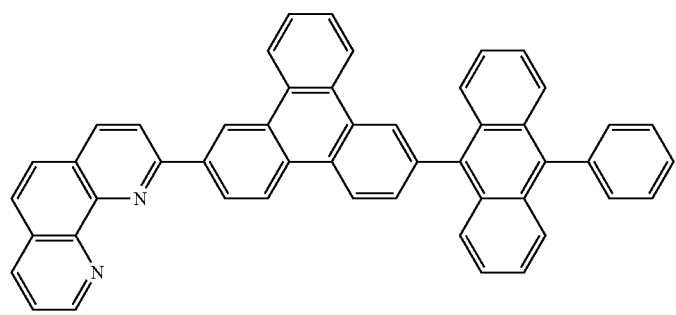
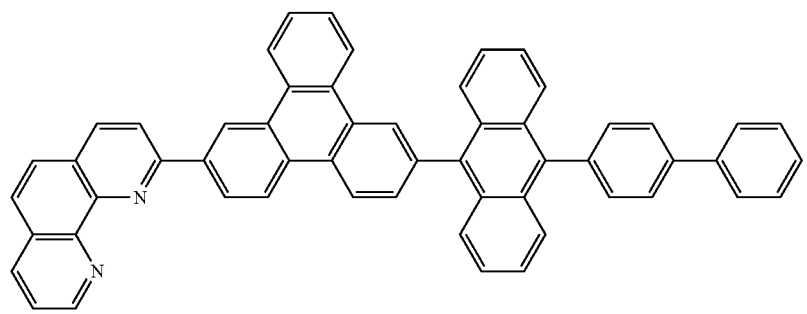
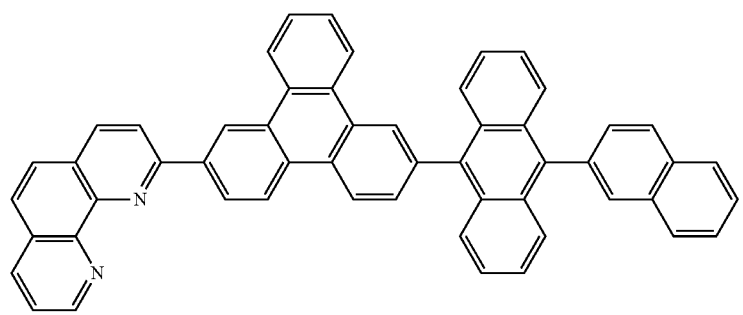
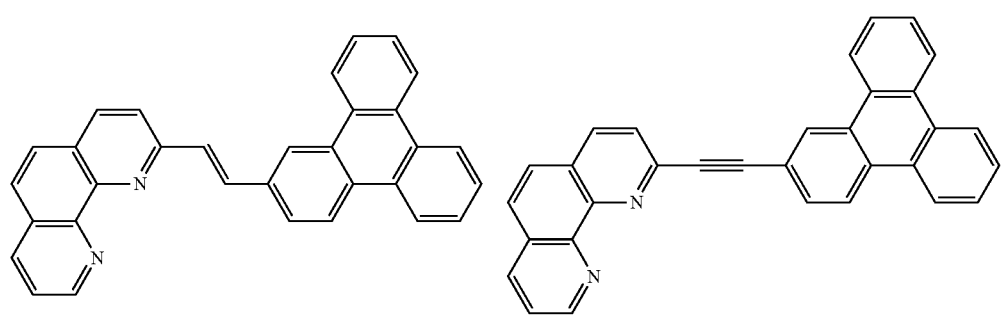

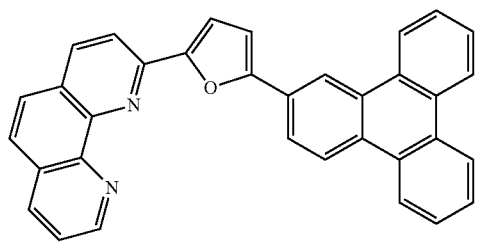
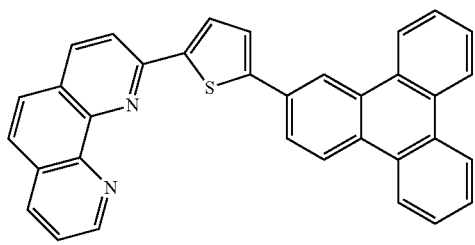
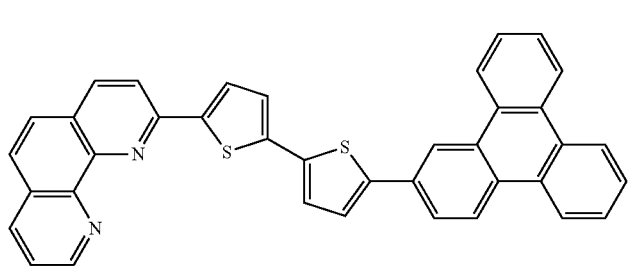
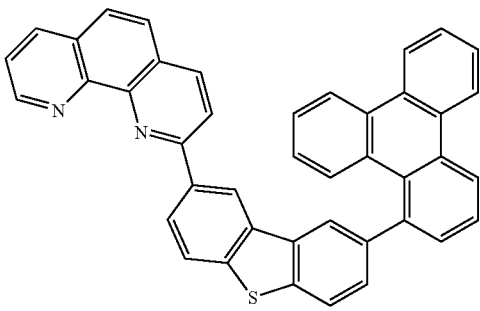
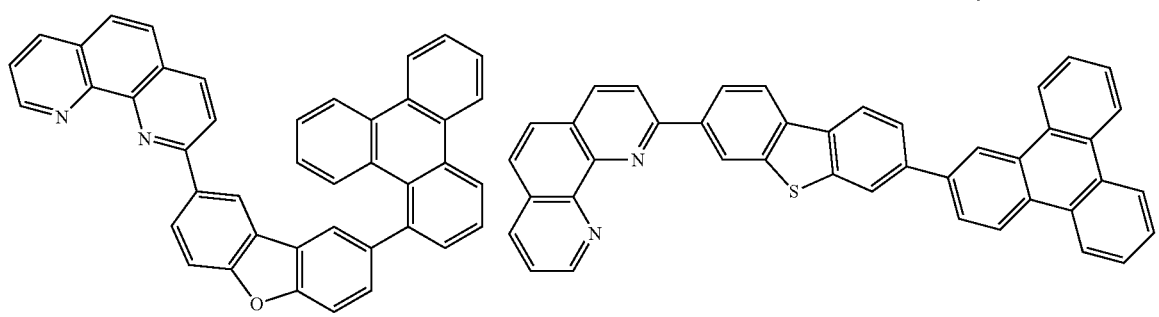
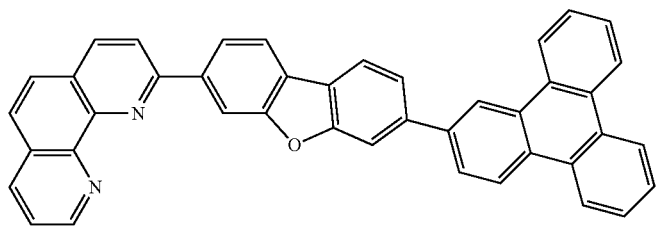
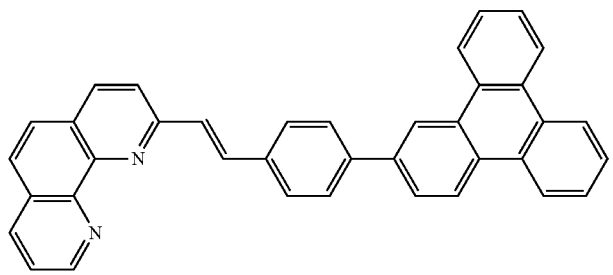
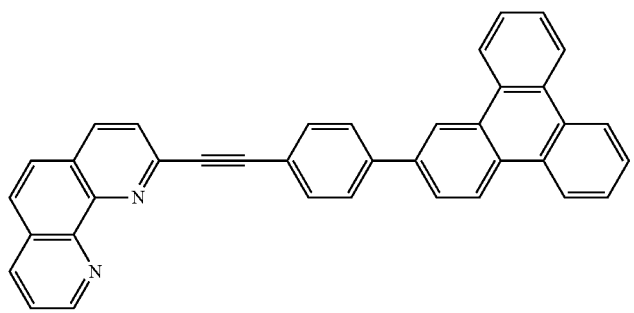

-continued
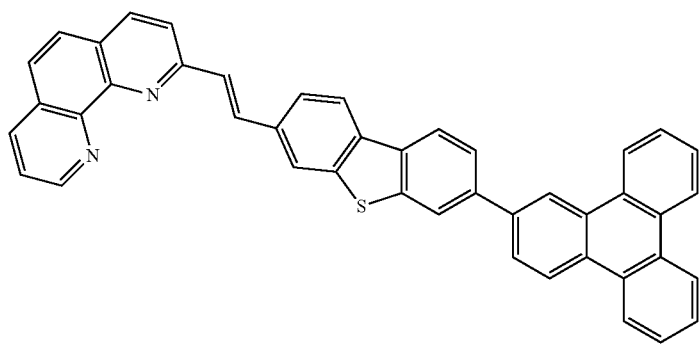
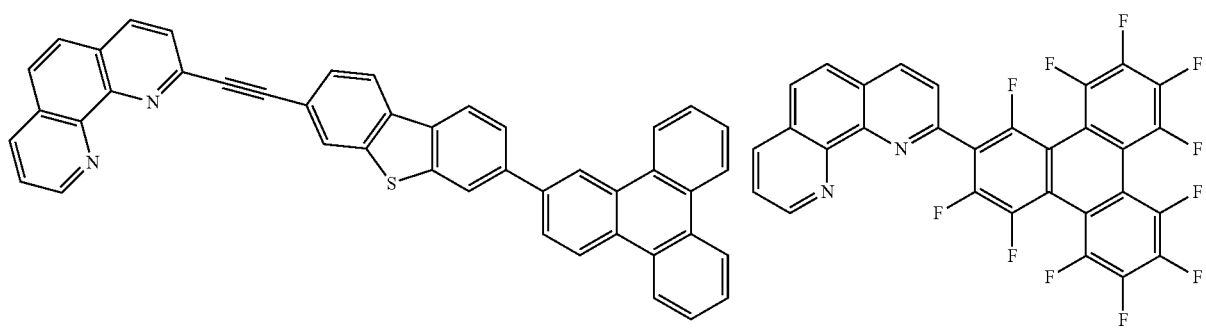
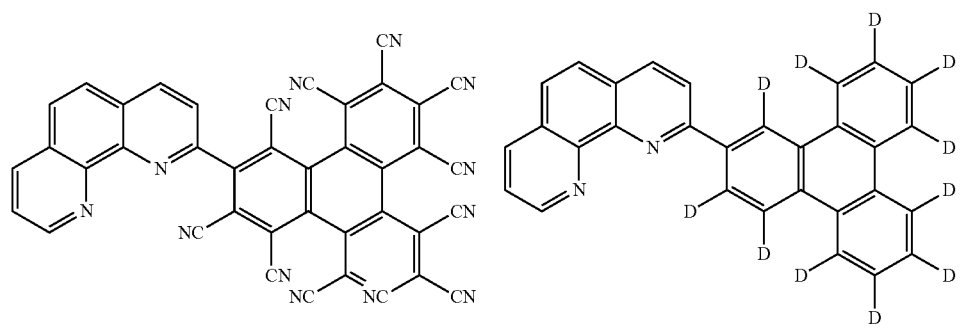
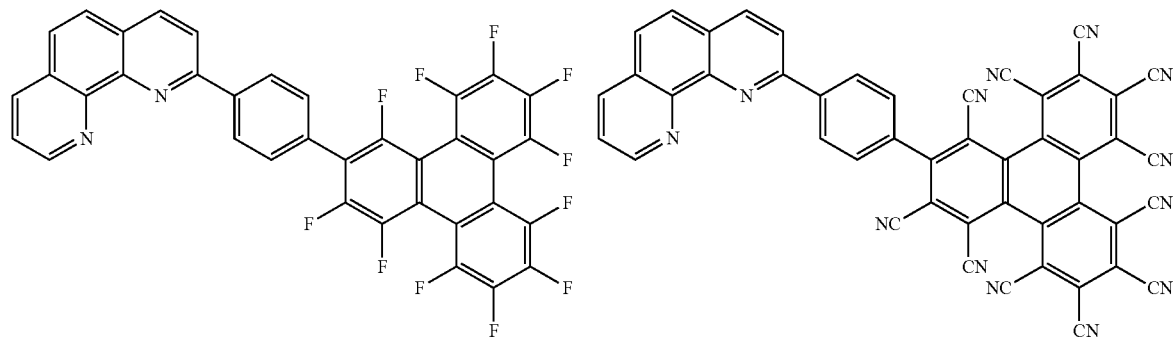
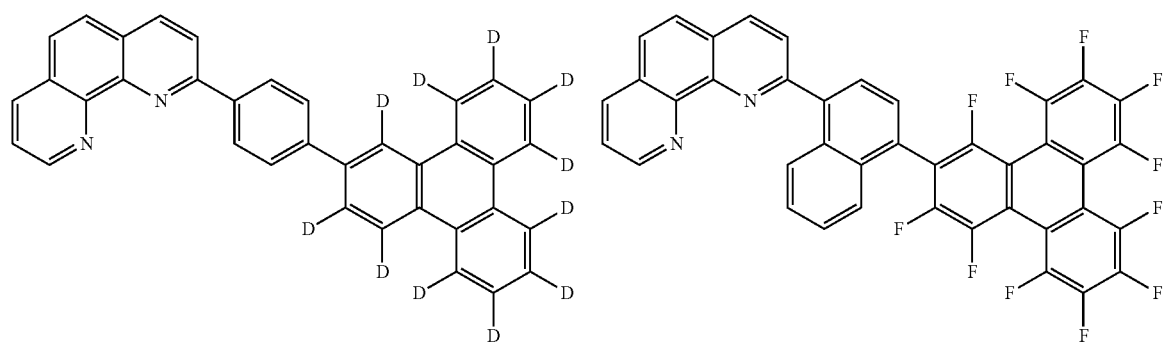

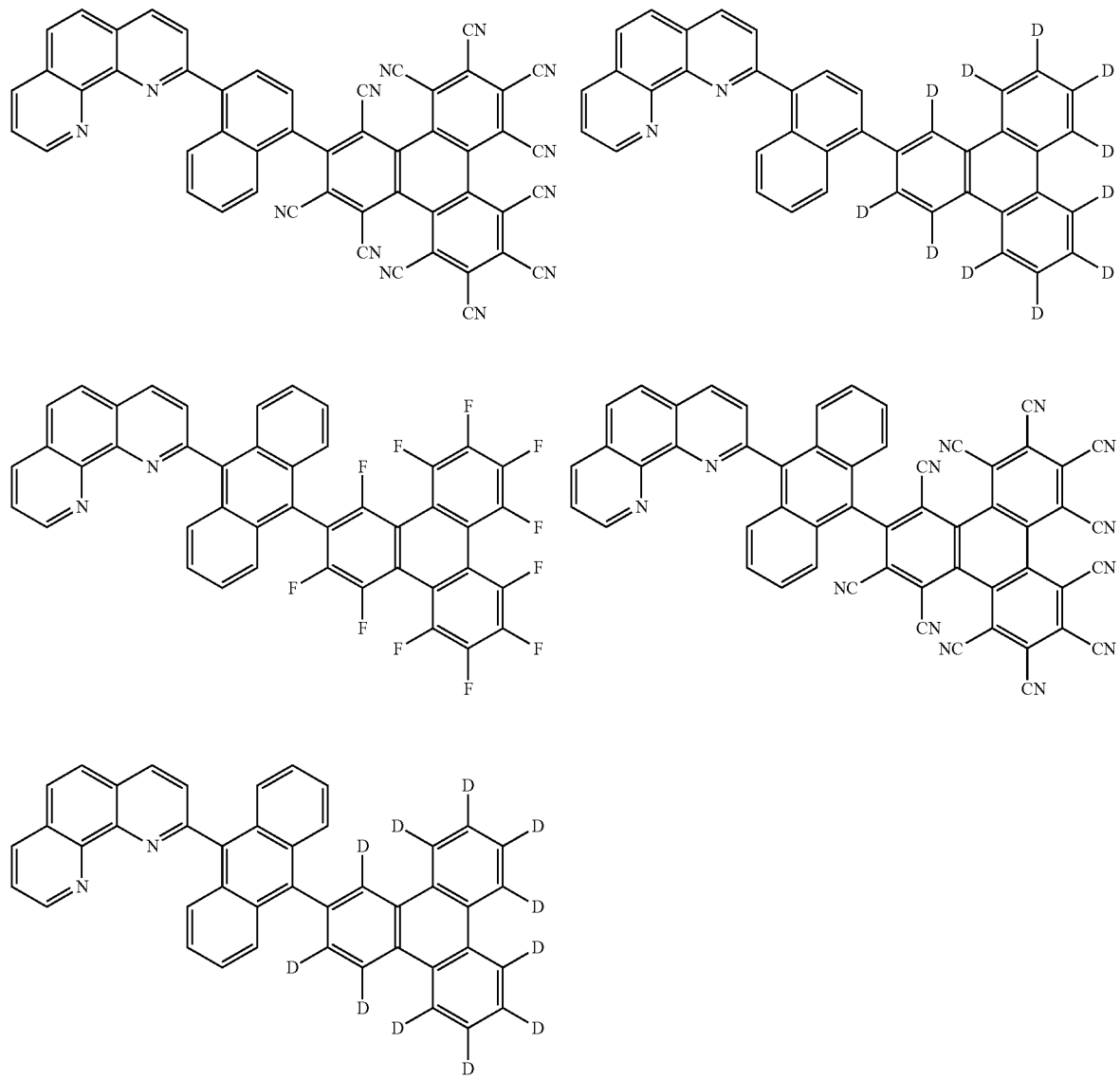

In another aspect, an organic light emitting display device comprises at least two or more light emitting parts each comprising a light emitting layer and an electron transport layer; and a charge generation layer between the at least two or more light emitting parts, wherein the charge generation layer comprises a compound represented by the following Chemical Formula 1:

[Chemical Formula 1]

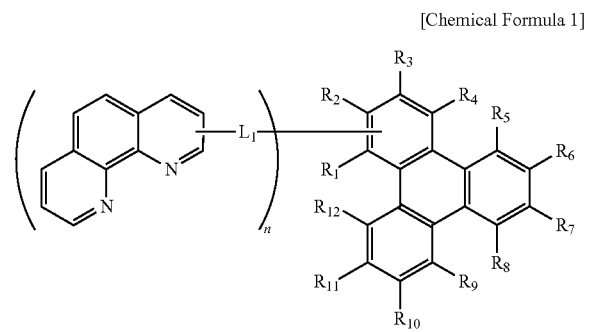

wherein $L_1$ includes one among a substituted or unsubstituted arylene group with 6 to 60 carbon atoms, a substituted or unsubstituted heteroarylene group with 3 to 60 carbon atoms, and a single bond, one among $R_1$ to $R_{12}$ binds to $L_1$, and the others among $R_1$ to $R_{12}$ that do not bind to $L_1$ include independently one among a substituted or unsubstituted aryl group with 5 to 30 carbon atoms, a substituted or unsubstituted heteroaryl group with 4 to 30 carbon atoms, a halogen group, a nitrile group, heavy hydrogen, and hydrogen, and n includes one among 1 and 2.

The compound represented by Chemical Formula 1 includes one among the following compounds:

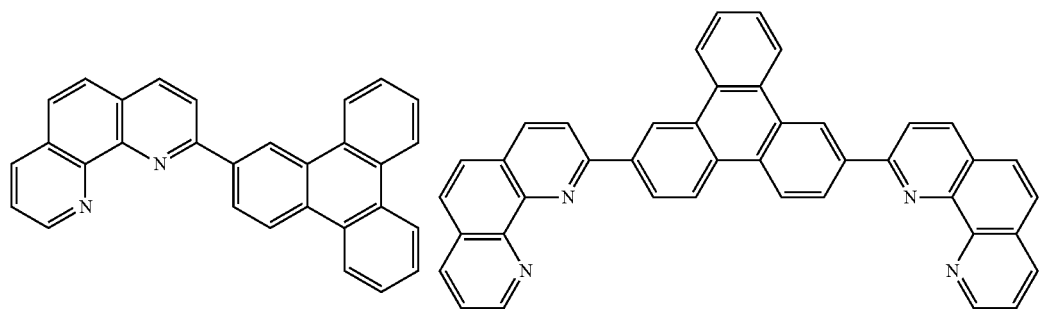
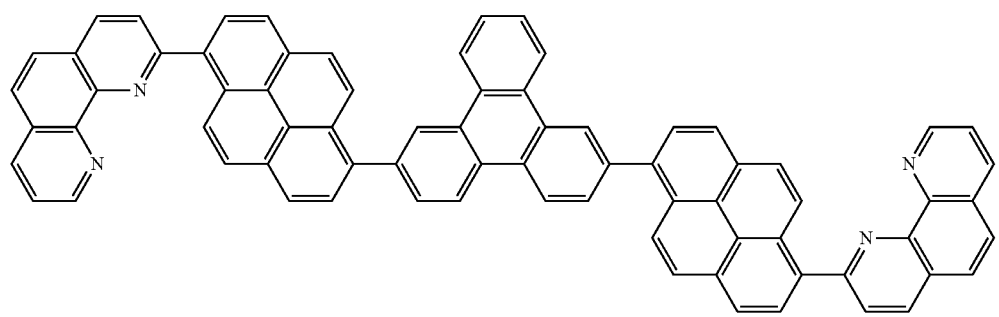
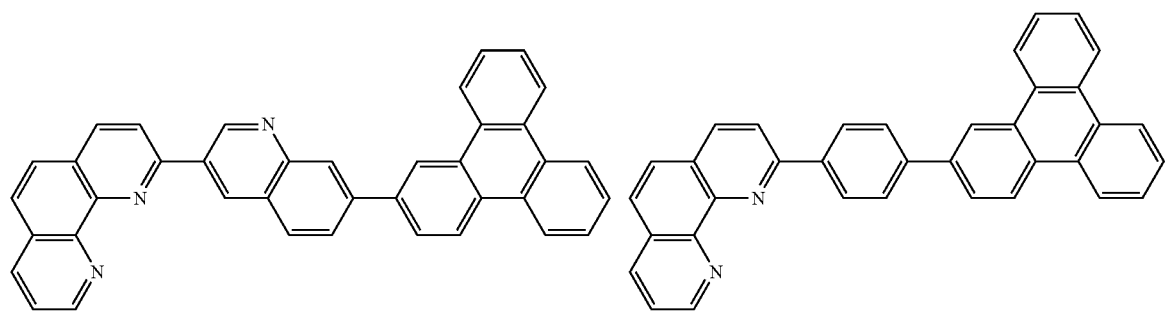
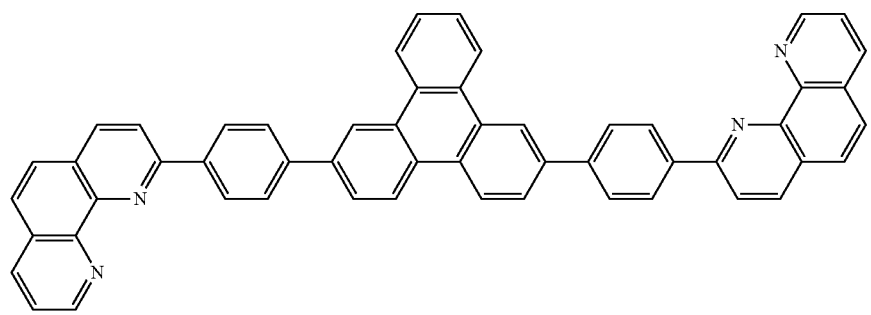
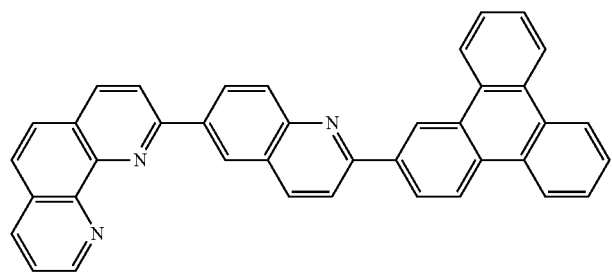

-continued
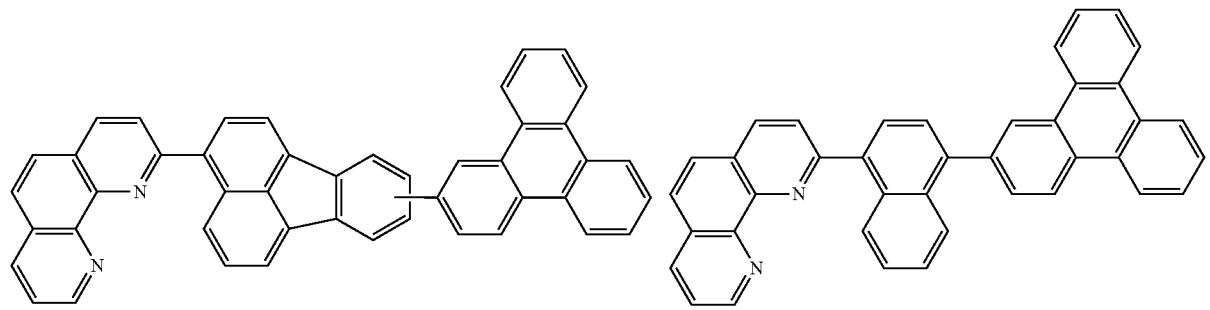
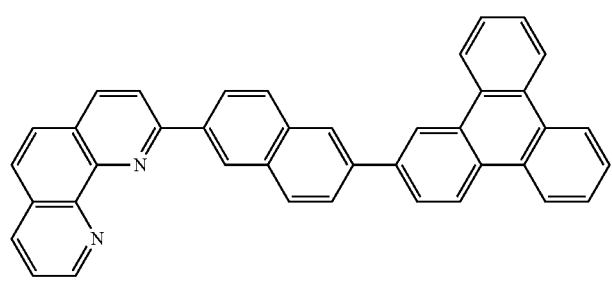
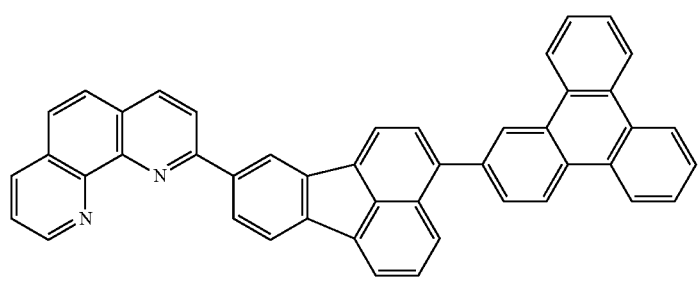
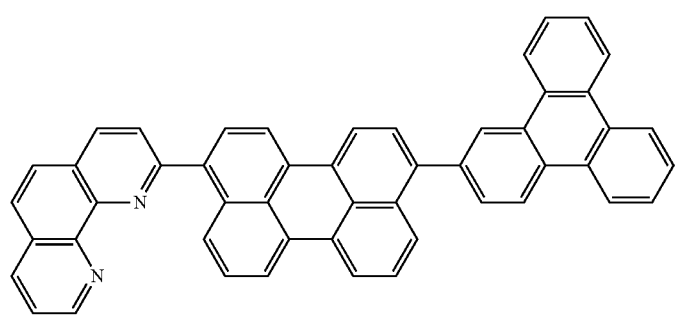
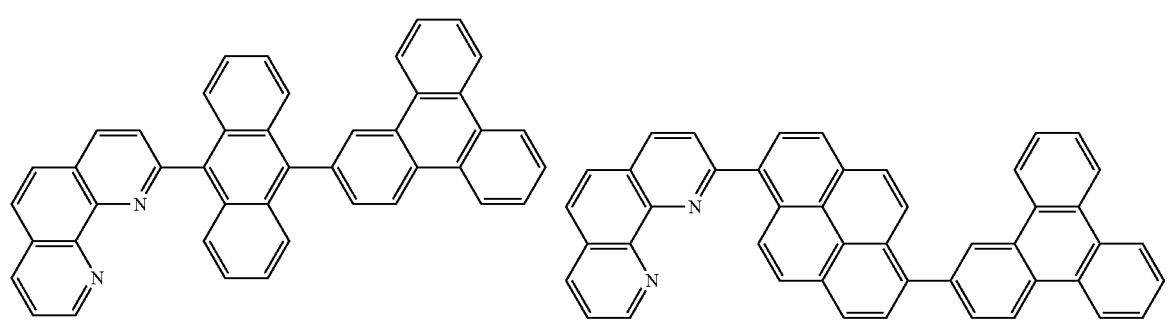

-continued
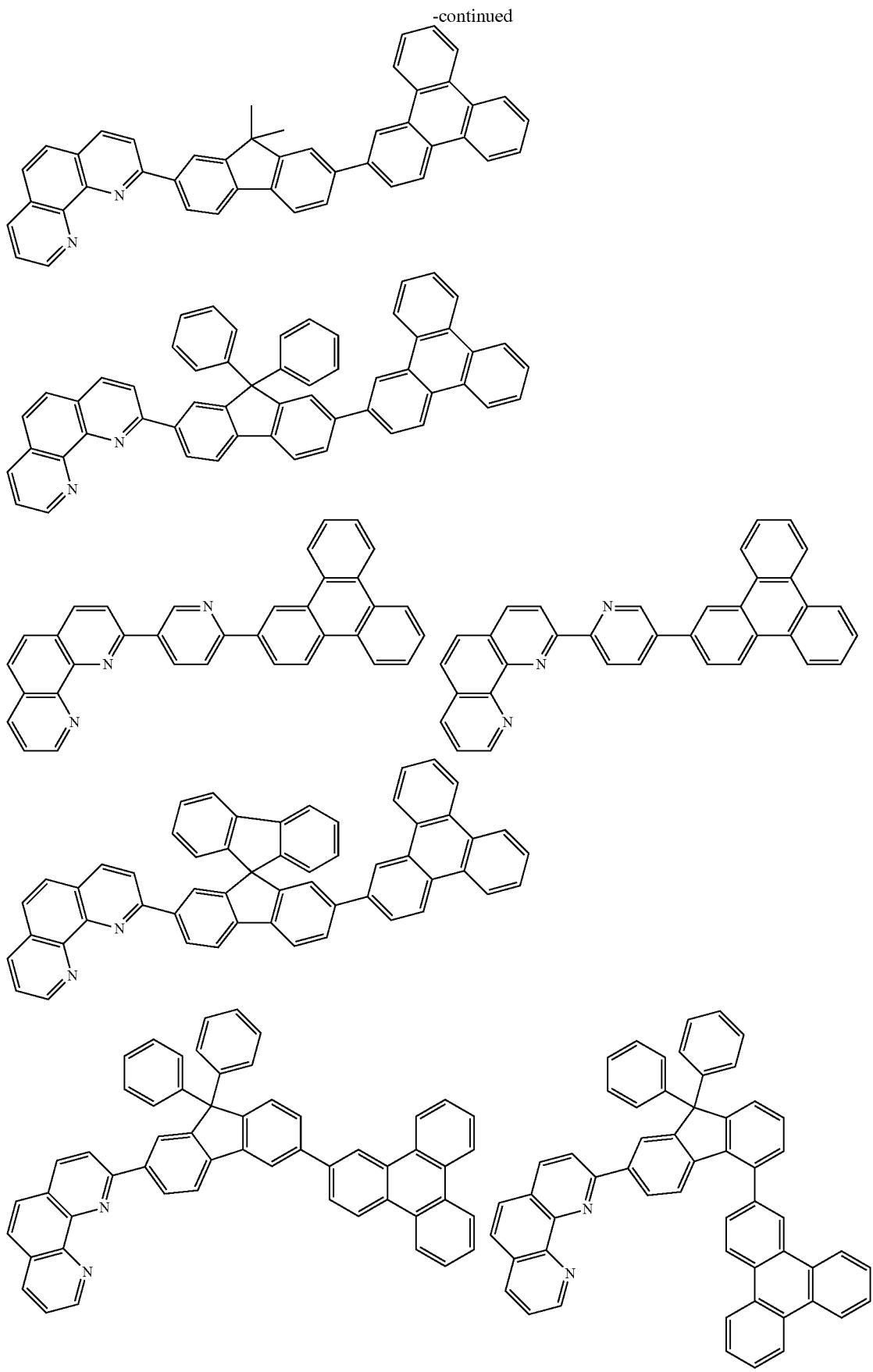

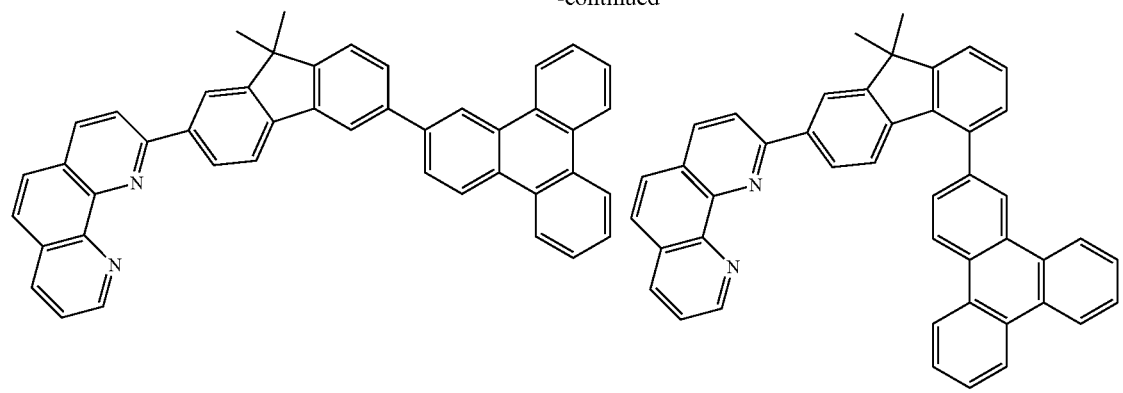
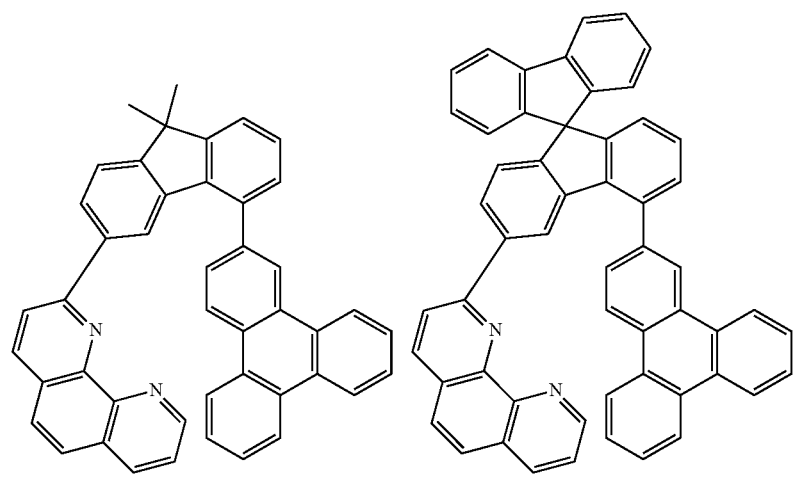
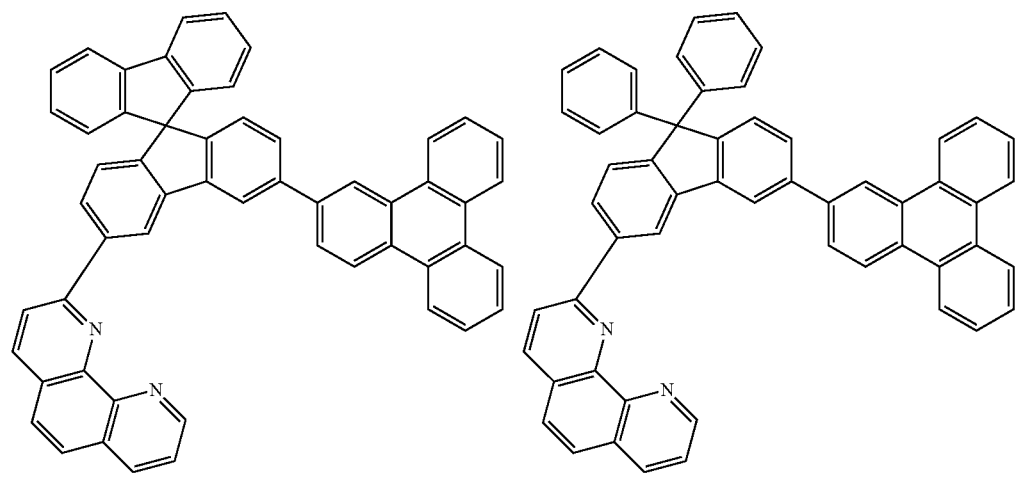
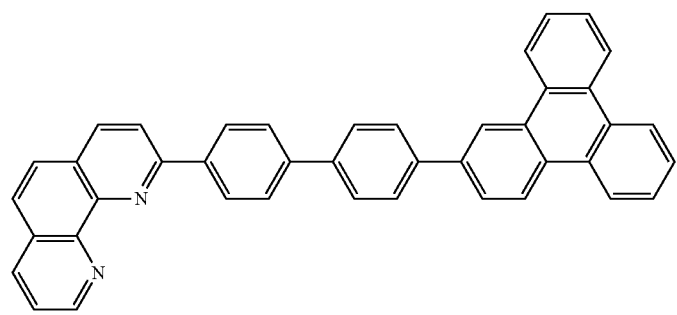

-continued
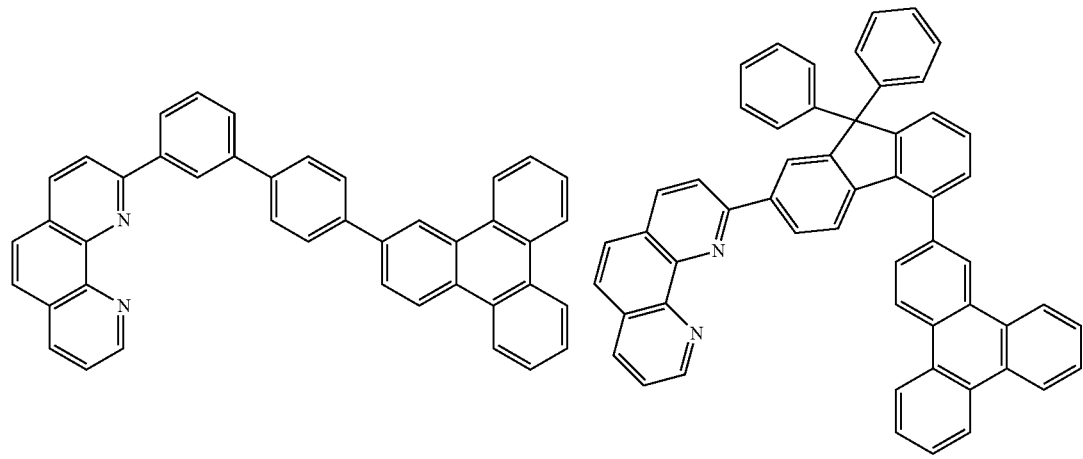
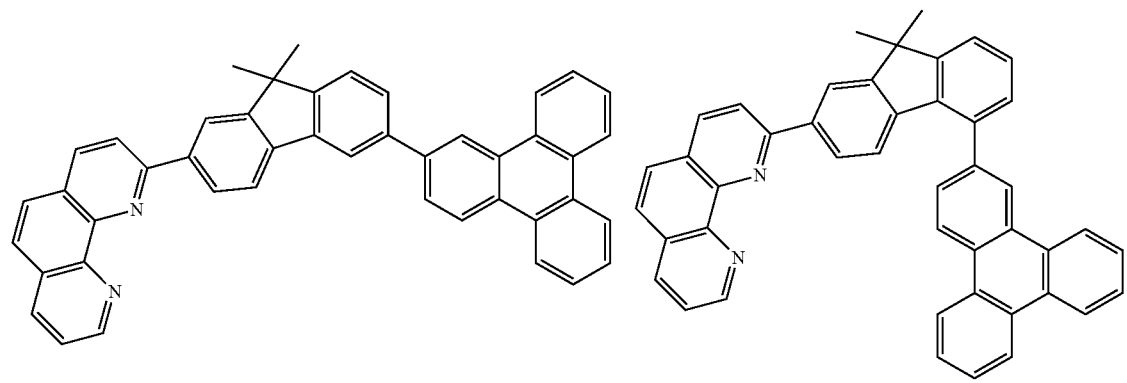
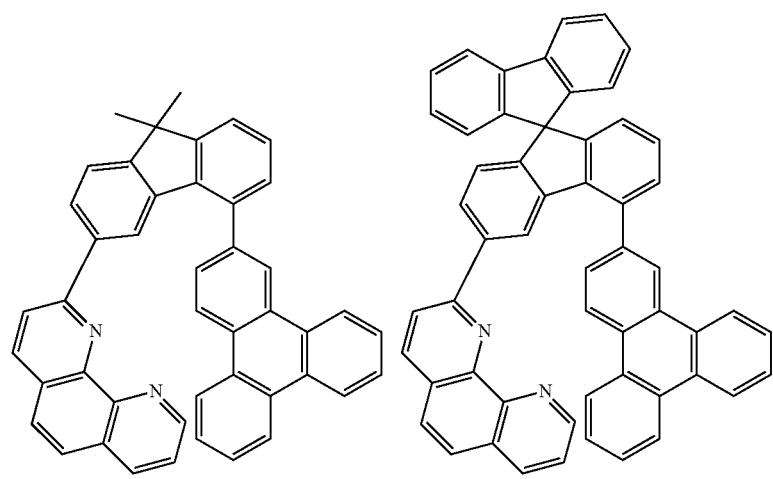

-continued
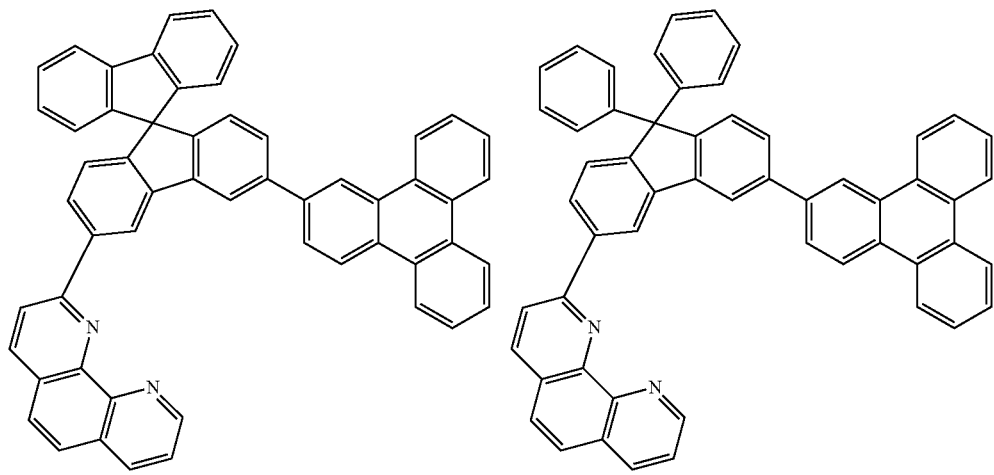
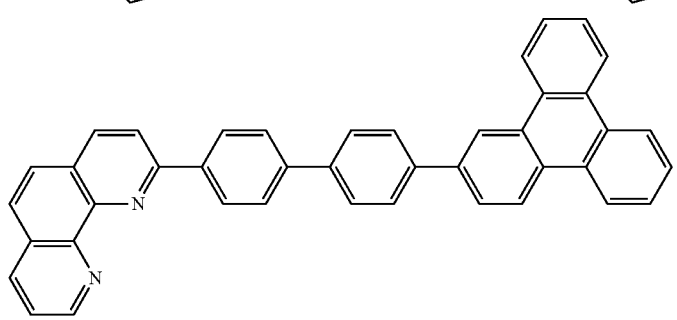
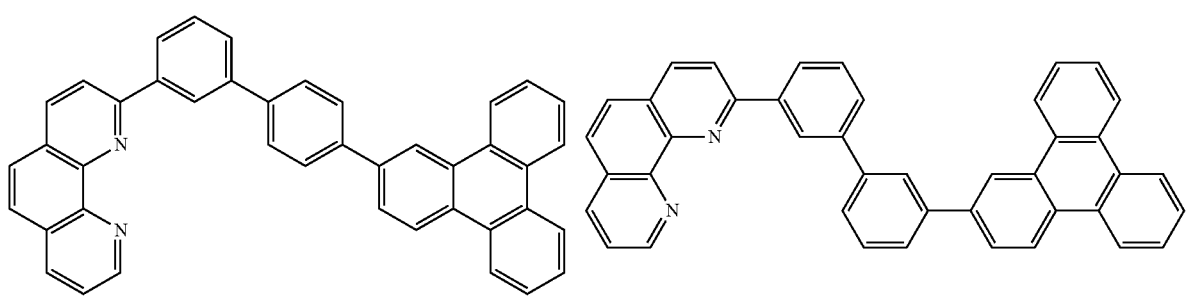
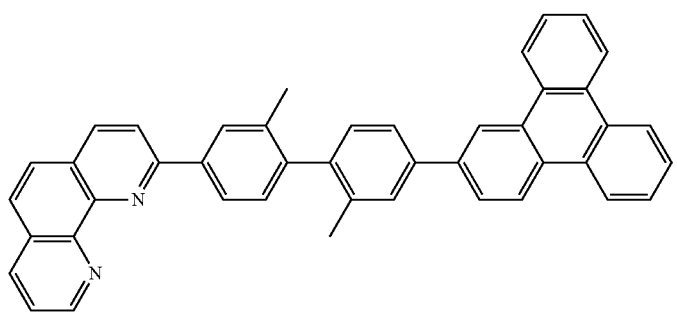
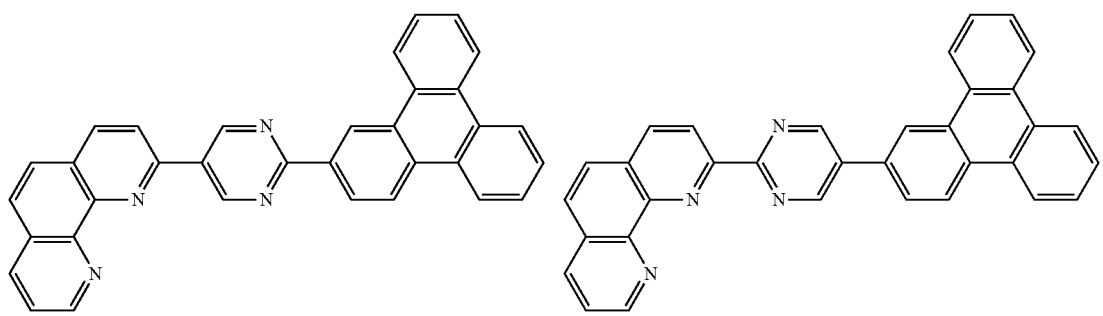

-continued
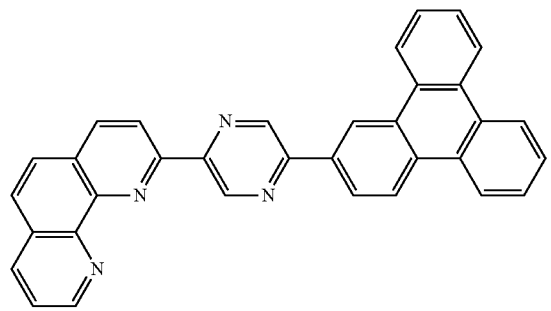
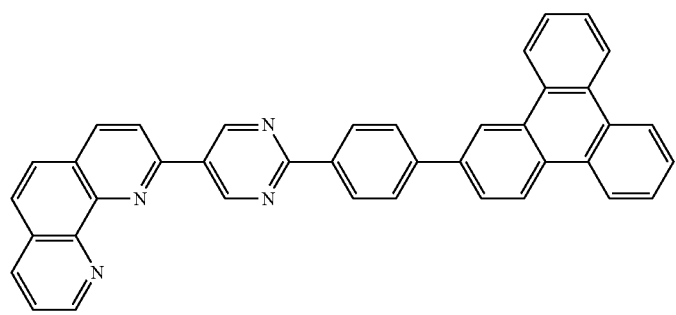
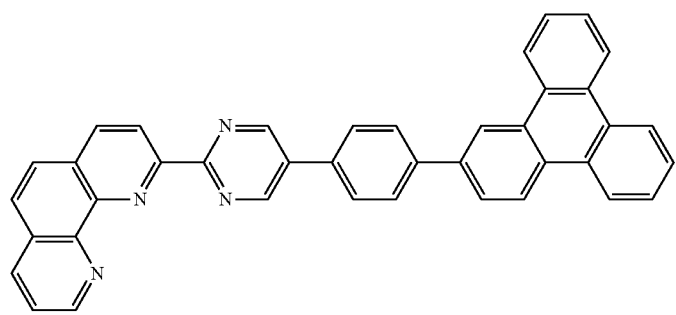
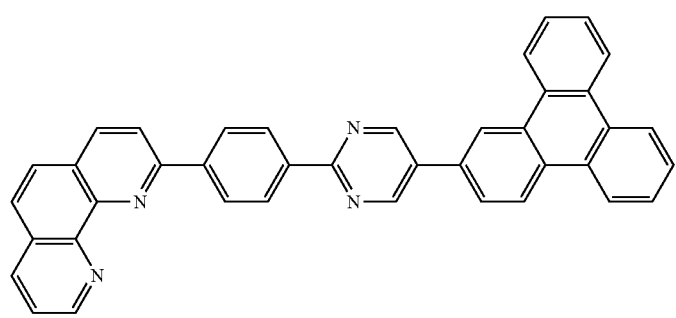
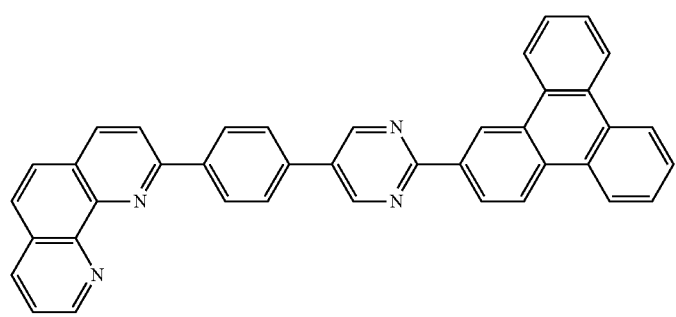

-continued
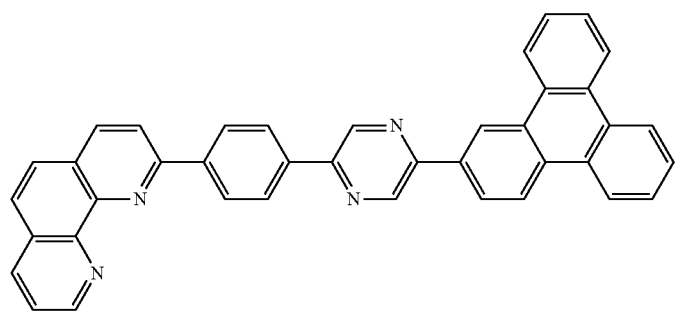
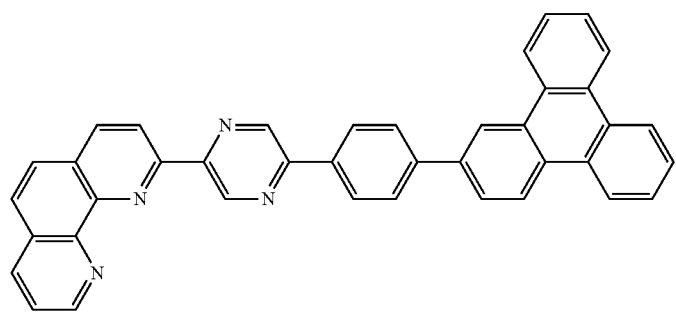
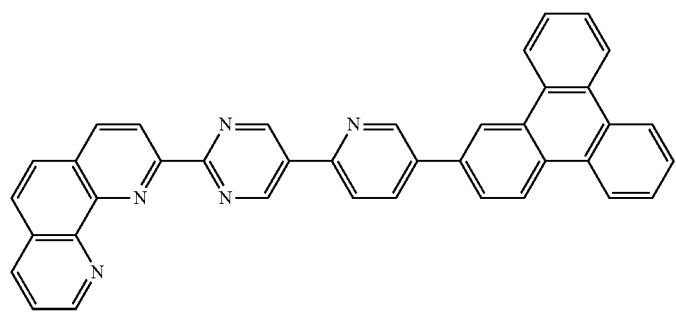
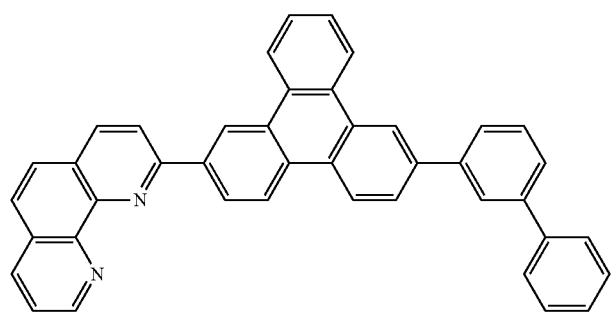
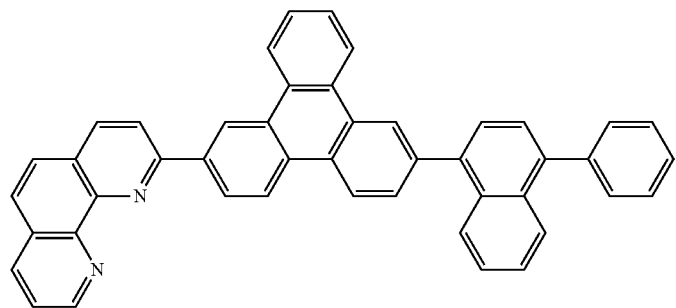

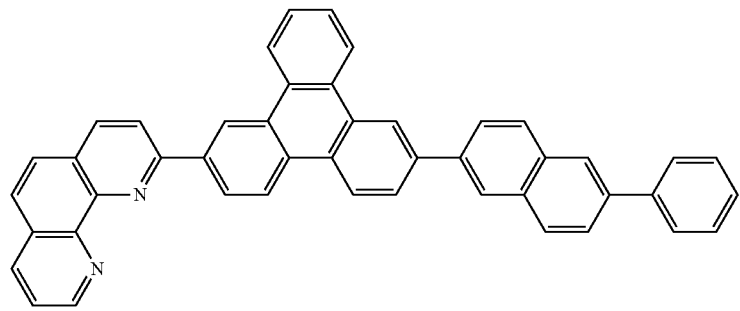
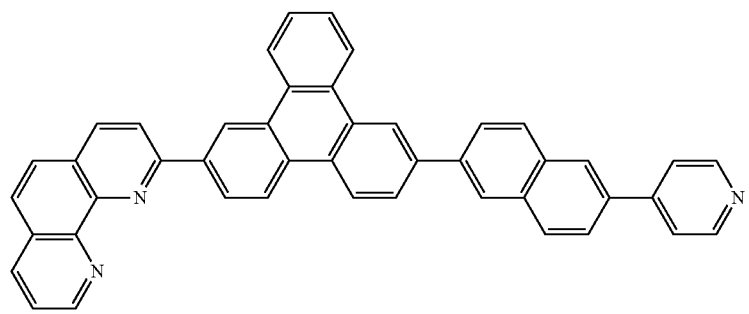
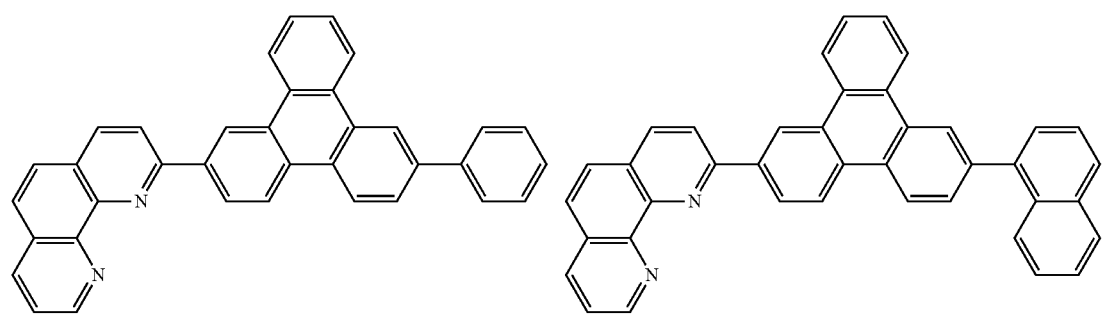
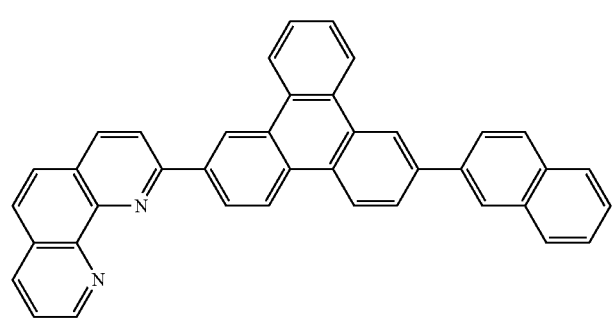
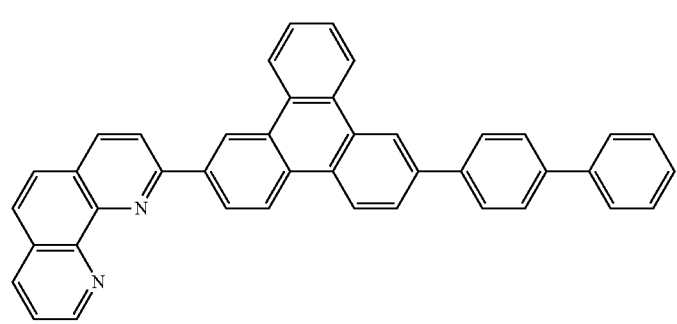

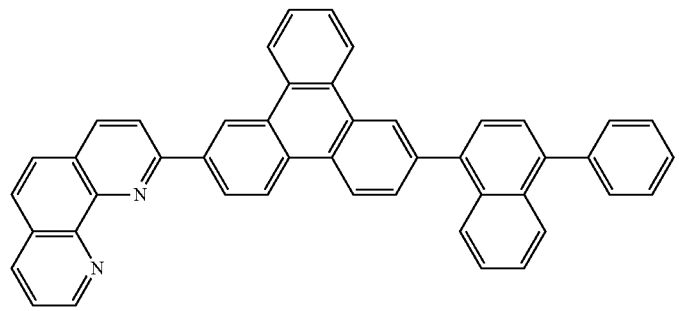
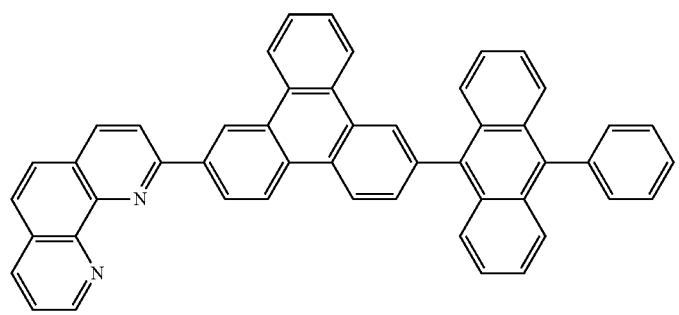
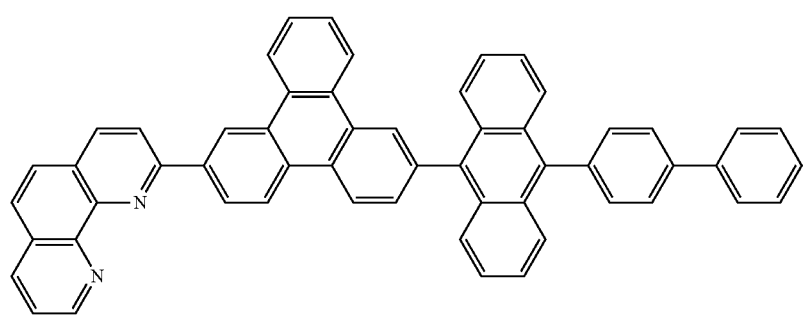
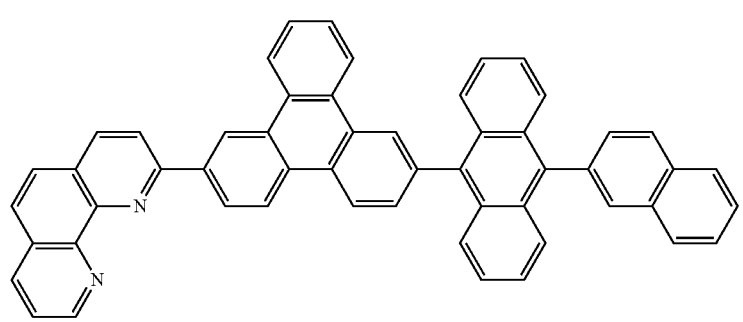
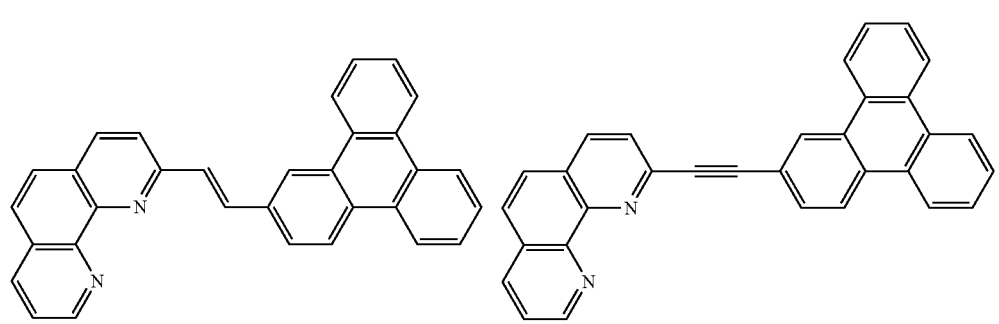

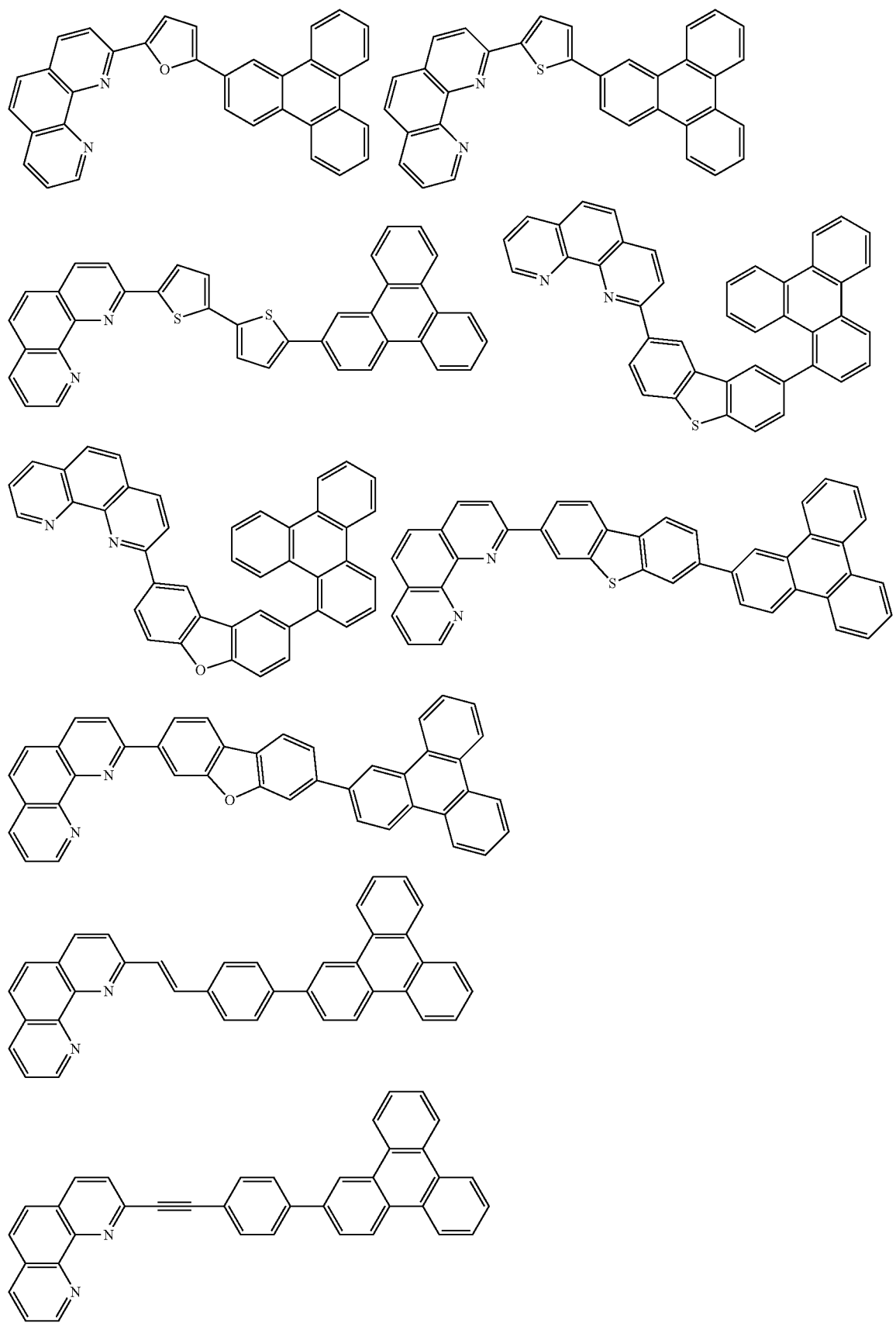

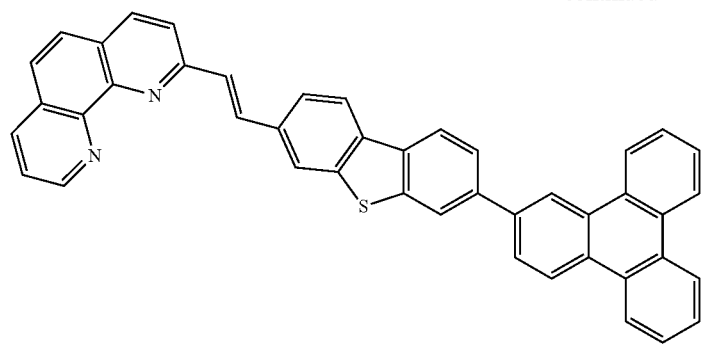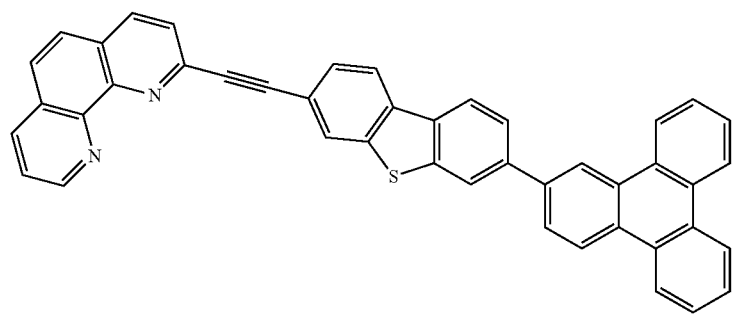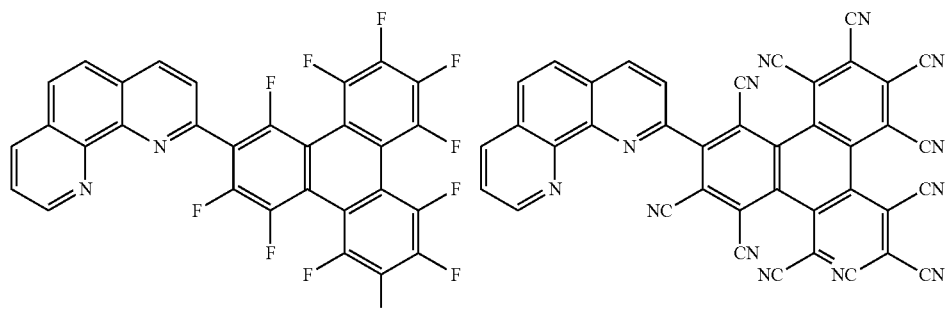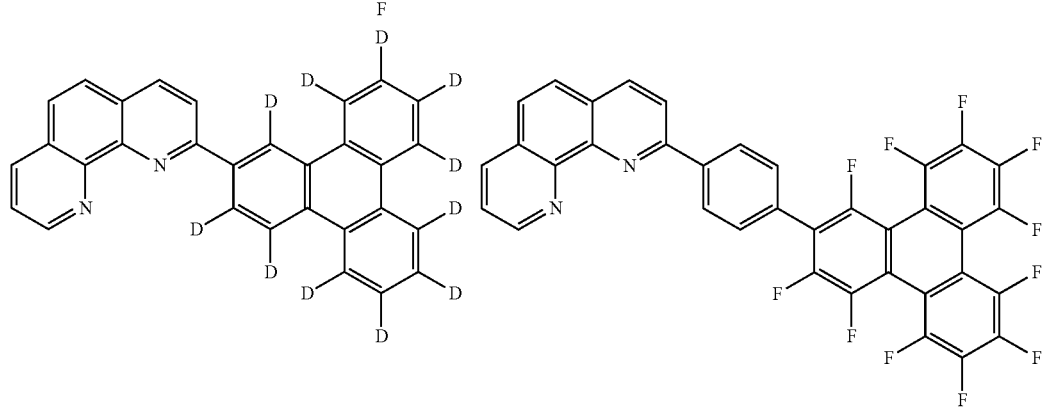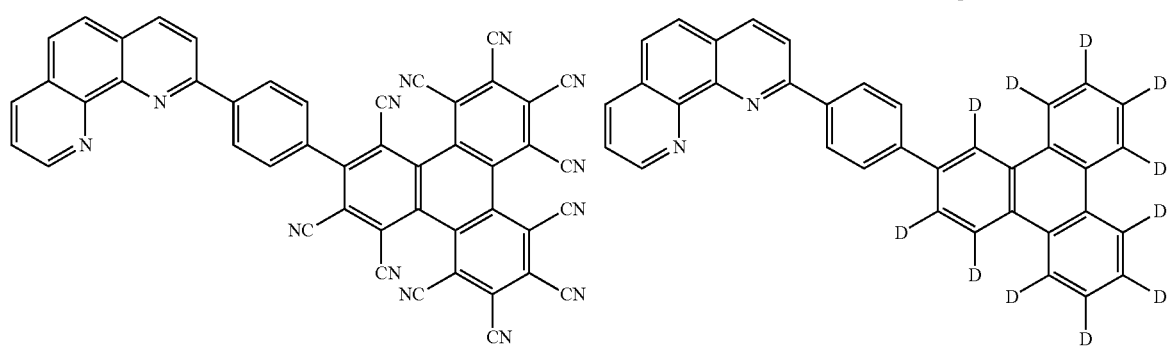

-continued

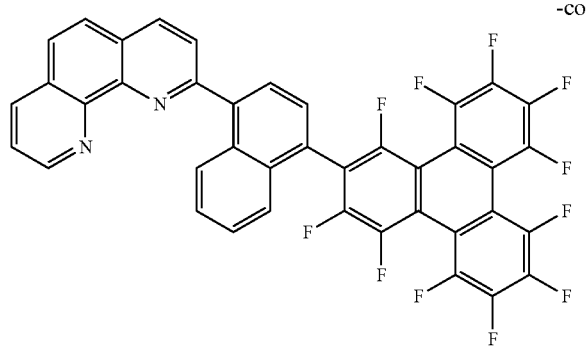

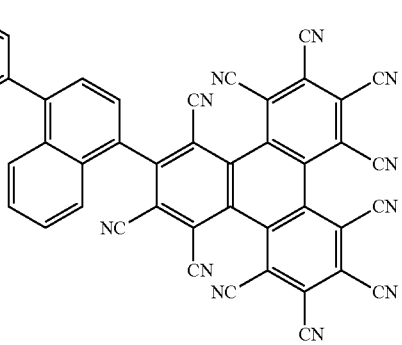

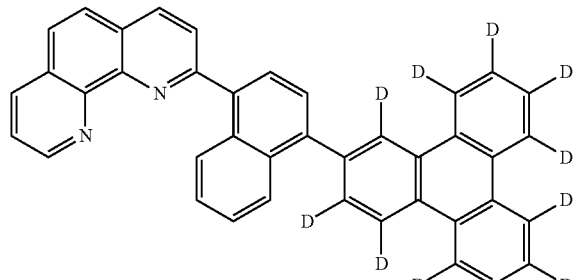

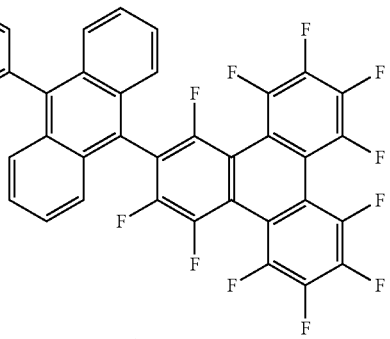

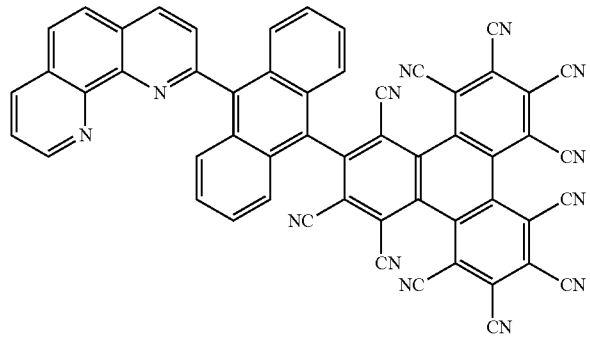

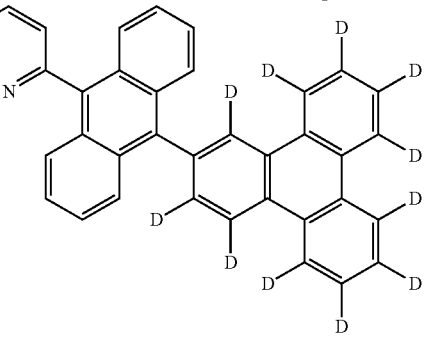

The charge generation layer comprises an N-type charge generation layer, and the compound is included in the N-type charge generation layer.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the disclosure and are incorporated in and constitute a part of this specification, illustrate embodiments of the disclosure and together with the description serve to explain the principles of the disclosure. In the drawings.

DETAILED DESCRIPTION

Figure 1:
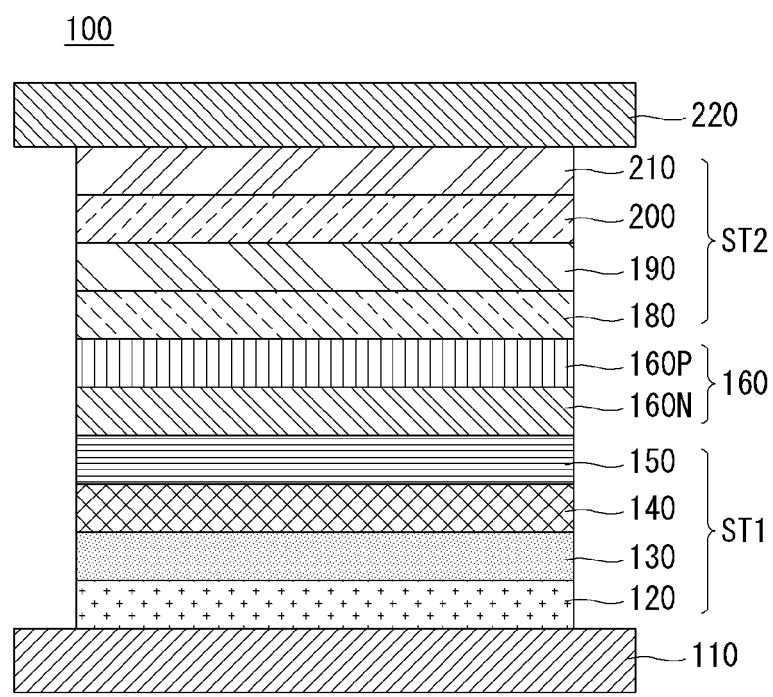
FIG. 1 is a view showing an organic light emitting display device according to a first exemplary embodiment of the present disclosure.

The advantages and features of the present disclosure and methods for accomplishing the same may be understood more readily by reference to the following detailed descriptions of exemplary embodiments and the accompanying drawings. The present disclosure may, however, be embodied in many different forms and should not be construed as being limited to the exemplary embodiments set forth herein. Rather, these exemplary embodiments are provided so that this disclosure will be thorough and complete and will fully convey the concept of the present disclosure to those skilled in the art, and the present disclosure is defined by the appended claims The shapes, sizes, percentages, angles, numbers, etc. shown in the figures to describe the exemplary embodiments of the present disclosure are merely examples and not limited to those shown in the figures. Like reference numerals denote like elements throughout the specification. In describing the present disclosure, detailed descriptions of related well-known technologies will be omitted to avoid unnecessary obscuring the present disclosure. When the terms 'comprise', 'have', 'consist of' and the like are used, other parts may be added as long as the term 'only' is not used. The singular forms may be interpreted as the plural forms unless explicitly stated.

The elements may be interpreted to include a margin of error even if not explicitly stated.

When the position relation between two parts is described using the terms 'on', 'over', 'under', 'next to' and the like, one or more parts may be positioned between the two parts as long as the term 'immediately' or 'directly' is not used.

When the temporal relationship between two events is described using the terms 'after', 'following', 'next', 'before' and the like, the two events may not occur in succession as long as the term 'immediately' or 'directly' is not used.

It will be understood that, although the terms first, second, etc., may be used to describe various elements, these elements should not be limited by these terms. These terms are only used to distinguish one element from another element. Thus, a first element discussed below could be termed a second element without departing from the technical spirit of the present disclosure.

The features of various exemplary embodiments of the present disclosure may be linked or combined with one another partly or wholly, and may technically interact or work together in various ways. The exemplary embodiments may be carried out independently or in combination with one another.

Hereinafter, various exemplary embodiments of the present disclosure will be described in detail with reference to the accompanying drawings.

FIG. 1 is a view showing an organic light emitting display device according to a first exemplary embodiment of the present disclosure.

Referring to FIG. 1, an organic light emitting display device 100 of this disclosure comprises light emitting parts ST1 and ST2 between an anode 110 and a cathode 220, and a charge generation layer 160 between the light emitting parts ST1 and ST2.

The anode 110 is a hole injection electrode, and may be formed of one among ITO (indium tin oxide), IZO (indium zinc oxide), or ZnO (zinc oxide) having a high work function. Also, if the anode 110 is a reflective electrode, the anode 110 may further comprise a reflective layer formed of one among aluminum (Al), silver (Ag), or nickel (Ni) under a layer formed of one among ITO, IZO, or ZnO.

The first light emitting part ST1 comprises a first light emitting layer 140. The first light emitting layer 140 may emit light of red (R), green (G), or blue (B), and may be formed of a fluorescent material or phosphorescent material. In this exemplary embodiment, the first light emitting layer 140 may be a blue light emitting layer. The blue light emitting layer comprises one among a blue light emitting layer, a dark blue light emitting layer, and a sky blue light emitting layer. Alternatively, the first light emitting layer 140 may be formed of a blue light emitting layer and a red light emitting layer, a blue light emitting layer and a yellow-green light emitting layer, or a blue light emitting layer and a green light emitting layer.

The first light emitting part ST1 comprises a hole injection layer 120 and a first hole transport layer 130 that are between the anode 110 and the first light emitting layer, and a first electron transport layer 150 on the first light emitting layer 140.

The hole injection layer 120 may function to facilitate hole injection from the anode 110 to the first light emitting layer 140, and may be formed of, but is not limited to, one or more among CuPc (copper phthalocyanine), PEDOT (poly(3,4)-ethylenedioxythiophene), PANI(polyaniline), and NPD (N,N'-bis(naphthalene-1-yl)-N,N'-bis(phenyl)-2, 2'-dimethylbenzidine). The hole injection layer 120 may have a 1 to 150 nm thickness. If the hole injection layer 120 has a 1 nm thickness or greater, the hole injection properties may be improved, or if the hole injection layer 120 has a 150 nm thickness or less, an increase in the thickness of the hole injection layer 120 may be prevented and a rise in operating voltage may be therefore prevented. The hole injection layer 120 may not be included in the elements of the organic light emitting display device, depending on the structure or characteristics of the organic light emitting display device.

The first hole transport layer 130 may function to facilitate hole transport, and may be formed of, but is not limited to, one or more among NPD(N,N'-bis(naphthalene-1-yl)-N, N'-bis(phenyl)-2,2'-dimethylbenzidine), TPD(N,N'-bis-(3-methylphenyl)-N,N'-bis(phenyl)-benzidine), spiro-TAD(2, 2'7,7'-tetrakis(N,N-diphenylamino)-9,9'-spirofluorene), and MTDATA(4,4',4''-Tris(N-3-methylphenyl-N-phenylamino)-triphenylamine). The first hole transport layer 130 may have a 1 to 150 nm thickness. If the first hole transport layer 130 has a 1 nm thickness or greater, the hole transport properties may be improved, or if the first hole transport layer 130 has a 150 nm or less thickness, an increase in the thickness of the first hole transport layer 130 may be prevented, and a rise in operating voltage may be therefore prevented.

The first electron transport layer 150 may be formed of, but is not limited to, one or more among $Alq_3$(tris(8-hydroxyquinolinato)aluminum), PBD(2-4-biphenyl)-5-(4-tert-butylphenyl)-1,3,4-oxadiazole), TAZ(3-(4-biphenyl)-4-pheynyl-5-tert-butylphenyl-1,2,4-triazole), DPT(2-biphenyl-4-yl-4,6-bis-(4'-pyridin-2-yl-biphenyl-4-yl)-[1,3, 5]triazine), and BAlq(Bis(2-methyl-8-quinolinolato)-4-(phenylphenolato)aluminum). The first electron transport layer 150 may have a 1 to 150 nm thickness. If the first electron transport layer 150 has a 1 nm thickness or greater, a degradation of the electron transport properties may be prevented, or if the first electron transport layer 150 has a 150 nm thickness or less, an increase in the thickness of the first electron transport layer 150 may be prevented, and a rise in operating voltage may be therefore prevented.

Accordingly, the first light emitting part ST1 comprising the hole injection layer 120, the first hole transport layer 130, the first light emitting layer 140, and the first electron transport layer 150 is formed on the anode 110. The hole injection layer 120 may not be included in the elements of the organic light emitting display device, depending on the structure or characteristics of the organic light emitting display device.

A charge generation layer (CGL) 160 is between the first light emitting part ST1 and the second light emitting part ST2. The first light emitting part ST1 and the second light emitting part ST2 are connected by the charge generation layer 160. The charge generation layer 160 may be a PN-junction charge generation layer formed by joining an N-type charge generation layer 160N and a P-type charge generation layer 160P. The PN junction charge generation layer 160 generates a charge, or injects the charge, i.e., electrons and holes, separately into the light emitting layer. That is, the N-type charge generation layer 160N transfers electrons to the first electron transport layer 150, the first electron transport layer 150 supplies the electrons to the first light emitting layer 140 adjacent to the anode, and the P-type charge generation layer 160P transfers holes to the second hole transport layer 180 to supply the holes to a second light emitting layer 190 of the second light emitting part ST2. As such, the light emission efficiency of the first and second light emitting layers 140 and 190 may be further increased, and the operating voltage may be reduced. Accordingly, the charge generation layer 160 has a major effect on the light emission efficiency or operating voltage of the organic light emitting display device.

Thus, the present inventors conducted several tests or experiments to improve the electron injection properties of the N-type charge generation layer. Through these tests or experiments, they found out that the difference in LUMO (lowest unoccupied molecular orbital) energy level between the electron transport layer and the N-type charge generation layer causes a rise in operating voltage when the electrons injected into the N-type charge generation layer move to the electron transport layer. Also, they found out that, if the N-type charge generation layer is doped with a dopant such as an alkali metal or alkali earth metal, the alkali metal or alkali earth metal is diffused into the P-type charge generation layer, thus leading to a decrease in the lifetime of the device. In numerous tests or experiments, the present inventors introduced compounds for the N-type charge generation layer that can reduce operating voltage and improve lifetime.

Through a number of tests or experiments which were performed on materials that do not affect the lifetime or efficiency of the organic light emitting display device and that cause no rise in operating voltage, the present inventors developed compounds that increase electron mobility and prevent diffusion of the dopant in the N-type charge generation layer, with the use of a single material. Accordingly, they introduced a compound of this disclosure that consists of a material having similar electron mobility to that of an electron transport layer to improve the electron injection properties of the N-type charge generation layer and a material having a crystalline structure to facilitate electron movement.

A compound of this disclosure may facilitate electron transport since it has high electron mobility by comprising a core having two electron-rich nitrogen (N) atoms. Triphenylene was introduced as the core having two electron-rich nitrogen (N) atoms. Moreover, the compound of this disclosure includes $sp^2$ hybrid orbitals of nitrogen (N) that are relatively rich in electrons, and the nitrogen binds to an alkali metal or alkali earth metal, i.e., a dopant for the N-type charge generation layer, thereby forming a gap state. This gap state may facilitate transfer of electrons from the N-type charge generation layer to the electron transport layer. Also, an unshared electron pair of nitrogen binds well to the alkali metal or alkali earth metal included in the N-type charge generation layer, so the alkali metal or alkali earth metal is not diffused into the P-type charge generation layer, thereby improving lifetime. For example, this nitrogen binds well to lithium (Li), which is the dopant included in the N-type charge generation layer. Moreover, the compound of this disclosure includes a high-crystallinity functional group with a plate-like structure in order to improve electron mobility. Phenanthroline was introduced as the high-crystallinity functional group. The functional group binds well to the core owing to its strong n-conjugation and allows electrons to easily move through the crystalline structure because of its high crystallinity, thereby improving electron mobility.

Accordingly, the N-type charge generation layer 160N comprises a compound represented by the following Chemical Formula 1:

[Chemical Formula 1]

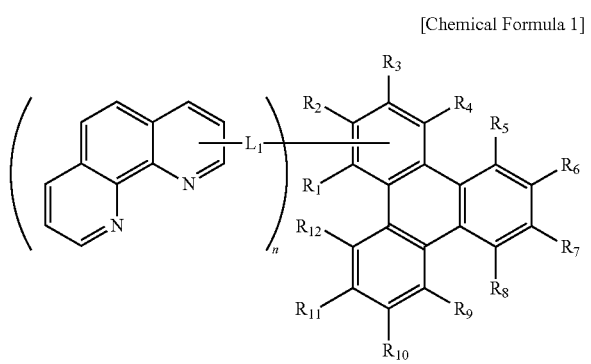

wherein $L_1$ includes a substituted or unsubstituted arylene group with 6 to 60 carbon atoms, a substituted or unsubstituted heteroarylene group with 3 to 60 carbon atoms, or a single bond, one of $R_1$ to $R_{12}$ binds to $L_1$, and the others that do not bind to $L_1$ include independently a substituted or unsubstituted aryl group with 5 to 30 carbon atoms, a substituted or unsubstituted heteroaryl group with 4 to 30 carbon atoms, a halogen group, a nitrile group, heavy hydrogen, or hydrogen. $L_1$ may include an aliphatic chain with 2 to 10 carbon atoms or an aliphatic ring compound with 2 to 10 carbon atoms, and n is 1 or 2. Substituents of the aryl group or heteroaryl group may preferably be one among phenyl, quinoline, pyridine, pyrimidine, triazine, naphthyl, terpyridine, biphenyl, phenanthrene, phenanthroline, pyrazine, carboline, fluorene, dibenzofluorene, thiophene, benzothiophene, dibenzothiophene, benzimidazole, methyl, ethyl, tert-butyl, trimethylsilyl, diphenylamine, triphenylamine, and cyanophenyl. Substituents of the arylene group or heteroarylene group may preferably be one among phenylene, quinolinylene, pyridinylene, pyrimidinylene, triazinylene, naphthylene, terpyridinylene, biphenylene, phenanthrenylene, phenanthrolinylene, pyrazinylene, carbolinylene, fluorenylene, substituted fluorenylene, dibenzofluorenylene, thiophenylene, benzothiophenylene, dibenzothiophenylene, benzimidazole, methylene, ethylene, tert-butylene, phenylamine, diphenylamine, and cyanophenylene.

The compound of this disclosure represented by Chemical Formula 1 may be one among the following compounds:

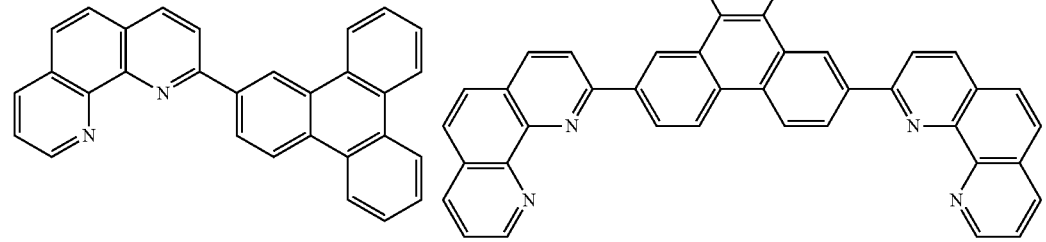

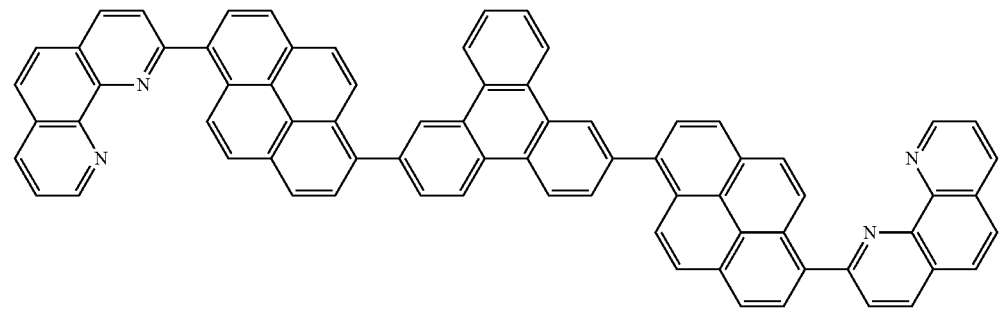

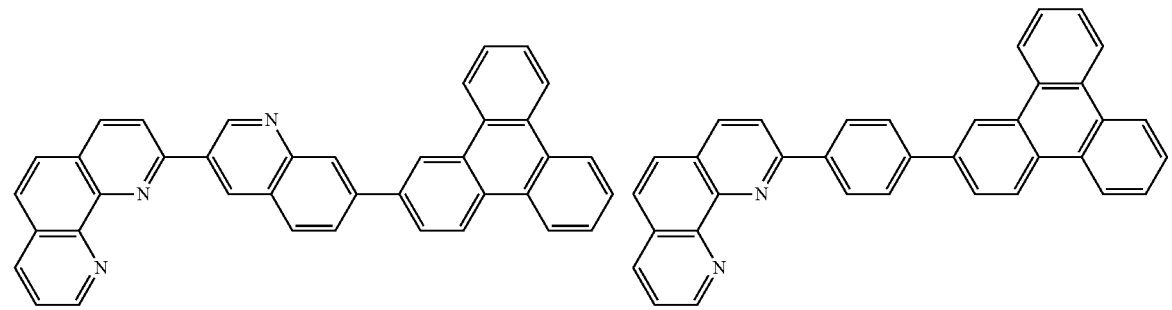

-continued
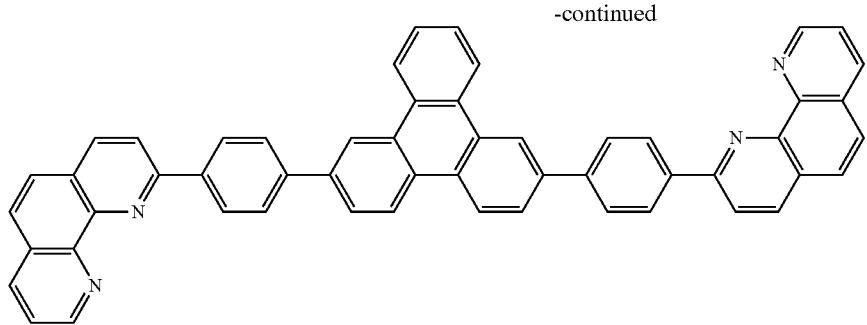
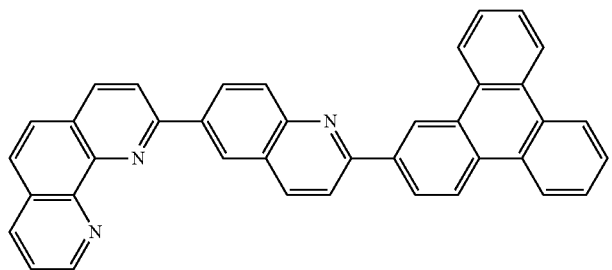
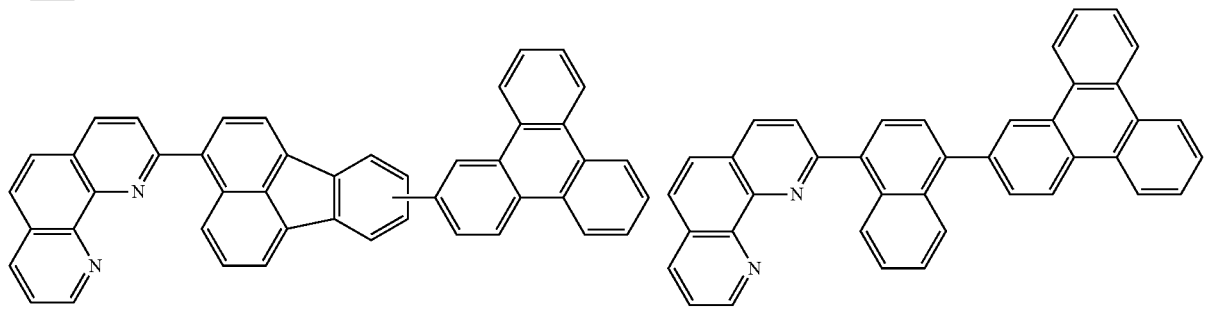
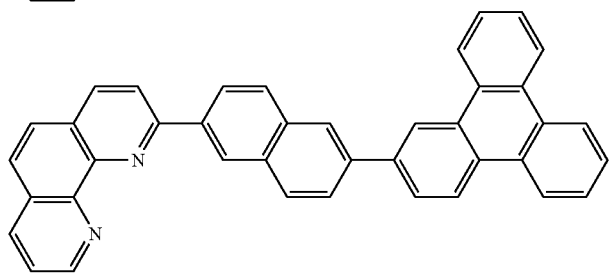
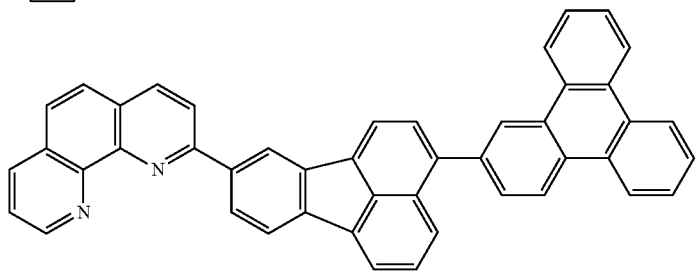
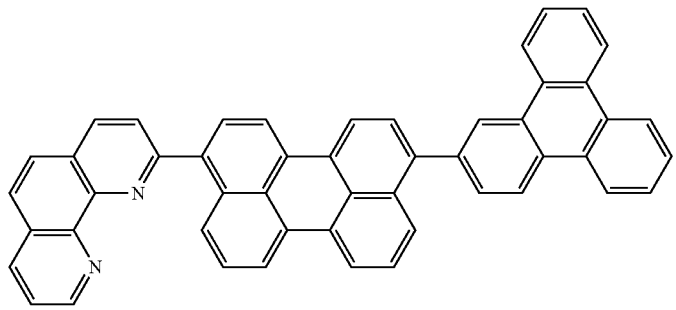

-continued
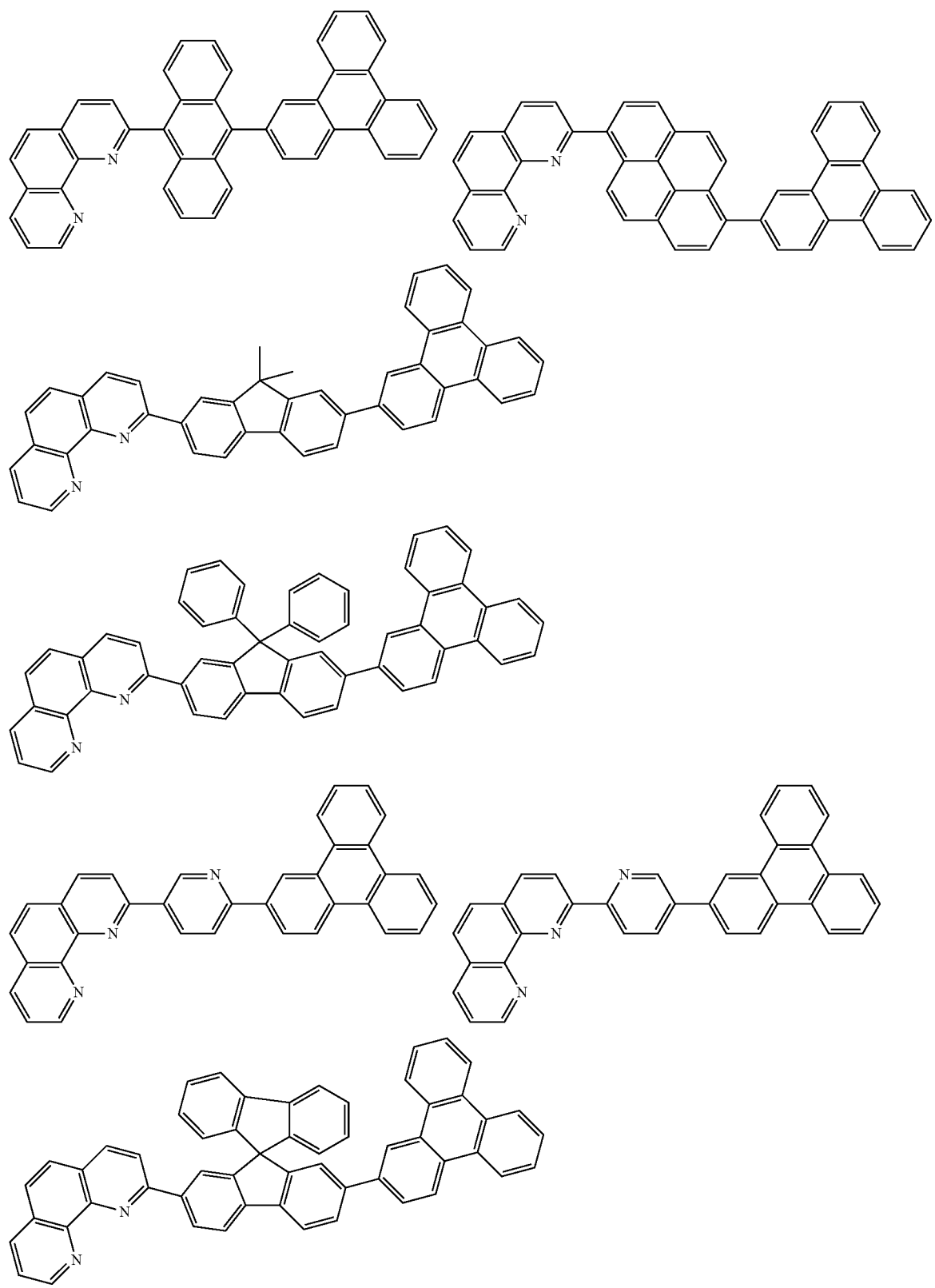

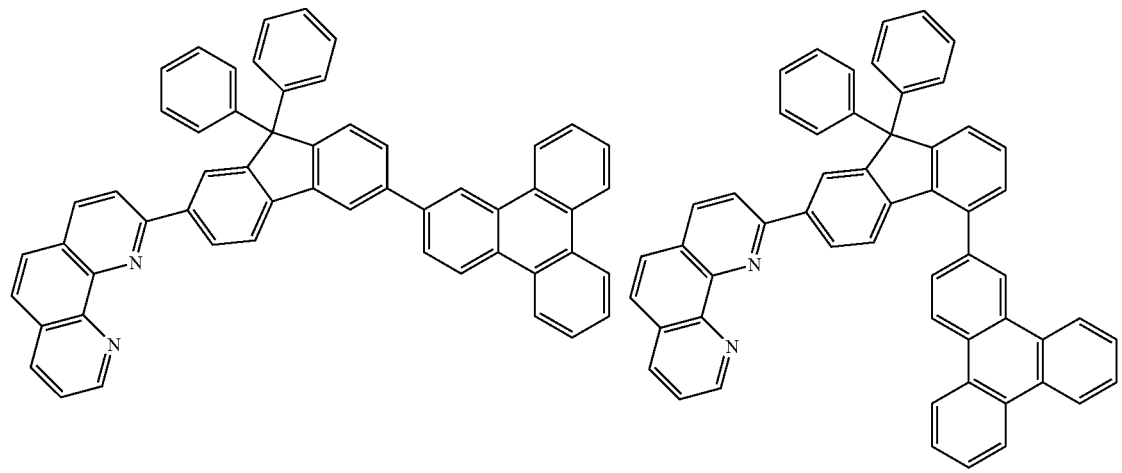
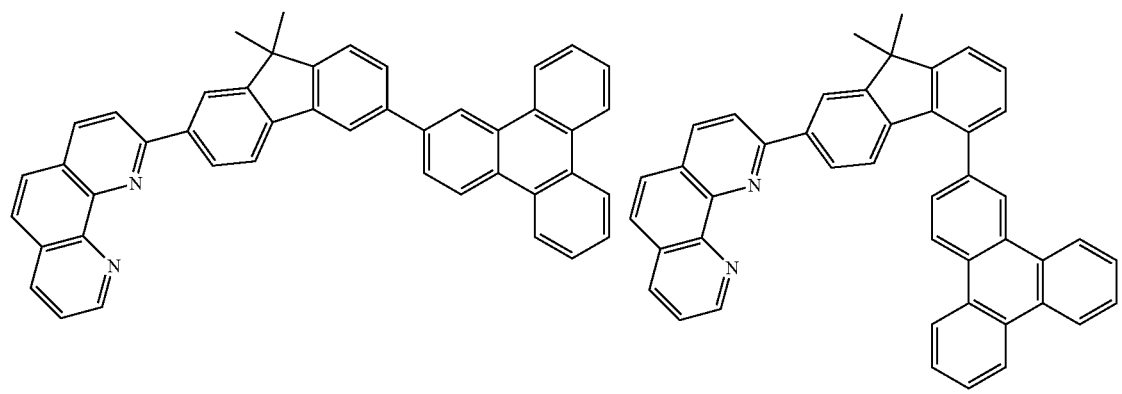
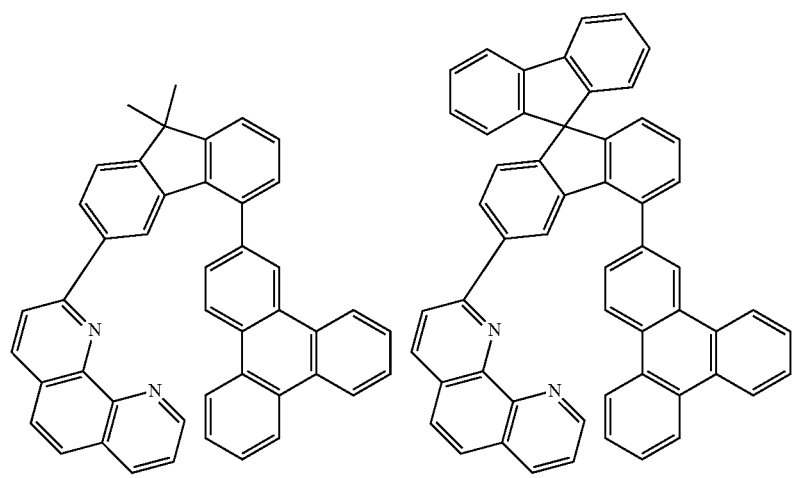

-continued
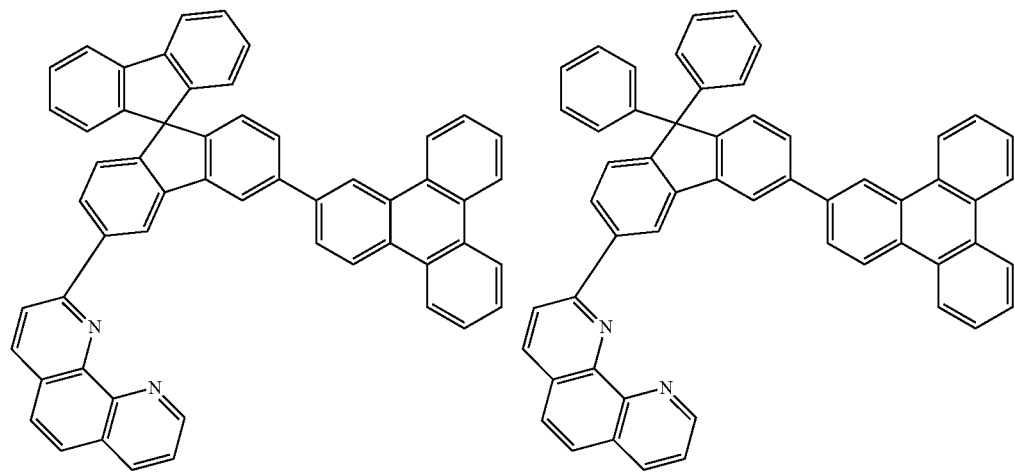
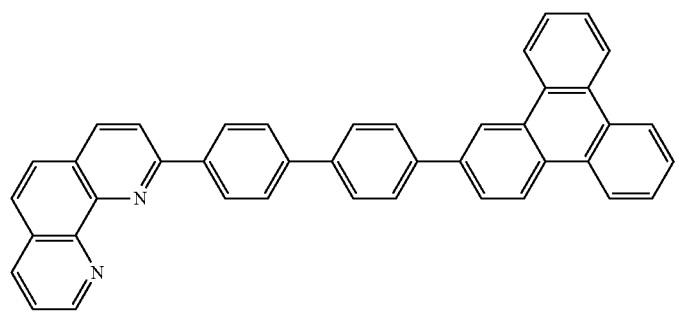
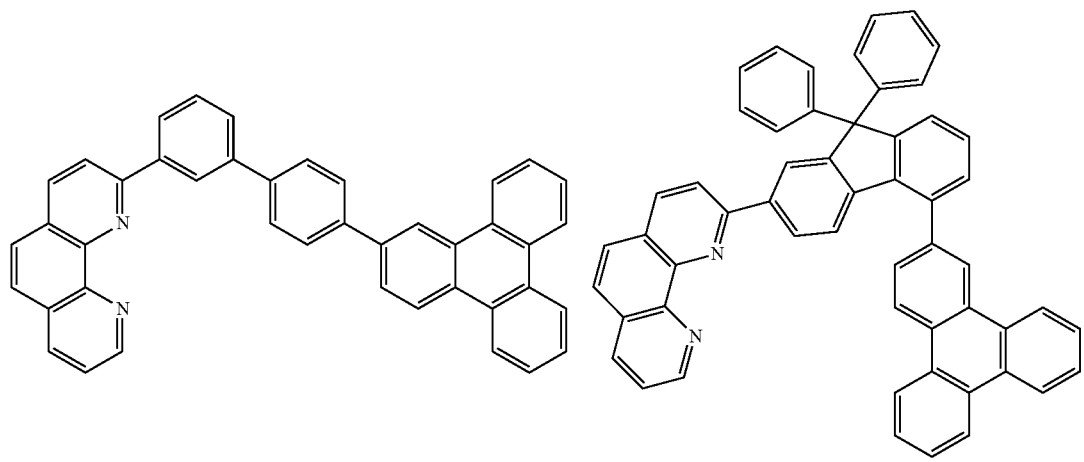
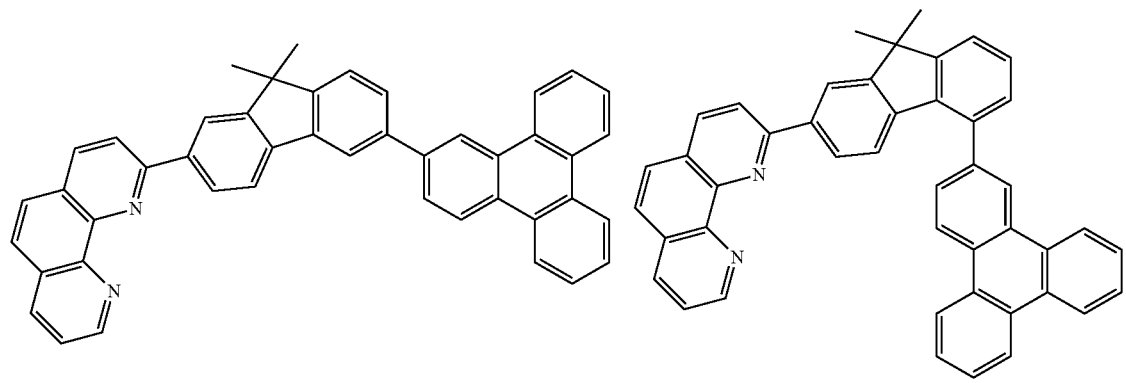

-continued
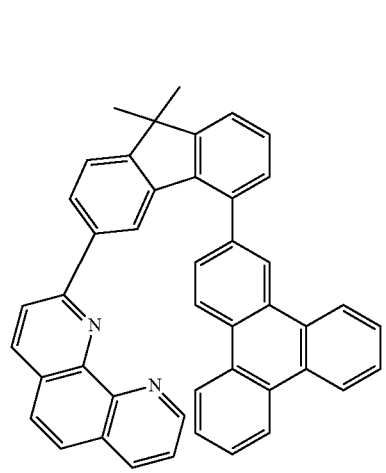
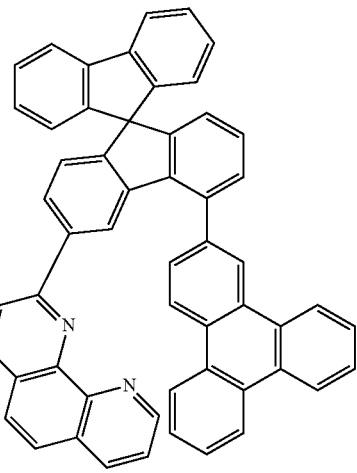
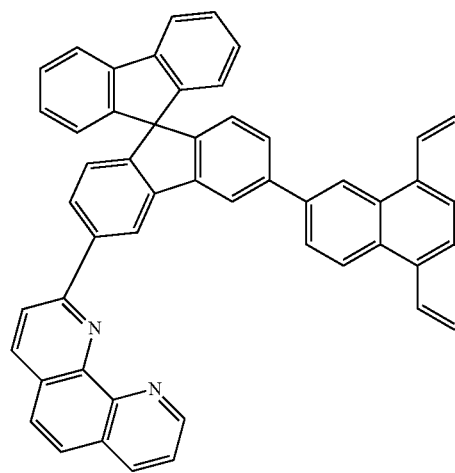
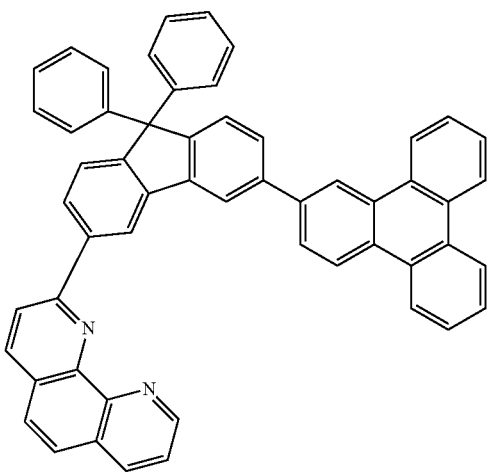
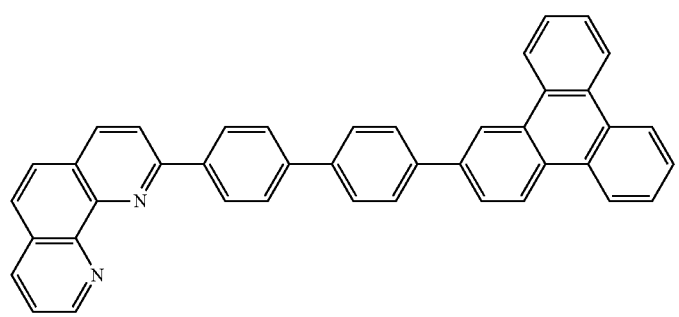
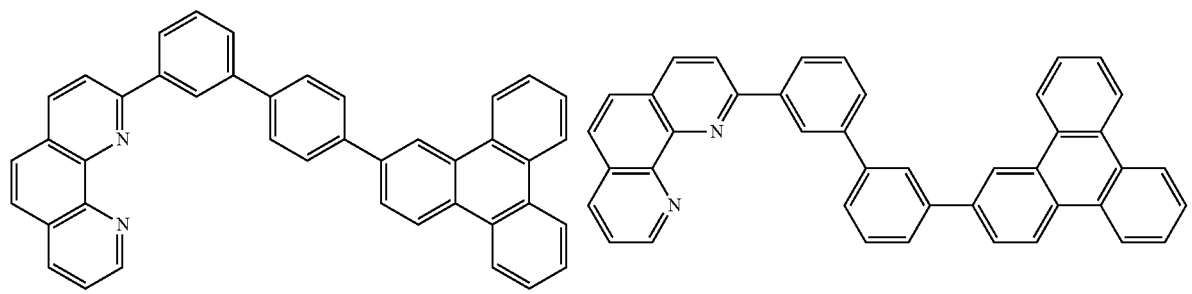

-continued
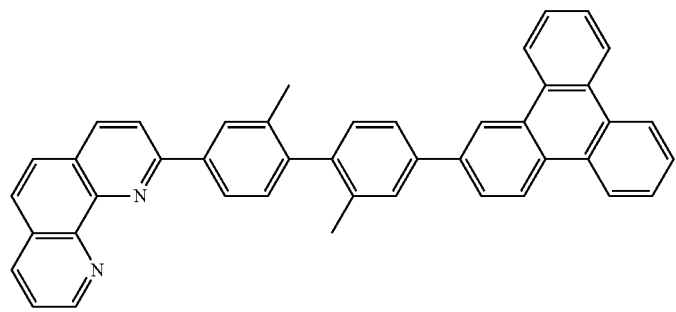
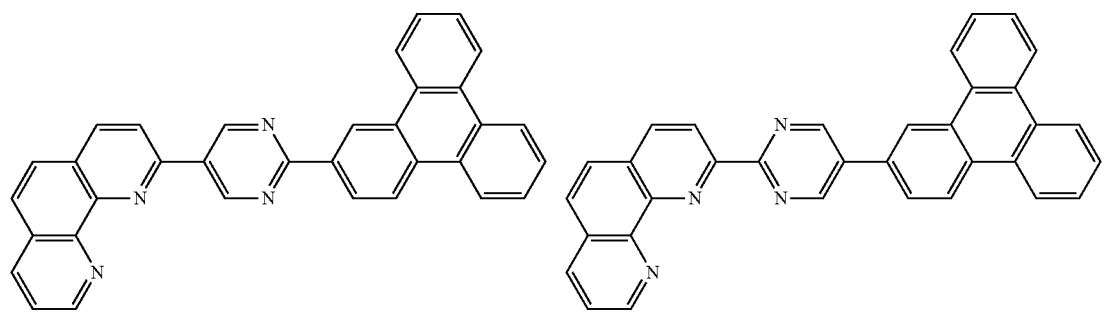
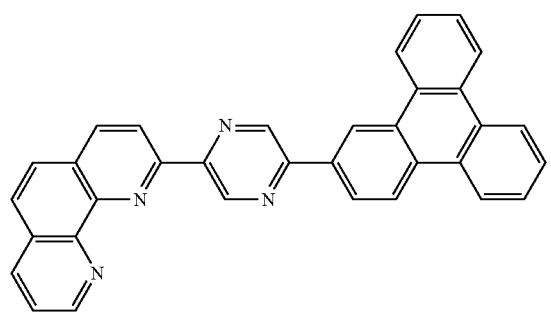
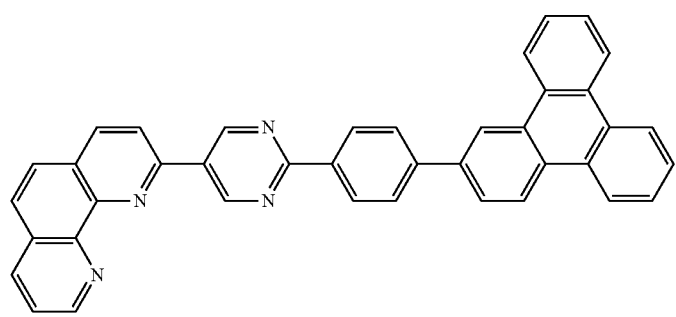
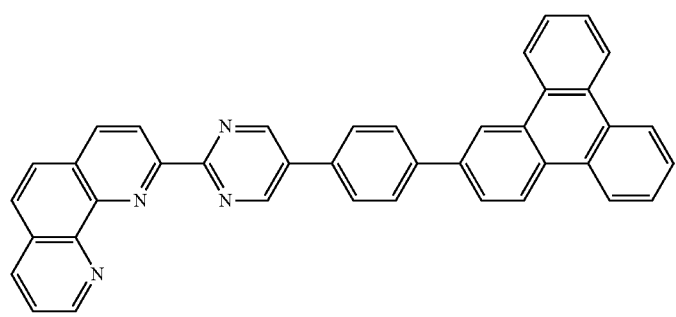

-continued
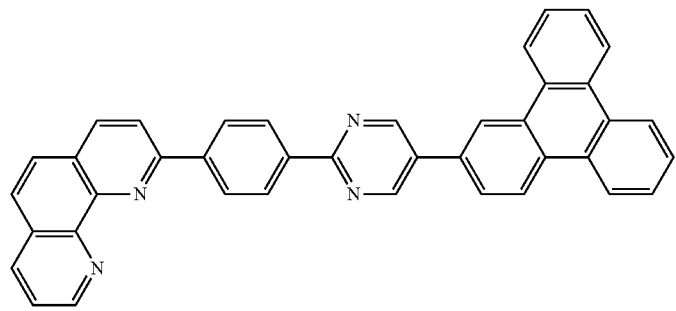
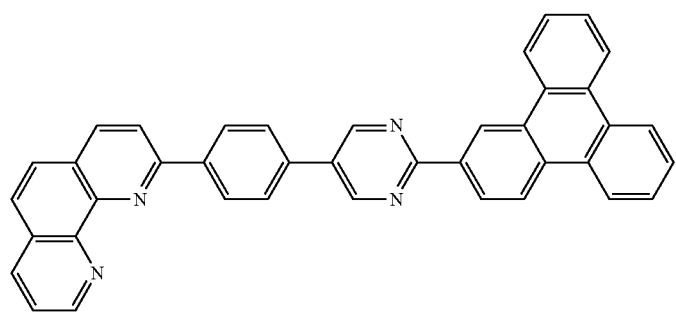
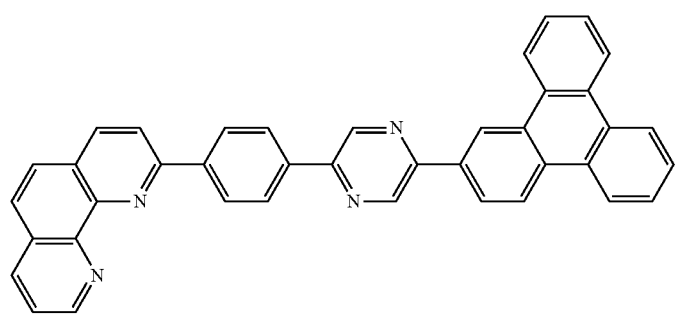
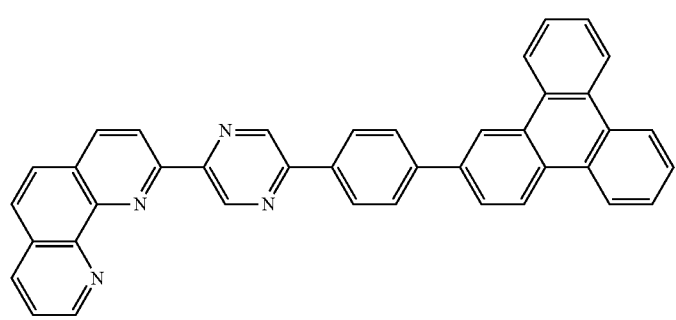
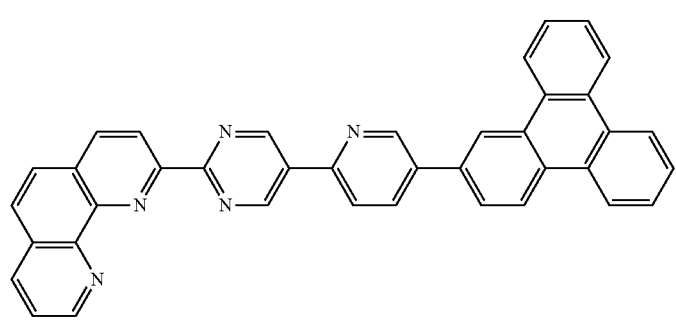

-continued
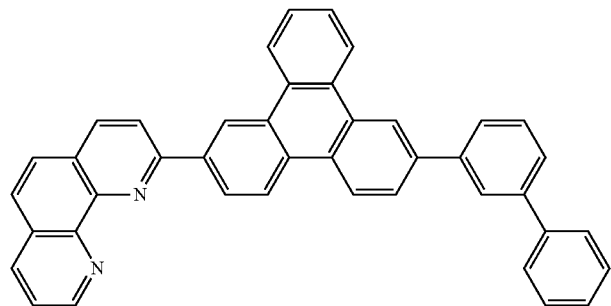
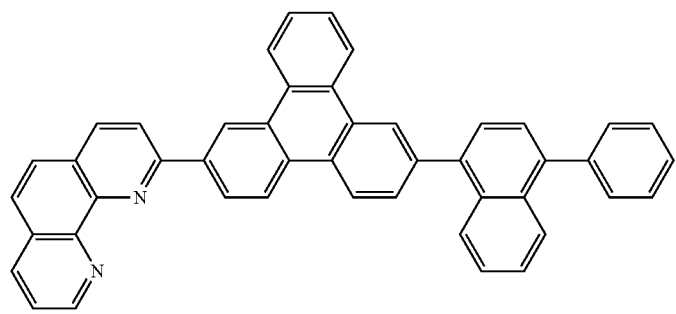
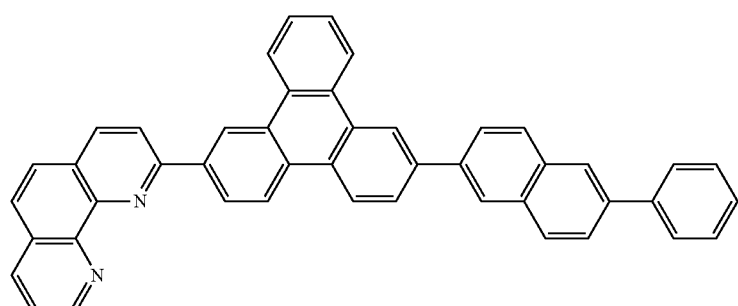
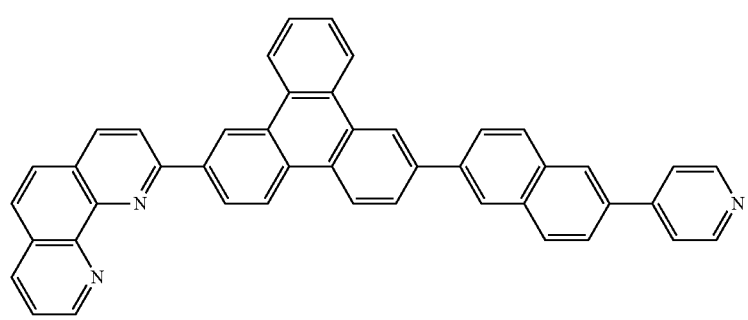
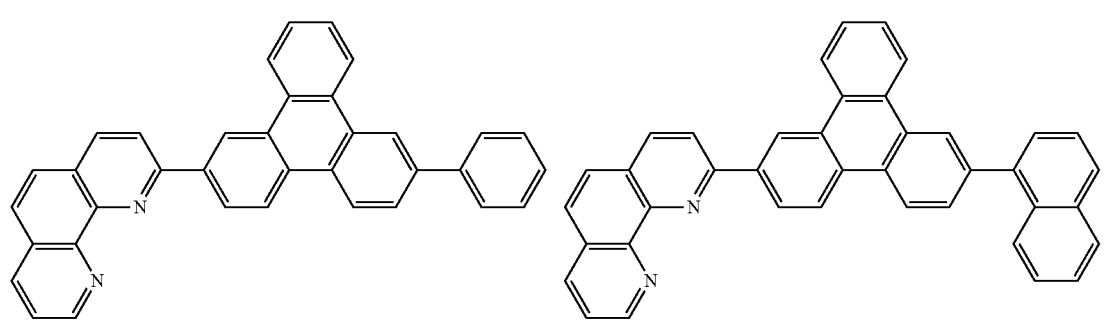

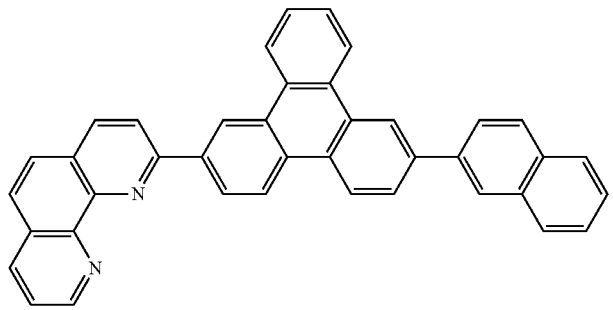
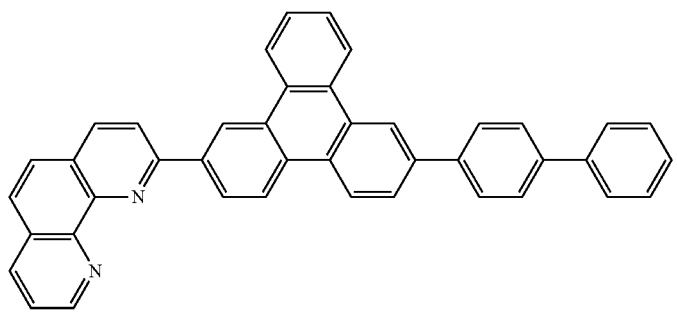
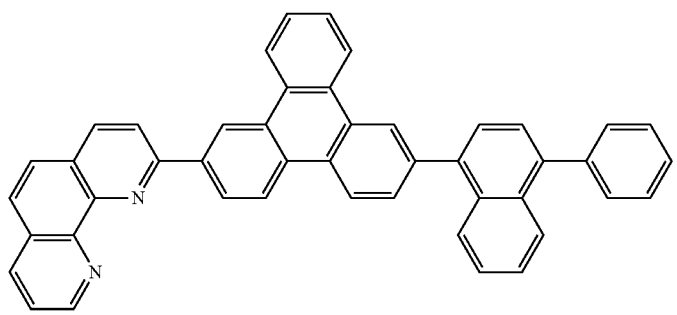
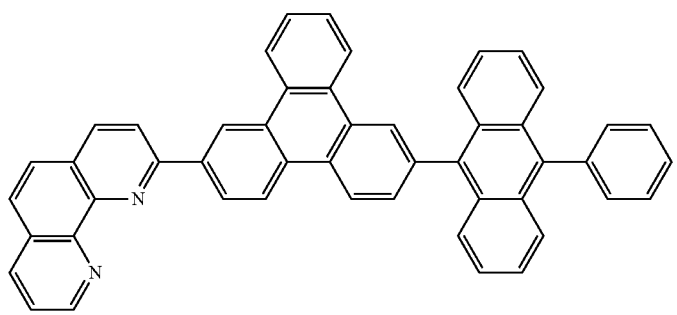
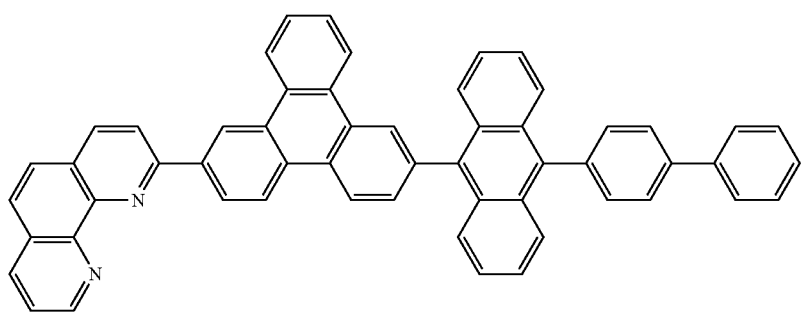

-continued
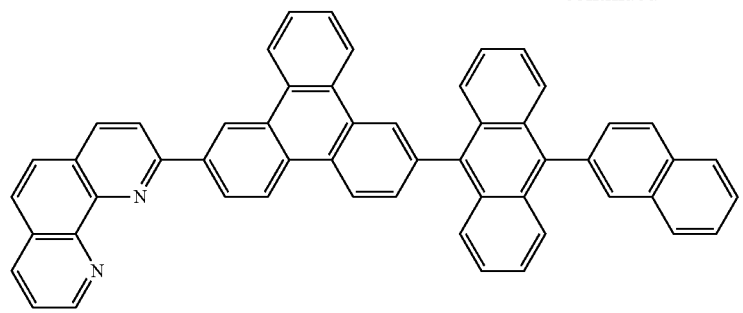
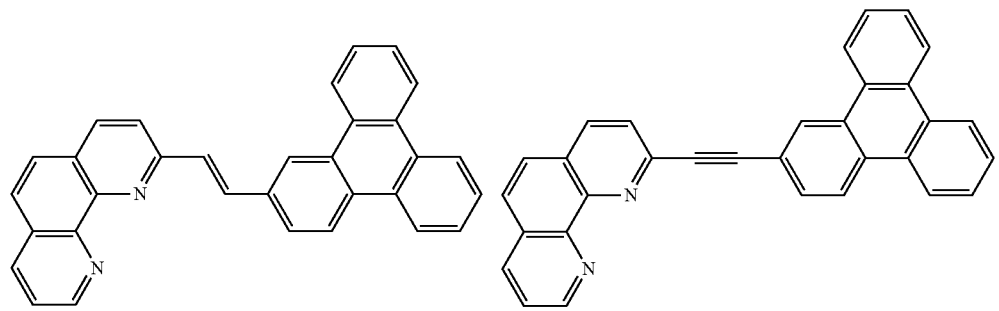
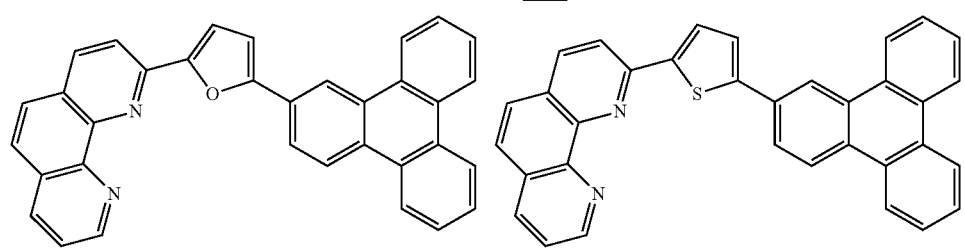
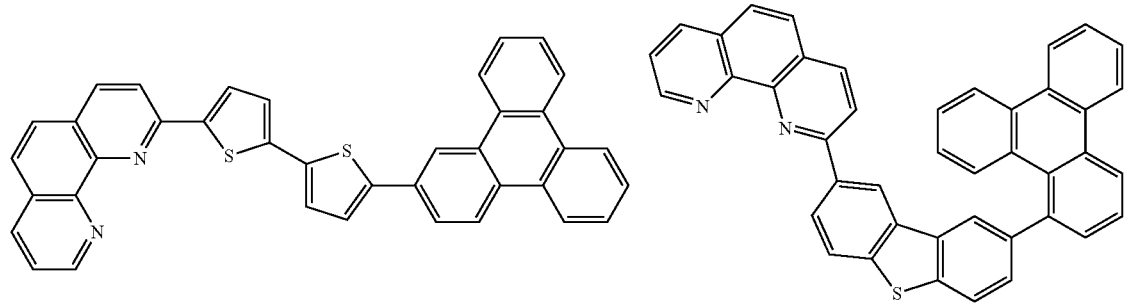
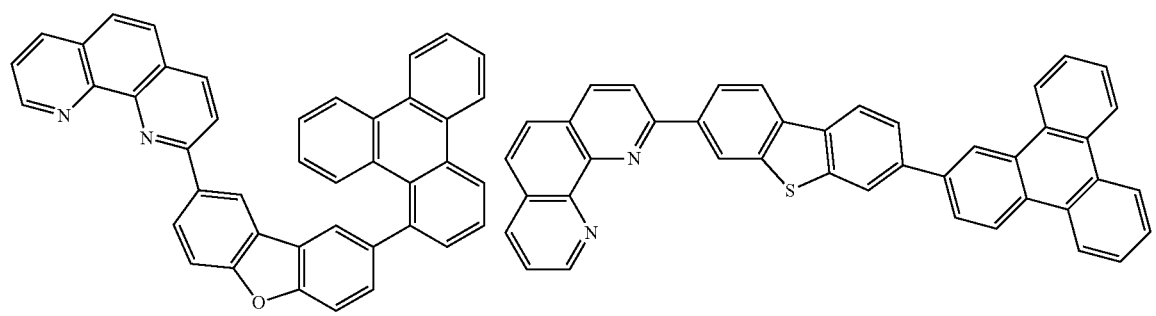
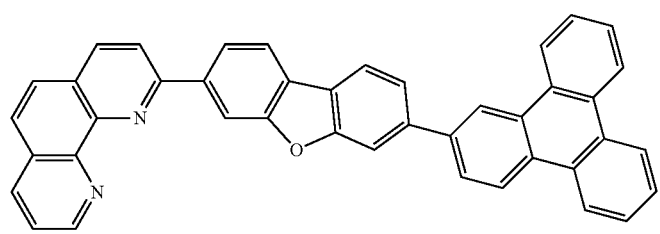

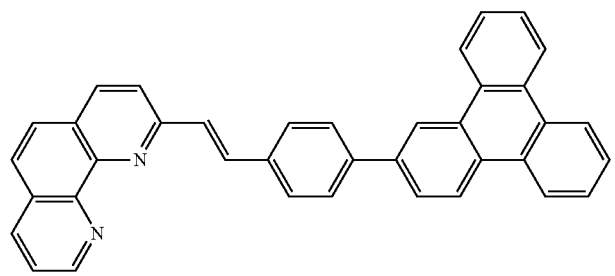
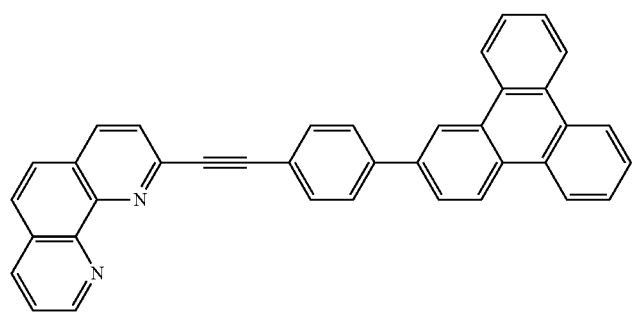
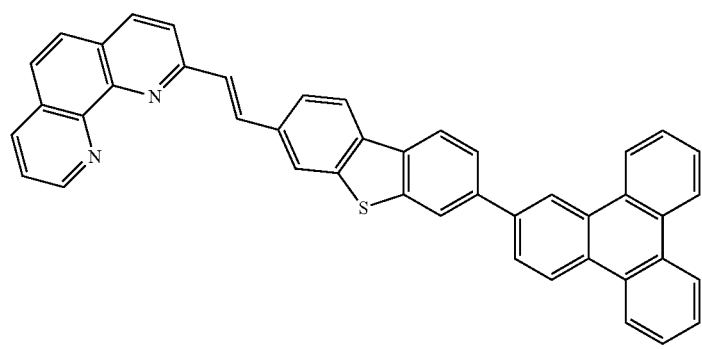
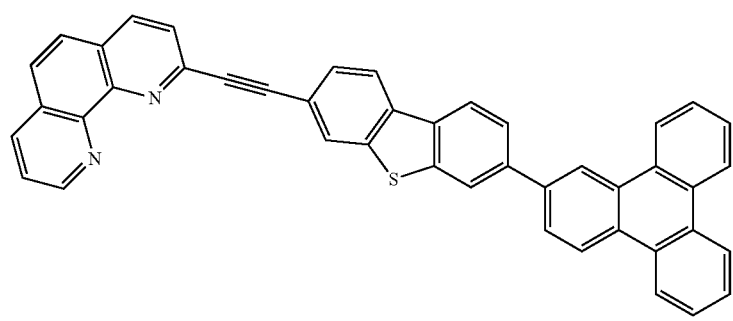
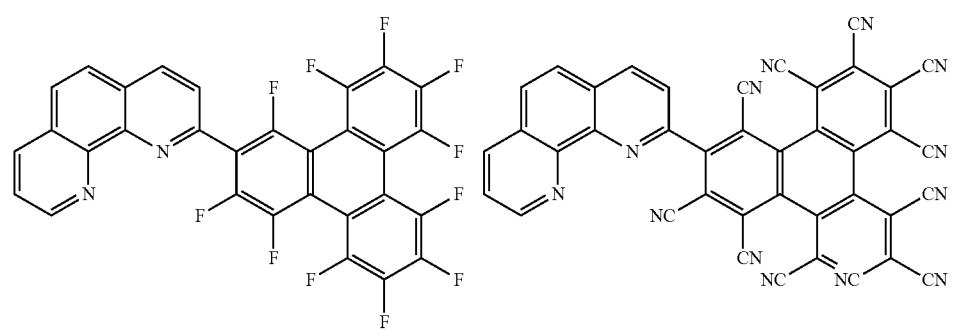

-continued
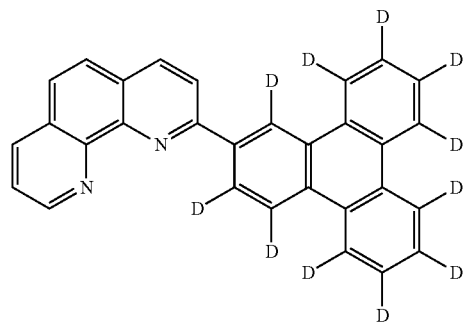 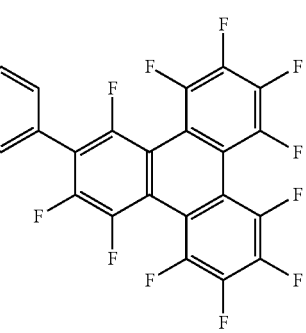
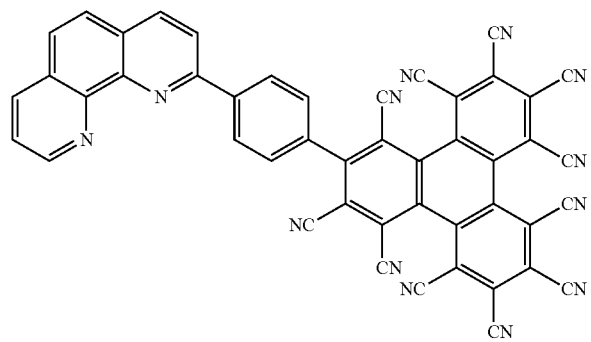 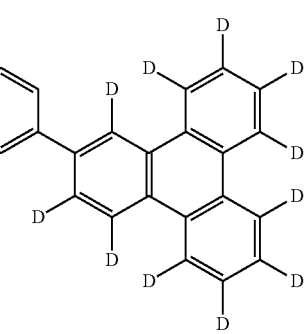
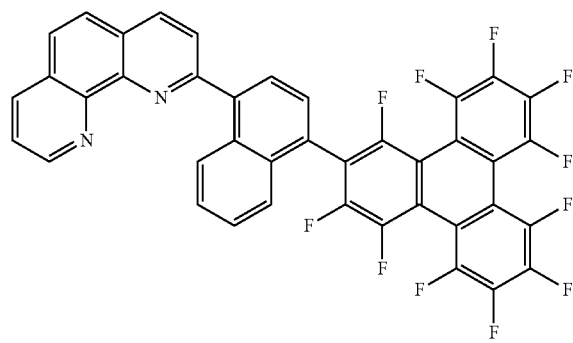 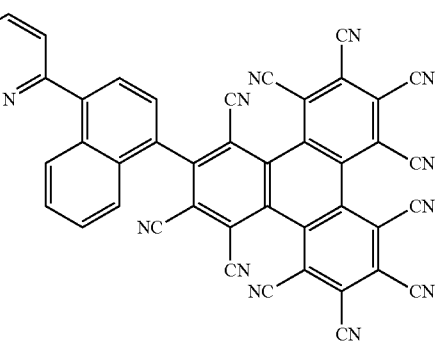
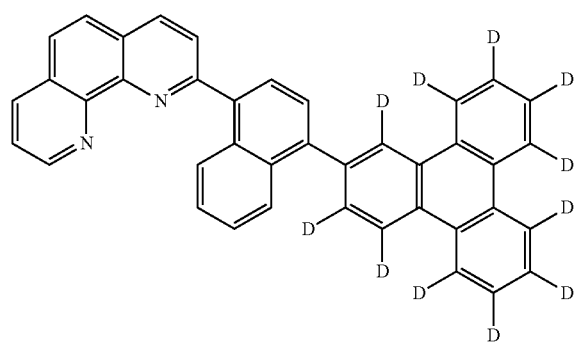 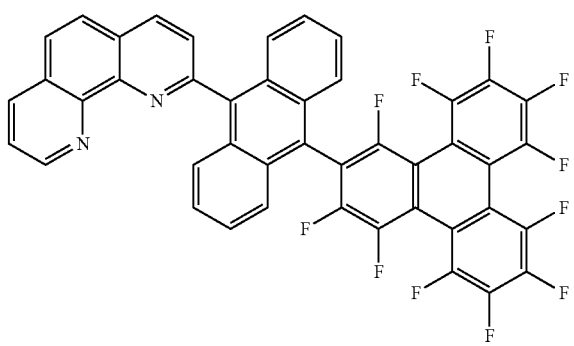 [SMILES: [2H]c1c([2H])c([2H])c2c(c1[2H])c1c([2H])c([2H])c([2H])c([2H])c1c1c([2H])c(-c3c4ccccc4c(-c4ccc5ccc6cccnc6c5n4)c4ccccc34)c([2H])c([2H])c21]

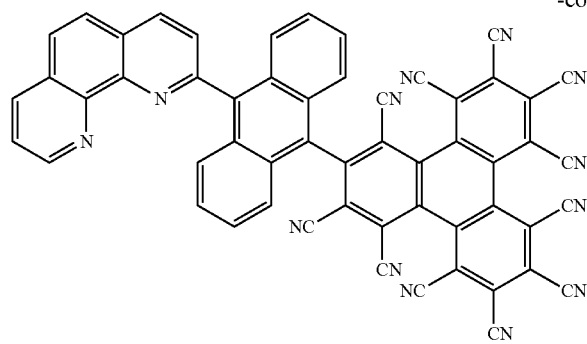
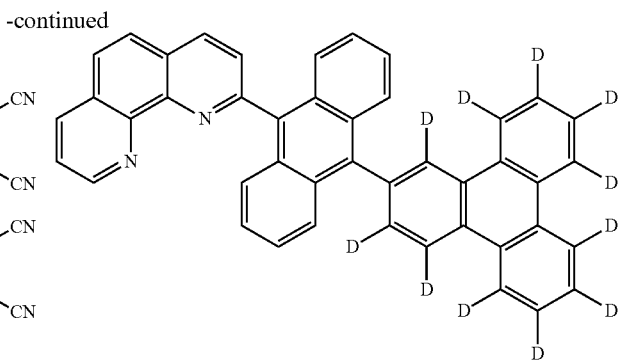

A compound of this disclosure may facilitate electron transport since it has high electron mobility by comprising a core having two electron-rich nitrogen (N) atoms. Moreover, the compound of this disclosure includes sp$^2$ hybrid orbitals of nitrogen (N) that are relatively rich in electrons, and the nitrogen binds to an alkali metal or alkali earth metal, i.e., a dopant for the N-type charge generation layer, thereby forming a gap state. This gap state may facilitate transfer of electrons from the N-type charge generation layer to the electron transport layer. Also, an unshared electron pair of nitrogen binds well to the alkali metal or alkali earth metal included in the N-type charge generation layer, so the alkali metal or alkali earth metal is not diffused into the P-type charge generation layer, thereby improving lifetime. Moreover, the compound of this disclosure includes a high-crystallinity functional group with a plate-like structure, which allows electrons to easily move through the crystalline structure, thereby improving electron mobility.

Accordingly, the use of a compound of this disclosure as the N-type charge generation layer may improve electron mobility, thereby reducing the operating voltage of the device and improving its efficiency. Also, the compound of this disclosure may prevent the dopant of the N-type charge generation layer from being diffused into the P-type charge generation layer, thereby improving the lifetime of the device.

The N-type charge generation layer 160N further comprises a dopant. The dopant may be one among an alkali metal, an alkali earth metal, an alkali metal compound, an alkali earth metal compound, an organic complex of alkali metals, or an organic complex of alkali earth metals.

The P-type charge generation layer 160P may be formed of a metal or a P-doped organic material. The metal may be one or more alloys among Al, Cu, Fe, Pb, Zn, Au, Pt, W, In, Mo, Ni, and Ti. A P-type dopant and host for the P-doped organic material may be the following materials. For example, the P-type dopant may be one material among F$_4$-TCNQ(2,3,5,6-tetrafluoro-7,7,8,8,-tetracyanoquinodimethane), a derivative of tetracyanoquinodimethane, iodine, FeCl$_3$, FeF$_3$, and SbCl$_5$. The host may be one material among NPB (N,N'-bis(naphthalene-1-yl)-N,N'-bis(phenyl)-benzidine), TPD(N,N'-bis-(3-methylphenyl)-N,N'-bis(phenyl)-benzidine), and TNB(N,N,N'N'-tetranaphthalenyl-benzidine).

The second light emitting part ST2 comprising a second hole transport layer 180, a second light emitting layer 190, a second electron transport layer 200, and an electron injection layer 210 is on the charge generation layer 160.

The second light emitting part ST2 comprises the second light emitting layer 190. The second light emitting layer 190 may emit light of red (R), green (G), blue (B), or yellow-green (YG), and may be formed of a phosphorescent material. In this exemplary embodiment, the second light emitting layer 190 may be a yellow-green light emitting layer. The second light emitting layer 190 may have a single layer structure of a yellow-green light emitting layer or green light emitting layer, or a multilayer structure formed of a yellow-green light emitting layer and a green light emitting layer. The second light emitting layer 190 comprises a yellow-green light emitting layer, a green light emitting layer, or a multilayer structure formed of a yellow-green light emitting layer and a green light emitting layer, of a yellow light emitting layer and a red light emitting layer, of a green light emitting layer and a red light emitting layer, or of a yellow-green light emitting layer and a red light emitting layer.

This exemplary embodiment will be described by taking as an example a single layer structure of a second light emitting layer 190 that emits yellow-green light. The second light emitting layer 190 may include, but is not limited to, at least one host of CBP(4,4'-bis(carbazol-9-yl)biphenyl) or BAlq(Bis(2-methyl-8-quinolinolato)-4-(phenylphenolato) aluminum) and a phosphorescent yellow-green dopant that emits yellow-green light.

The second light emitting part ST2 comprises the second hole transport layer 180 between the charge generation layer 160 and the second light emitting layer 190, and comprises the second electron transport layer 200 and the electron injection layer 210 on the second light emitting layer 190. The second hole transport layer 180 and the second electron transport layer 200 may have the same composition as or a different composition than the first hole transport layer 120 and the first electron transport layers 150 of the first light emitting part ST1, respectively.

Accordingly, the second light emitting part ST2 comprising the second hole transport layer 180, the second light emitting layer 190, the second electron transport layer 200, and the electron injection layer 210 is formed on the charge generation layer 160. The cathode 220 is provided on the second light emitting part ST2 to constitute the organic light emitting display device according to the first exemplary embodiment of the present disclosure.

As stated above, a compound of this disclosure may facilitate electron transport since it has high electron mobility by comprising a core having two electron-rich nitrogen (N) atoms. Moreover, the compound of this disclosure includes sp$^2$ hybrid orbitals of nitrogen (N) that are relatively rich in electrons, and the nitrogen binds to an alkali metal or alkali earth metal, i.e., a dopant for the N-type charge generation layer, thereby forming a gap state. This gap state may facilitate transfer of electrons from the N-type charge generation layer to the electron transport layer. Also, an unshared electron pair of nitrogen binds well to the alkali metal or alkali earth metal included in the N-type charge generation layer, so the alkali metal or alkali earth metal is not diffused into the P-type charge generation layer, thereby improving lifetime. Moreover, the compound of this disclosure includes a high-crystallinity functional group with a plate-like structure, which allows electrons to easily move through the crystalline structure, thereby improving electron mobility.

Accordingly, the use of a compound of this disclosure as the N-type charge generation layer may improve electron mobility, thereby reducing the operating voltage of the device and improving its efficiency. Also, the compound of this disclosure may prevent the dopant of the N-type charge generation layer from being diffused into the P-type charge generation layer, thereby improving the lifetime of the device.

Figure 2:
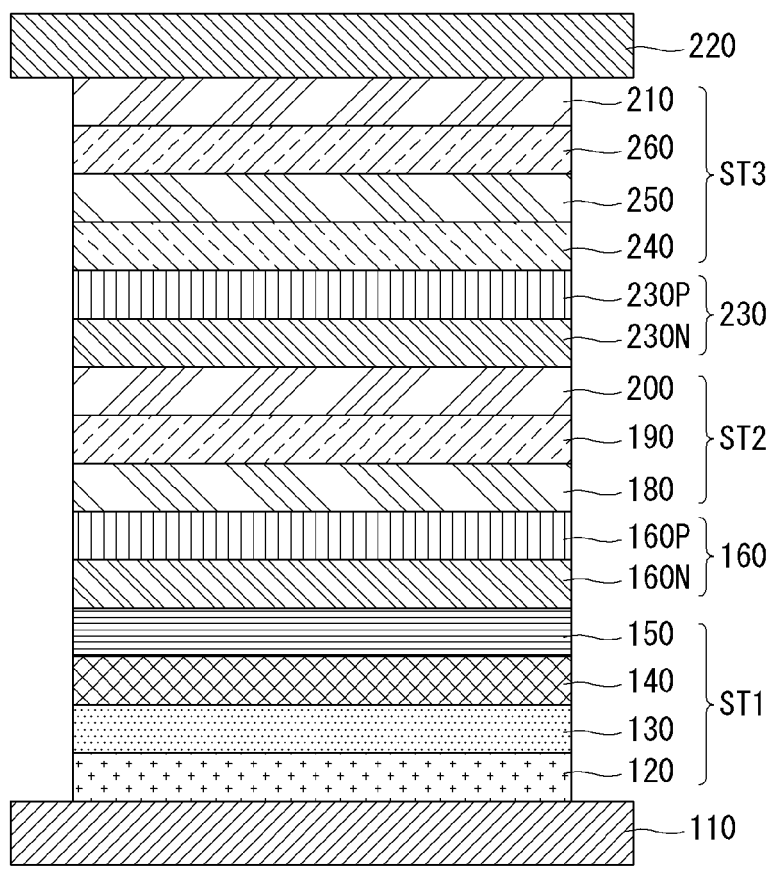
FIG. 2 is a view showing an organic light emitting display device according to a second exemplary embodiment of the present disclosure.

FIG. 2 is a view showing an organic light emitting display device according to a second exemplary embodiment of the present disclosure. The same elements as the first exemplary embodiment are denoted by the same reference numerals, so descriptions of these elements will be omitted below.

Referring to FIG. 2, an organic light emitting display device 100 of the present disclosure comprises a plurality of light emitting parts ST1, ST2, and ST3 between an anode 110 and a cathode 220, and a first charge generation layer 160 and a second charge generation layer 230 that are between the light emitting parts ST1, ST2, and ST3. Although this exemplary embodiment has been illustrated and described with an example where three light emitting parts are between the anode 110 and the cathode 220, the present disclosure is not limited to this example and four or more light emitting parts may be between the anode 110 and the cathode 220.

Among the light emitting parts, the first light emitting part ST1 comprises a first light emitting layer 140. The first light emitting layer 140 may emit light of red, green, or blue: for example, it may be a blue light emitting layer in this exemplary embodiment. The blue light emitting layer comprises one among a blue light emitting layer, a dark blue light emitting layer, and a sky blue light emitting layer. Alternatively, the first light emitting layer 140 may be formed of a blue light emitting layer and a red light emitting layer, a blue light emitting layer and a yellow-green light emitting layer, or a blue light emitting layer and a green light emitting layer.

The first light emitting part ST1 comprises a hole injection layer 120 and a first hole transport layer 130 that are between the anode 110 and the first light emitting layer 140, and a first electron transport layer 150 on the first light emitting layer 140. Accordingly, the first light emitting part ST1 comprising the hole injection layer 120, first hole transport layer 130, first light emitting layer 140, and first electron transport layer 150 is formed on the anode 110. The hole injection layer 120 may not be included in the elements of the first light emitting part ST1, depending on the structure or characteristics of the device.

The second light emitting part ST2 comprising a second light emitting layer 190 is on the first light emitting part ST1. The second light emitting layer 190 may emit light of red, green, blue, or yellow-green: for example, it may be a yellow-green light emitting layer in this exemplary embodiment. The second light emitting layer 190 may comprise a yellow-green light emitting layer, a green light emitting layer, or a multilayer structure formed of a yellow-green light emitting layer and a green light emitting layer, a yellow light emitting layer and a red light emitting layer, a green light emitting layer and a red light emitting layer, or a yellow-green light emitting layer and a red light emitting layer. The second light emitting part ST2 further comprises a second hole transport layer 180 on the first light emitting part ST1, and comprises a second electron transport layer 200 on the second light emitting layer 190. Accordingly, the second light emitting part ST2 comprising the second hole transport layer 180, the second light emitting layer 190, the and second electron transport layer 200 is formed on the first light emitting part ST1.

A first charge generation layer 160 is between the first light emitting part ST1 and the second light emitting part ST2. The first charge generation layer 160 is a PN-junction charge generation layer formed by joining an N-type charge generation layer 160N and a P-type charge generation layer 160P. The first charge generation layer 160 generates a charge, or injects the charge, i.e., electrons and holes, separately into the first and second light emitting layers 140 and 190.

The N-type charge generation layer 160N has the same composition as the above-described N-type charge generation layer 160N of the first exemplary embodiment. A compound of this disclosure included in the N-type charge generation layer 160N may facilitate electron transport since it has high electron mobility by comprising a core having two electron-rich nitrogen (N) atoms. Moreover, the compound of this disclosure includes $sp^2$ hybrid orbitals of nitrogen (N) that are relatively rich in electrons, and the nitrogen binds to an alkali metal or alkali earth metal, i.e., a dopant for the N-type charge generation layer, thereby forming a gap state. This gap state may facilitate transfer of electrons from the N-type charge generation layer to the electron transport layer. Also, an unshared electron pair of nitrogen binds well to the alkali metal or alkali earth metal included in the N-type charge generation layer, so the alkali metal or alkali earth metal is not diffused into the P-type charge generation layer, thereby improving lifetime. Moreover, the compound of this disclosure includes a high-crystallinity functional group with a plate-like structure, which allows electrons to easily move through the crystalline structure, thereby improving electron mobility. Accordingly, the use of a compound of this disclosure as the N-type charge generation layer may improve electron mobility, thereby reducing the operating voltage of the device and improving its efficiency. Also, the compound of this disclosure may prevent the dopant of the N-type charge generation layer from being diffused into the P-type charge generation layer, thereby improving the lifetime of the device.

The third light emitting part ST3 comprising a third light emitting layer 250 is on the second light emitting part ST2. The third light emitting layer 250 may emit light of red, green, or blue, and be formed of a fluorescent material. For example, it may be a blue light emitting layer in this exemplary embodiment. The blue light emitting layer comprises one among a blue light emitting layer, a dark blue light emitting layer, and a sky blue light emitting layer. Alternatively, the third light emitting layer 250 may be formed of a blue light emitting layer and a red light emitting layer, a blue light emitting layer and a yellow-green light emitting layer, or a blue light emitting layer and a green light emitting layer.

The third light emitting part ST3 further comprises a third hole transport layer 240 on the second light emitting part ST2, and a third electron transport layer 260 and an electron injection layer 210 that are on the third light emitting layer 250.

The second charge generation layer 230 is between the second light emitting part ST2 and the third light emitting part ST3. The second charge generation layer 230 is a PN junction charge generation layer formed by joining the N-type charge generation layer 230N and the P-type charge generation layer 230P. The second charge generation layer 230 generates a charge, or injects the charge, i.e., electrons and holes, separately into the second and third light emitting layers 190 and 250.

The N-type charge generation layer 230N has the same composition as the above-described N-type charge generation layer 160N of the first charge generation layer 160. A compound of this disclosure included in the N-type charge generation layer 160N may facilitate electron transport since it has high electron mobility by comprising a core having two electron-rich nitrogen (N) atoms. Moreover, the compound of this disclosure includes $sp^2$ hybrid orbitals of nitrogen (N) that are relatively rich in electrons, and the nitrogen binds to an alkali metal or alkali earth metal, i.e., a dopant for the N-type charge generation layer, thereby forming a gap state. This gap state may facilitate transfer of electrons from the N-type charge generation layer to the electron transport layer. Also, an unshared electron pair of nitrogen binds well to the alkali metal or alkali earth metal included in the N-type charge generation layer, so the alkali metal or alkali earth metal is not diffused into the P-type charge generation layer, thereby improving lifetime. Moreover, the compound of this disclosure includes a high-crystallinity functional group with a plate-like structure, which allows electrons to easily move through the crystalline structure, thereby improving electron mobility. Accordingly, the use of a compound of this disclosure as the N-type charge generation layer may improve electron mobility, thereby reducing the operating voltage of the device and improving its efficiency. Also, the compound of this disclosure may prevent the dopant of the N-type charge generation layer from being diffused into the P-type charge generation layer, thereby improving the lifetime of the device.

The cathode 220 is provided on the third light emitting part ST3 to constitute the organic light emitting display device according to the second exemplary embodiment of the present disclosure.

The above-described second exemplary embodiment of the present disclosure has disclosed that the N-type charge generation layer 160N of the first charge generation layer 160 and the N-type charge generation layer 230N of the second charge generation layer 230 comprise a compound of this disclosure. Alternatively, at least one between the N-type charge generation layer 160N of the first charge generation layer 160 and the N-type charge generation layer 230N of the second charge generation layer 230 may comprise the compound of this disclosure.

Organic light emitting displays using the organic light emitting display device according to the second exemplary embodiment of the present disclosure may include top emission displays, bottom emission displays, dual emission displays, and vehicle lighting. The vehicle lighting may include, but are not necessarily limited to, headlights, high beams, taillights, brake lights, and back-up lights. Moreover, organic light emitting displays using the organic light emitting display device according to the second exemplary embodiment of the present disclosure may be applied to mobile devices, monitors, TVs, etc. In addition, organic light emitting displays using the organic light emitting display device according to the second exemplary embodiment of the present disclosure may be applied to displays in which at least two of the first, second, and third light emitting layers emit light of the same color.

As stated above, a compound of this disclosure may facilitate electron transport since it has high electron mobility by comprising a core having two electron-rich nitrogen (N) atoms. Moreover, the compound of this disclosure includes $sp^2$ hybrid orbitals of nitrogen (N) that are relatively rich in electrons, and the nitrogen binds to an alkali metal or alkali earth metal, i.e., a dopant for the N-type charge generation layer, thereby forming a gap state. This gap state may facilitate transfer of electrons from the N-type charge generation layer to the electron transport layer.

Also, an unshared electron pair of nitrogen binds well to the alkali metal or alkali earth metal included in the N-type charge generation layer, so the alkali metal or alkali earth metal is not diffused into the P-type charge generation layer, thereby improving lifetime. Moreover, the compound of this disclosure includes a high-crystallinity functional group with a plate-like structure, which allows electrons to easily move through the crystalline structure, thereby improving electron mobility.

Accordingly, the use of a compound of this disclosure as the N-type charge generation layer may improve electron mobility, thereby reducing the operating voltage of the device and improving its efficiency. Also, the compound of this disclosure may prevent the dopant of the N-type charge generation layer from being diffused into the P-type charge generation layer, thereby improving the lifetime of the device.

Hereinafter, synthesis examples of electron transport compounds and charge generation compounds of the present disclosure will be described in detail. However, the following examples are only for illustration, and the present disclosure is not limited thereto.

1) Synthesis of Compound A

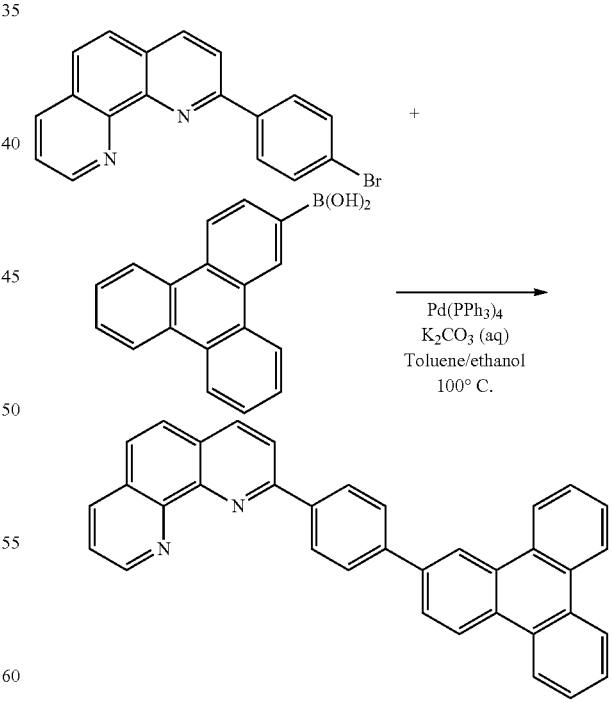

2-(4-bromophenyl)-1,10-phenanthroline (10 g, 29.83 mmol), triphenylenyl-2-boronic acid (9.74 g, 35.8 mmol), tetrakistriphenylphosphine palladium(0) (1.72 g, 1.49 mmol), 10 ml of 4M potassium carbonate solution, 200 ml of toluene, and 20 ml of ethanol were put under a nitrogen atmosphere, and then refluxed and stirred for 12 hours. After the reaction, 50 ml of distilled water was added, and the mixture was stirred for 3 hours, then vacuum-filtered, and then subjected to column chromatography for separation using methylene chloride/hexane as the eluent, followed by MC recrystallization, to obtain Compound A, i.e, 2-(4-(triphenylen-3-yl)phenyl)-1,10-phenanthroline (10 g, yield: 70%).

2) Synthesis of Compound B

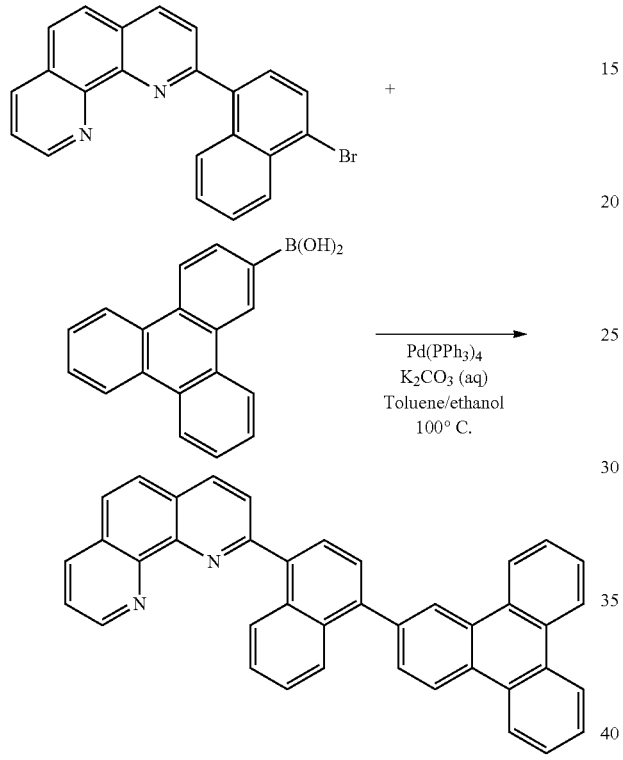

2-(1-bromonaphthalen-4-yl)-1,10-phenanthroline (10 g, 25.96 mmol), triphenylenyl-2-boronic acid (8.48 g, 31.15 mmol), tetrakistriphenylphosphine palladium(0) (1.5 g, 1.3 mmol), 10 ml of 4M potassium carbonate solution, 200 ml of toluene, and 20 ml of ethanol were put under a nitrogen atmosphere, and then refluxed and stirred for 12 hours. After the reaction, 50 ml of distilled water was added, and the mixture was stirred for 3 hours, then vacuum-filtered, and then subjected to column chromatography for separation using methylene chloride as the eluent, followed by MC recrystallization, to obtain Compound B, i.e, 2-(1-(triphenylen-3-yl)naphthalen-4-yl)-1,10-phenanthroline (8.3 g, yield: 60%).

3) Synthesis of Compound C

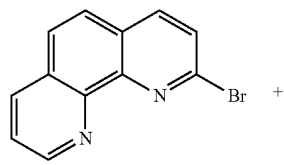

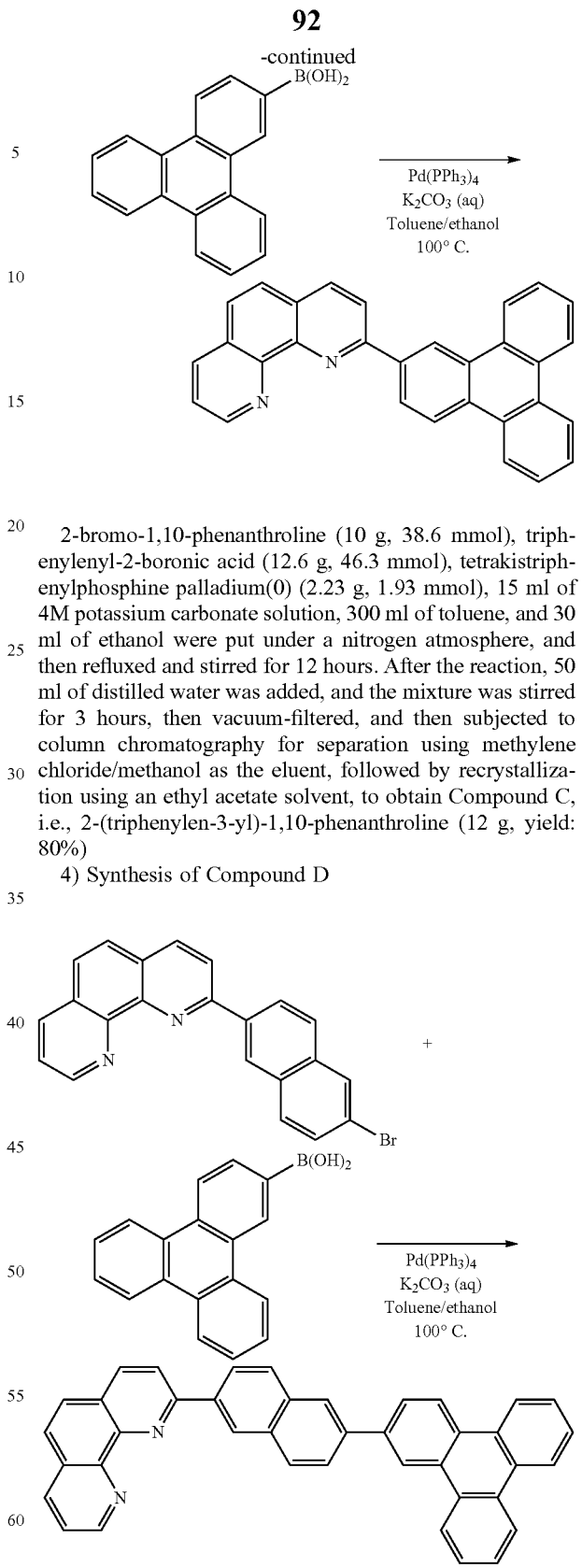

2-bromo-1,10-phenanthroline (10 g, 38.6 mmol), triphenylenyl-2-boronic acid (12.6 g, 46.3 mmol), tetrakistriphenylphosphine palladium(0) (2.23 g, 1.93 mmol), 15 ml of 4M potassium carbonate solution, 300 ml of toluene, and 30 ml of ethanol were put under a nitrogen atmosphere, and then refluxed and stirred for 12 hours. After the reaction, 50 ml of distilled water was added, and the mixture was stirred for 3 hours, then vacuum-filtered, and then subjected to column chromatography for separation using methylene chloride/methanol as the eluent, followed by recrystallization using an ethyl acetate solvent, to obtain Compound C, i.e., 2-(triphenylen-3-yl)-1,10-phenanthroline (12 g, yield: 80%)

4) Synthesis of Compound D 2-(2-bromonaphthalen-6-yl)-1,10-phenanthroline (20 g, 51.9 mmol), triphenylenyl-2-boronic acid (17 g, 32 mmol), tetrakistriphenylphosphine palladium(0) (3 g, 2.6 mmol), 10 ml of 4M potassium carbonate solution, 300 ml of toluene, and 30 ml of ethanol were put under a nitrogen atmosphere, and then refluxed and stirred for 12 hours. After the reaction, 50 ml of distilled water was added, and the mixture was stirred for 3 hours, then vacuum-filtered, and then subjected to column chromatography for separation using chloroform as the eluent, followed by MC recrystallization, to obtain Compound D, i.e., 2-(2-(triphenylen-2-yl)naphthalene-6-yl)-1,10-phenanthroline (15 g, yield: 55%)

Hereinafter, embodiments for the manufacture of an organic light emitting display device according to the present disclosure will be disclosed. However, the following materials for the N-type charge generation layer do not limit the scope of the present disclosure. The following Tests 1 through 3 were conducted under different process conditions for the manufacture of devices, and the devices of Comparative Examples and Embodiments used in the tests were manufactured under the same process condition. Therefore, in data analysis, it should be noted that the devices may exhibit different characteristics even if the same material was used as the N-type charge generation layer in Comparative Examples 1 to 3.

Test 1: Organic Light Emitting Display Device Comprising Compound A

Comparative Example 1

An organic light emitting display device was manufactured by forming, on a substrate, a first light emitting part comprising a hole injection layer, a first hole transport layer, a blue fluorescent light emitting layer, and a first electron transport layer, a charge generation layer comprising a N-type charge generation layer and a P-type charge generation layer, a second light emitting part comprising a second hole transport layer, a yellow-green phosphorescent light emitting layer, and a second electron transport layer, and a cathode. Here, the N-type charge generation layer was formed of a phenanthroline compound.

Embodiment 1

It has the same elements as the above-described Comparative Example 1, and the N-type charge generation layer was formed of Compound A.

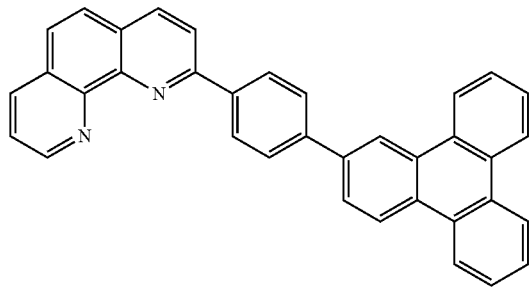 [SMILES: c1cnc2c(c1)ccc1ccc(-c3ccc(-c4ccc5c6ccccc6c6ccccc6c5c4)cc3)nc12]

The operating voltage, light emission efficiency, external quantum efficiency, chromaticity coordinates, and lifetime of the devices manufactured according to the above-described Comparative Example 1 and Embodiment 1 of the present disclosure were measured and shown in the following Table 1. (The devices operated at a current density of 10 mA/cm$^2$, lifetime T95 is white lifetime, which is the time it takes for the luminance to decrease to 95% of the initial luminance. The measurements taken in Embodiment 1 were expressed as a percentage relative to those taken in Comparative Example 1 corresponding to 100%).

Figure 3:
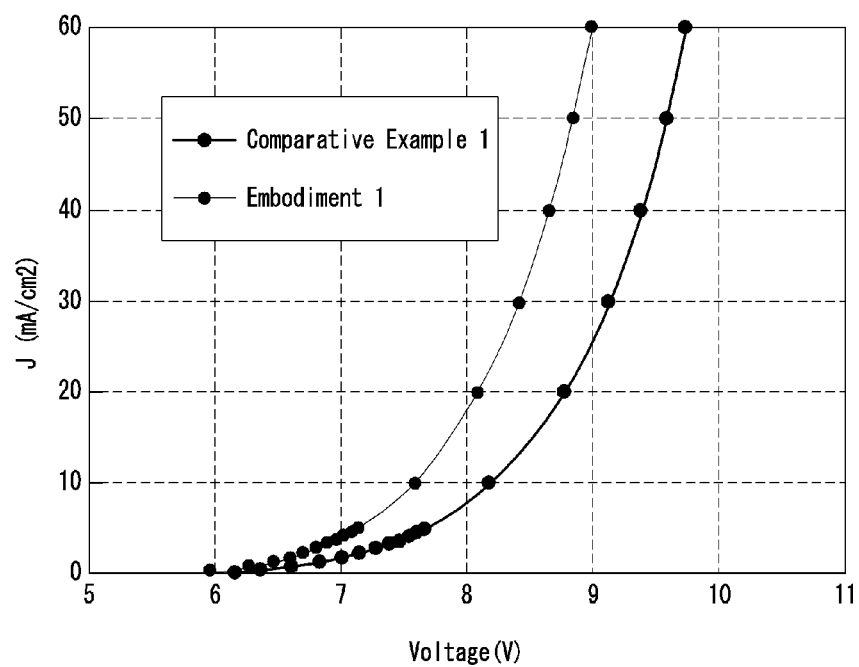
FIG. 3 is a graph of the current density vs. operating voltage of organic light emitting display devices according to Comparative Example 1 and Embodiment 1 of the present disclosure.
Figure 4:
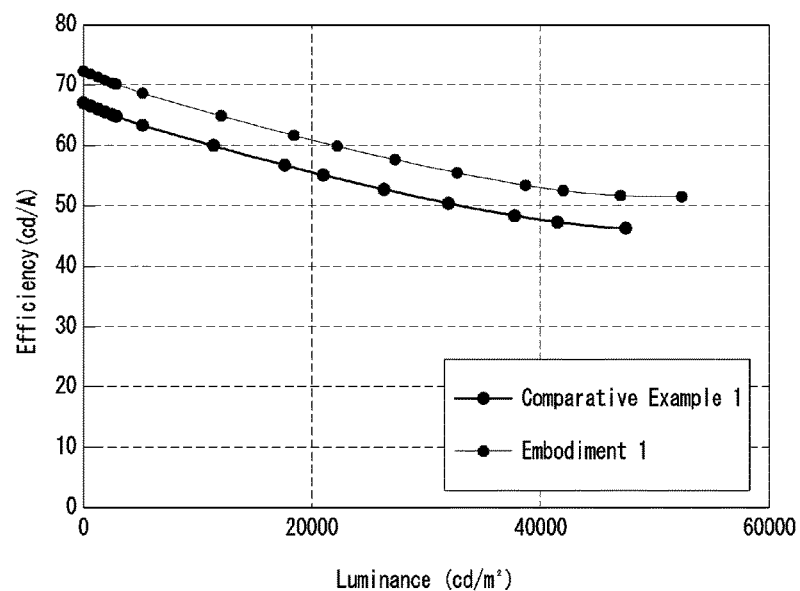
FIG. 4 is a graph of the light emission efficiency vs. luminance of organic light emitting display devices according to Comparative Example 1 and Embodiment 1 of the present disclosure.
Figure 5:
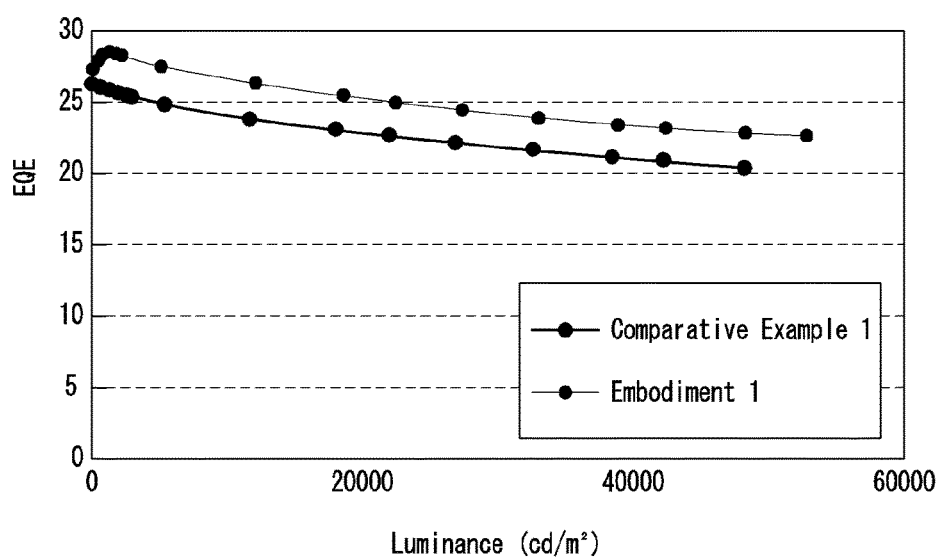
FIG. 5 is a graph of the external quantum efficiency vs. luminance of organic light emitting display devices according to Comparative Example 1 and Embodiment 1 of the present disclosure.
Figure 6:
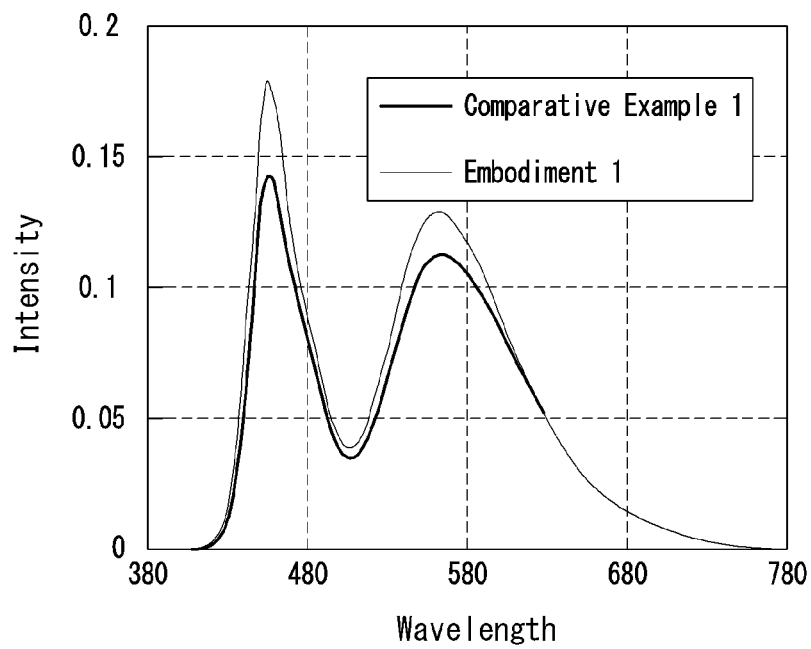
FIG. 6 is a graph of the light emission spectra of organic light emitting devise according to Comparative Example 1 and Embodiment 1 of the present disclosure.
Figure 7:
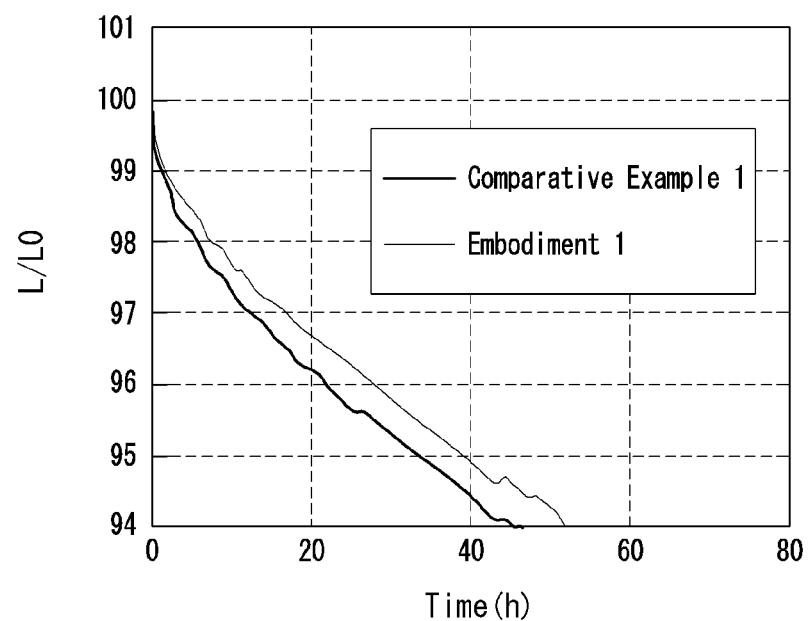
FIG. 7 is a graph of the rate of decrease in luminance over time of organic light emitting display devices according to Comparative Example 1 and Embodiment 1 of the present disclosure.

The current density vs. operating voltage of the organic light emitting display devices manufactured according to Comparative Example 1 and Embodiment 1 was shown in FIG. 3, the light emission efficiency vs. luminance was shown in FIG. 4, the external quantum efficiency vs. luminance was shown in FIG. 5, the light emission spectra were shown in FIG. 6, and the rate of decrease in luminance over time was shown in FIG. 7.

TABLE 1

| | Operating voltage | Light emission efficiency | External quantum efficiency | Chromaticity coordinates | | Lifetime (T95) |
|---|---|---|---|---|---|---|
| | | | | CIE_x | CIE_y | |
| Comparative Example 1 | 100 | 100 | 100 | 0.332 | 0.351 | 100 |
| Embodiment 1 | 93 | 112 | 111 | 0.321 | 0.342 | 172 |

Referring to Table 1, Embodiment 1 comprising Compound A of this disclosure showed similar chromaticity coordinate values, an about 7% decrease in operating voltage, an about 12% increase in light emission efficiency, an about 11% increase in external quantum efficiency, and an about 72% increase in lifetime, compared to Comparative Example 1 using a phenanthroline compound as the N-type charge generation layer.

Referring to FIG. 3, the operating voltage of the device according to Embodiment 1 of the present disclosure was lower than that of the device according to Comparative Example 1. Referring to FIG. 4, the light emission efficiency of the device according to Embodiment 1 of the present disclosure was higher than that of the device according to Comparative Example 1. Referring to FIG. 5, the external quantum efficiency of the device according to Embodiment 1 of the present disclosure was higher than that of the device according to Comparative Example 1. Referring to FIG. 6, the light emission intensity in blue and yellow-green wavelength regions of the device according to Embodiment 1 of the present disclosure was higher than that of the device according to Comparative Example 1. That is, the blue wavelength region may range from 440 nm to 480 nm, and the yellow-green wavelength region may range from 520 nm to 590 nm. Referring to FIG. 7, it was observed that it took a longer time for the device according to Embodiment 1 of the present disclosure to decrease to 95% of the initial luminance than the device according to Comparative Example 1, resulting in an improvement in lifetime.

Test 2: Organic Light Emitting display device Comprising Compound B

Comparative Example 2

It has the same elements as the above-described Comparative Example 1 to manufacture an organic light emitting display device.

Embodiment 2

It has the same elements as the above-described Comparative Example 1, and the N-type charge generation layer was formed of Compound B.

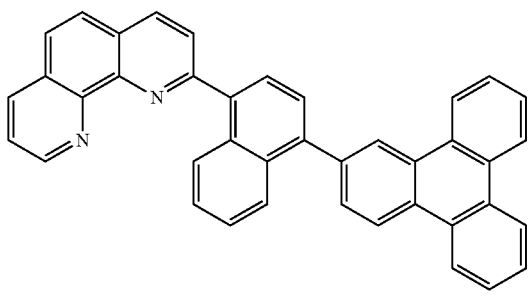 [SMILES: c1cnc2c(c1)ccc1ccc(-c3ccc(-c4ccc5c6ccccc6c6ccccc6c5c4)c4ccccc34)nc12]

The operating voltage, light emission efficiency, external quantum efficiency, chromaticity coordinates, and lifetime of the devices manufactured according to the above-described Comparative Example 2 and Embodiment 2 of the present disclosure were measured and shown in the following Table 2. The measurements taken in Embodiment 2 were expressed as a percentage relative to those taken in Comparative Example 2 corresponding to 100%.

Figure 8:
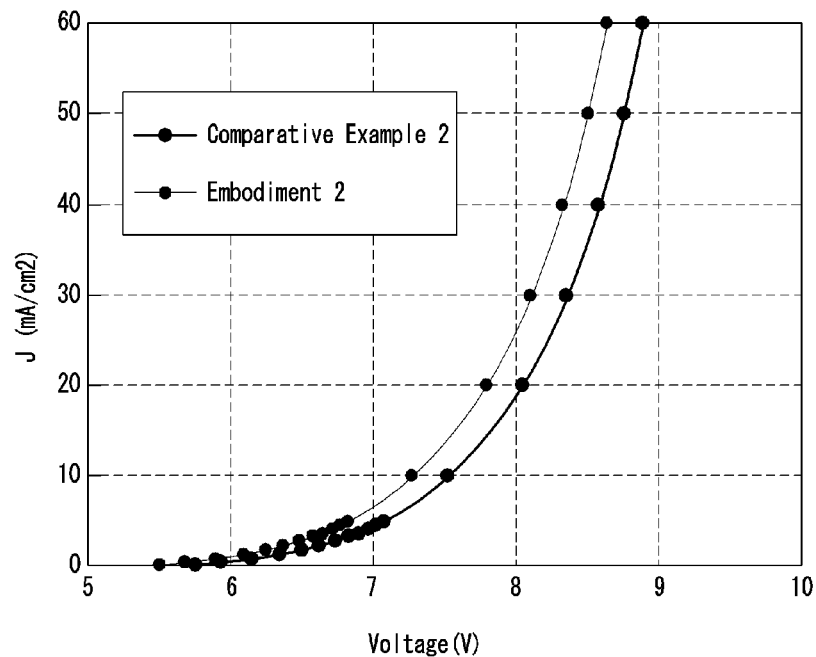
FIG. 8 is a graph of the current density vs. operating voltage of organic light emitting display devices according to Comparative Example 2 and Embodiment 2 of the present disclosure.
Figure 9:
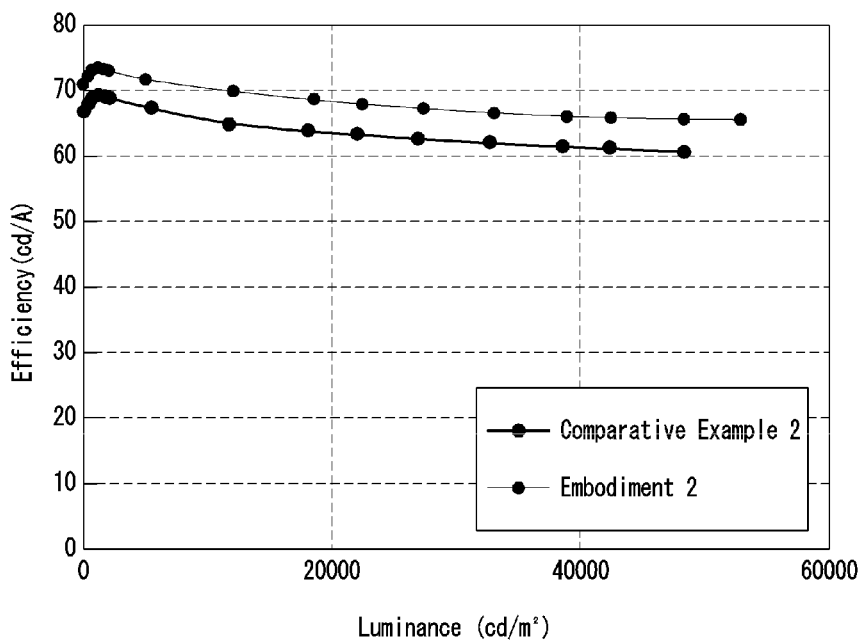
FIG. 9 is a graph of the light emission efficiency vs. luminance of organic light emitting display devices according to Comparative Example 2 and Embodiment 2 of the present disclosure.
Figure 10:
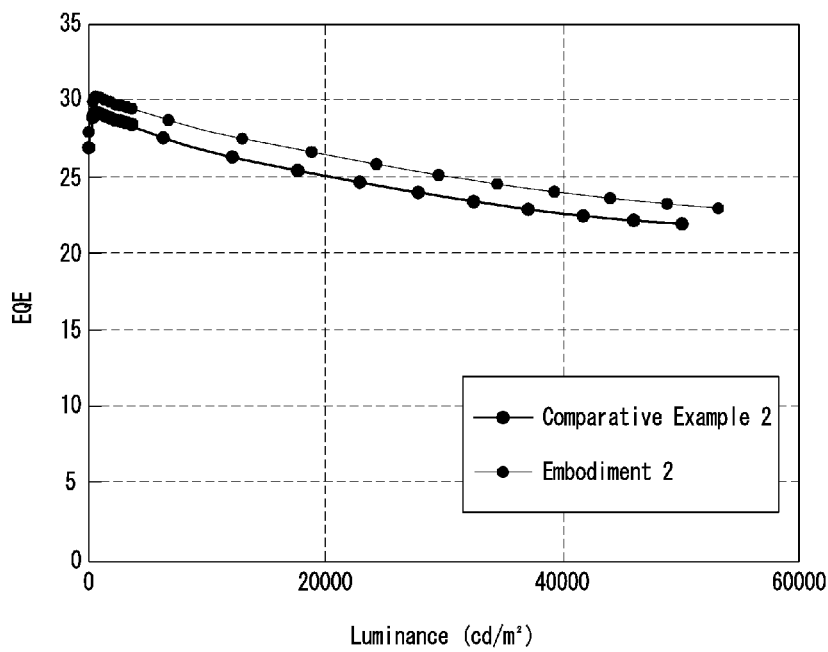
FIG. 10 is a graph of the external quantum efficiency vs. luminance of organic light emitting display devices according to Comparative Example 2 and Embodiment 2 of the present disclosure.
Figure 11:
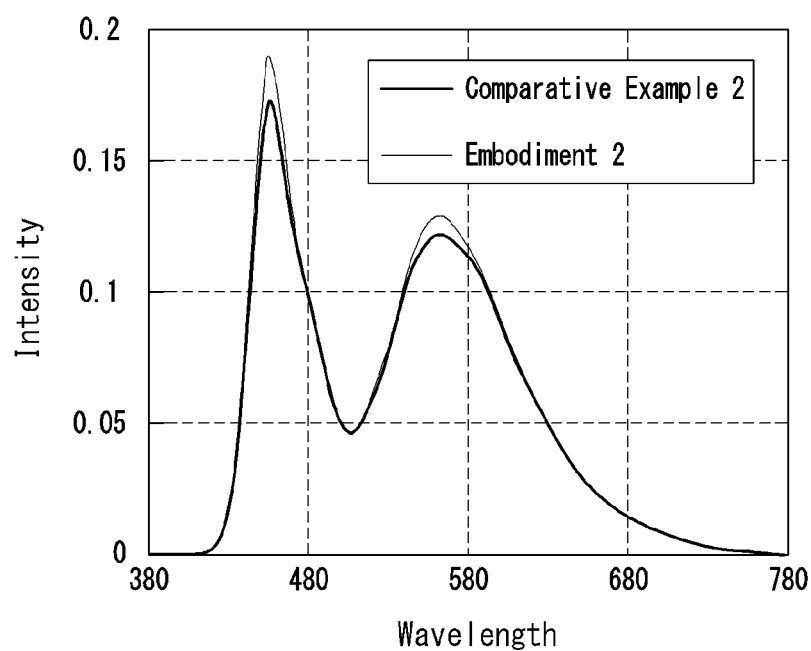
FIG. 11 is a graph of the light emission spectra of organic light emitting devise according to Comparative Example 2 and Embodiment 2 of the present disclosure.
Figure 12:
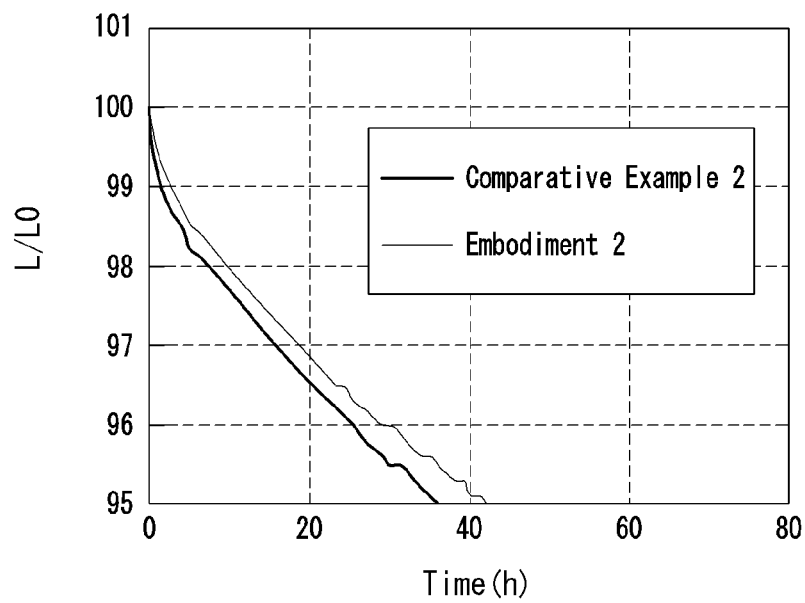
FIG. 12 is a graph of the rate of decrease in luminance over time of organic light emitting display devices according to Comparative Example 2 and Embodiment 2 of the present disclosure.

The current density vs. operating voltage of the organic light emitting display devices manufactured according to Comparative Example 2 and Embodiment 2 was shown in FIG. 8, the light emission efficiency vs. luminance was shown in FIG. 9, the external quantum efficiency vs. luminance was shown in FIG. 10, the light emission spectra were shown in FIG. 11, and the rate of decrease in luminance over time was shown in FIG. 12.

TABLE 2

| | Operating voltage | Light emission efficiency | External quantum efficiency | Chromaticity coordinates | | Lifetime (T95) |
|---|---|---|---|---|---|---|
| | | | | CIE_x | CIE_y | |
| Comparative Example 2 | 100 | 100 | 100 | 0.315 | 0.341 | 100 |
| Embodiment 2 | 97 | 105 | 104 | 0.313 | 0.339 | 117 |

Referring to Table 2, Embodiment 2 comprising Compound B of this disclosure showed similar chromaticity coordinate values, an about 3% decrease in operating voltage, an about 5% increase in light emission efficiency, an about 4% increase in external quantum efficiency, and an about 17% increase in lifetime, compared to Comparative Example 2 using a phenanthroline compound as the N-type charge generation layer.

Referring to FIG. 8, the operating voltage of the device according to Embodiment 2 of the present disclosure was lower than that of the device according to Comparative Example 2. Referring to FIG. 9, the light emission efficiency of the device according to Embodiment 2 of the present disclosure was higher than that of the device according to Comparative Example 2. Referring to FIG. 10, the external quantum efficiency of the device according to Embodiment 2 of the present disclosure was higher than that of the device according to Comparative Example 2. Referring to FIG. 11, the light emission intensity in blue and yellow-green wavelength regions of the device according to Embodiment 2 of the present disclosure was higher than that of the device according to Comparative Example 2. That is, the blue wavelength region may range from 440 nm to 480 nm, and the yellow-green wavelength region may range from 520 nm to 590 nm. Referring to FIG. 12, it was observed that it took a longer time for the device according to Embodiment 2 of the present disclosure to decrease to 95% of the initial luminance than the device according to Comparative Example 2, resulting in an improvement in lifetime.

Test 3: Organic Light Emitting display device Comprising Compound C

Comparative Example 3

It has the same elements as the above-described Comparative Example 1 to manufacture an organic light emitting display device.

Embodiment 3

It has the same elements as the above-described Comparative Example 1, and the N-type charge generation layer was formed of Compound C.

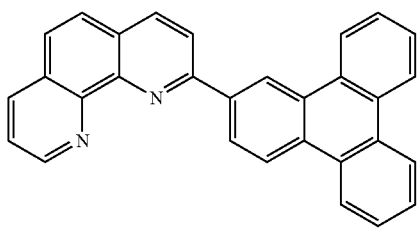 [SMILES: c1cnc2c(c1)ccc1ccc(-c3ccc4c5ccccc5c5ccccc5c4c3)nc12]

The operating voltage, light emission efficiency, external quantum efficiency, chromaticity coordinates, and lifetime of the devices manufactured according to the above-described Comparative Example 3 and Embodiment 3 of the present disclosure were measured and shown in the following Table 3. The measurements taken in Embodiment 3 were expressed as a percentage relative to those taken in Comparative Example 3 corresponding to 100%.

Figure 13:
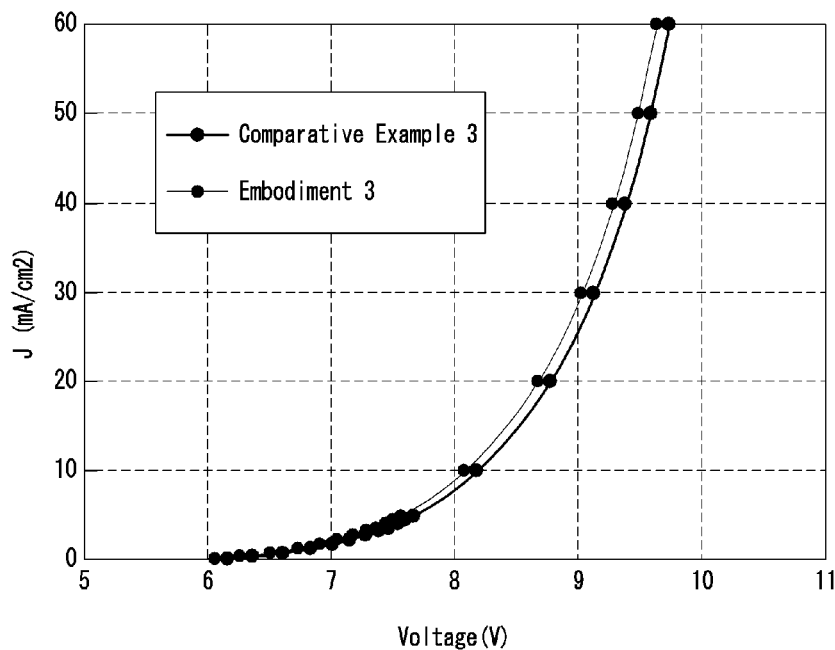
FIG. 13 is a graph of the current density vs. operating voltage of organic light emitting display devices according to Comparative Example 3 and Embodiment 3 of the present disclosure.
Figure 14:
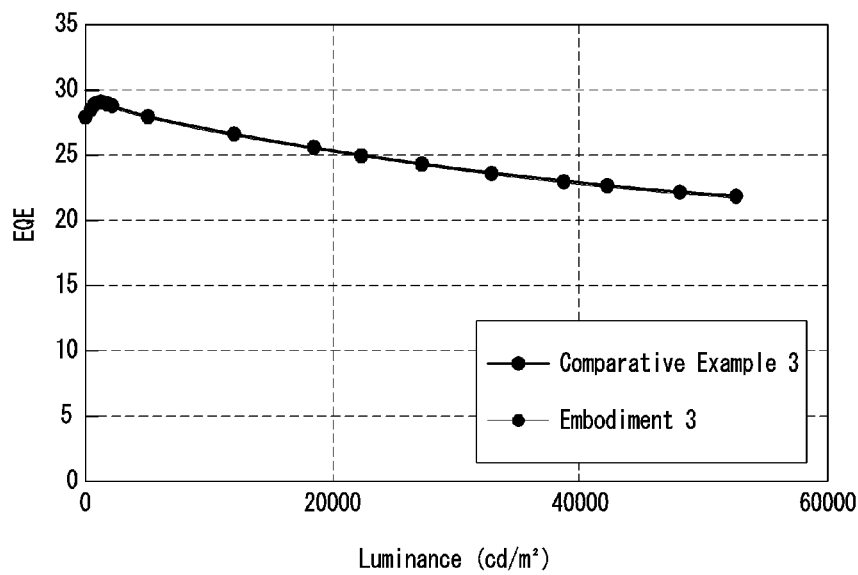
FIG. 14 is a graph of the external quantum efficiency vs. luminance of organic light emitting display devices according to Comparative Example 3 and Embodiment 3 of the present disclosure.
Figure 15:
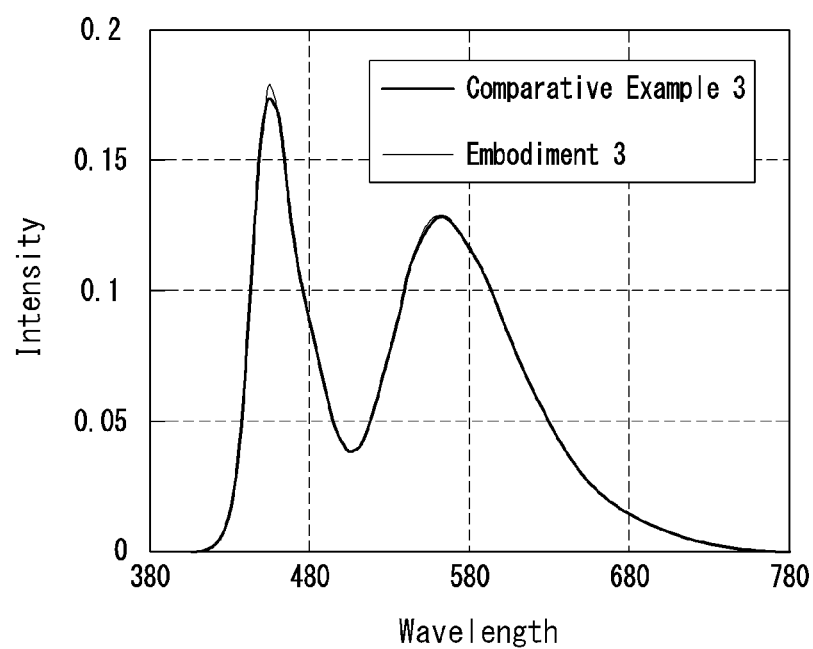
FIG. 15 is a graph of the light emission spectra of organic light emitting devise according to Comparative Example 3 and Embodiment 3 of the present disclosure.
Figure 16:
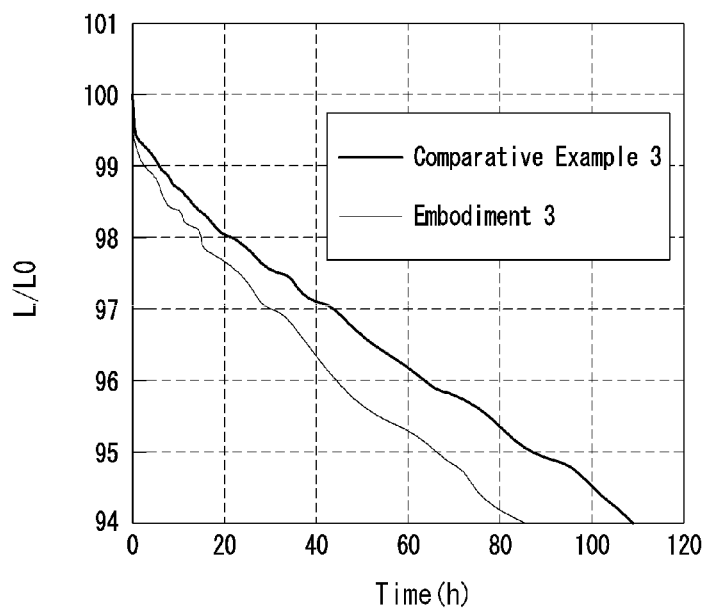
FIG. 16 is a graph of the rate of decrease in luminance over time of organic light emitting display devices according to Comparative Example 3 and Embodiment 3 of the present disclosure.

The current density vs. operating voltage of the organic light emitting display devices manufactured according to Comparative Example 3 and Embodiment 3 was shown in FIG. 13, the external quantum efficiency vs. luminance was shown in FIG. 14, the light emission spectra were shown in FIG. 15, and the rate of decrease in luminance over time was shown in FIG. 16.

TABLE 3

| | Operating voltage | Light emission efficiency | External quantum efficiency | Chromaticity coordinates | | Lifetime (T95) |
|---|---|---|---|---|---|---|
| | | | | CIE_x | CIE_y | |
| Comparative Example 3 | 100 | 100 | 100 | 0.321 | 0.336 | 100 |
| Embodiment 3 | 101 | 99 | 99 | 0.323 | 0.336 | 140 |

Referring to Table 3, Embodiment 3 comprising Compound C of this disclosure showed similar chromaticity coordinate values, an about 1% decrease in operating voltage, an about 1% increase in light emission efficiency, an about 1% increase in external quantum efficiency, and an about 40% increase in lifetime, compared to Comparative Example 3 using a phenanthroline compound as the N-type charge generation layer.

Referring to FIG. 13, the operating voltage of the device according to Embodiment 3 of the present disclosure was almost similar to that of the device according to Comparative Example 3. Referring to FIG. 14, the external quantum efficiency of the device according to Embodiment 3 of the present disclosure was almost similar to that of the device according to Comparative Example 3. Referring to FIG. 15, the light emission intensity in a yellow-green wavelength region of the device according to Embodiment 3 of the present disclosure was almost similar to that of the device according to Comparative Example 3, and the light emission intensity in a blue wavelength region of the device according to Embodiment 3 of the present disclosure was slightly higher than that of the device according to Comparative Example 3. That is, the blue wavelength region may range from 440 nm to 480 nm, and the yellow-green wavelength region may range from 520 nm to 590 nm. Referring to FIG. 16, it was observed that it took a longer time for the device according to Embodiment 3 of the present disclosure to decrease to 95% of the initial luminance than the device according to Comparative Example 3, resulting in an improvement in lifetime.

Test 4: Organic Light Emitting display device Comprising Compound D

Comparative Example 4

It has the same elements as the above-described Comparative Example 1 to manufacture an organic light emitting display device.

Embodiment 4

It has the same elements as the above-described Comparative Example 1, and the N-type charge generation layer was formed of Compound D.

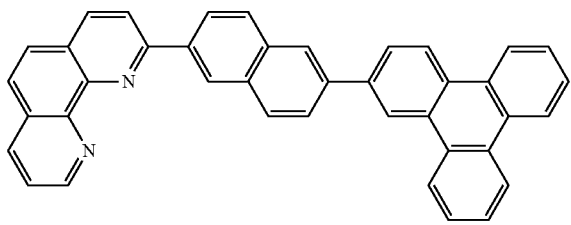 [SMILES: c1cnc2c(c1)ccc1ccc(-c3ccc4cc(-c5ccc6c7ccccc7c7ccccc7c6c5)ccc4c3)nc12]

The operating voltage, light emission efficiency, external quantum efficiency, chromaticity coordinates, and lifetime of the devices manufactured according to the above-described Comparative Example 4 and Embodiment 4 of the present disclosure were measured and shown in the following Table 4. The measurements taken in Embodiment 4 were expressed as a percentage relative to those taken in Comparative Example 4 corresponding to 100%.

Figure 17:
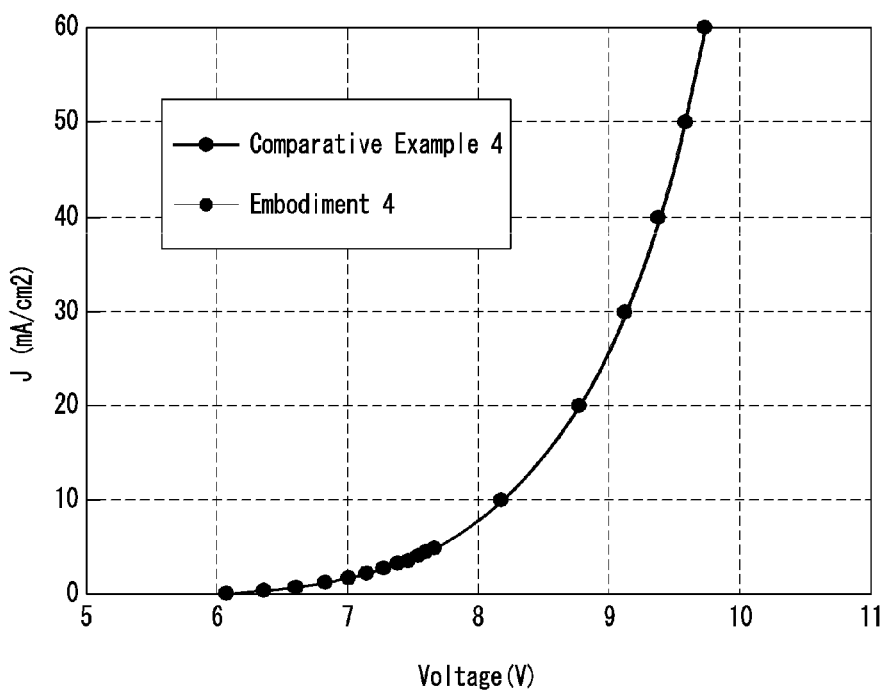
FIG. 17 is a graph of the current density vs. operating voltage of organic light emitting display devices according to Comparative Example 4 and Embodiment 4 of the present disclosure.
Figure 18:
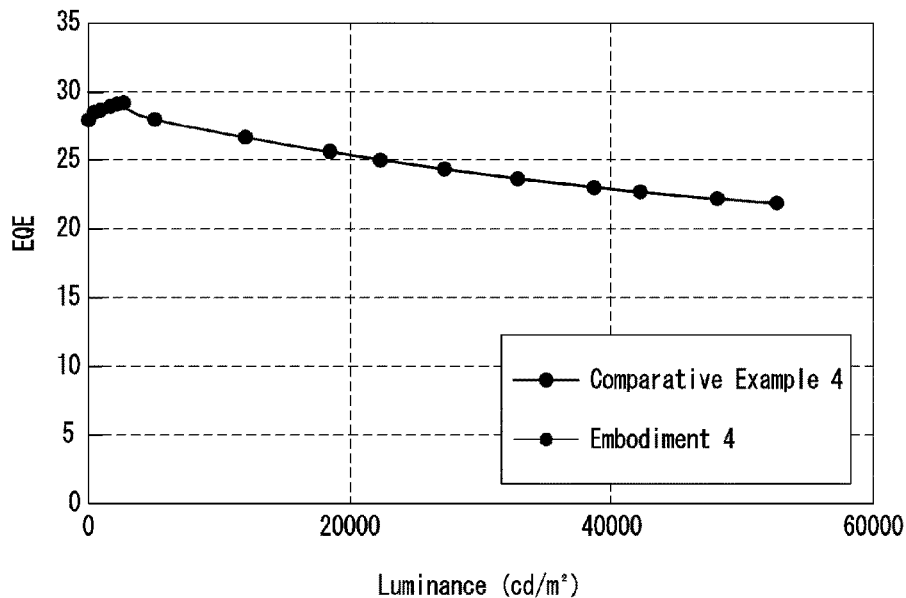
FIG. 18 is a graph of the external quantum efficiency vs. luminance of organic light emitting display devices according to Comparative Example 4 and Embodiment 4 of the present disclosure.
Figure 19:
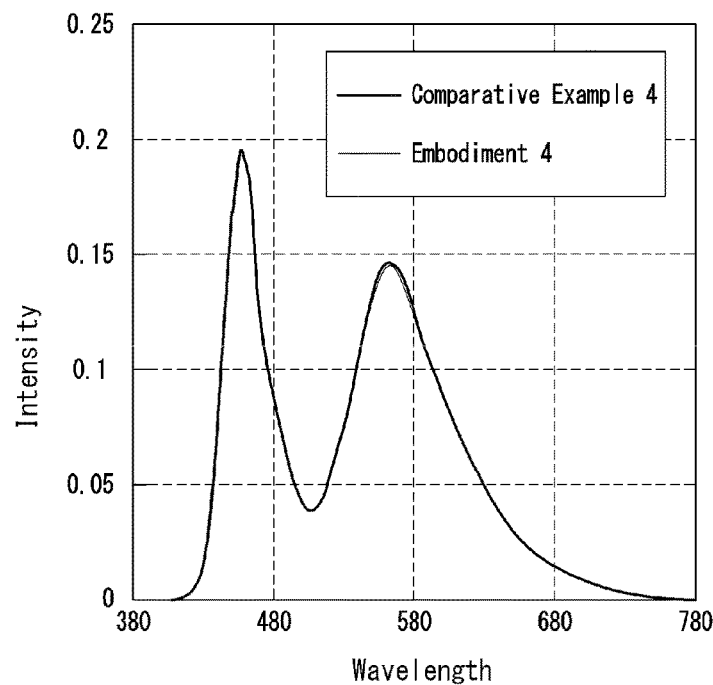
FIG. 19 is a graph of the light emission spectra of organic light emitting devise according to Comparative Example 4 and Embodiment 4 of the present disclosure.
Figure 20:
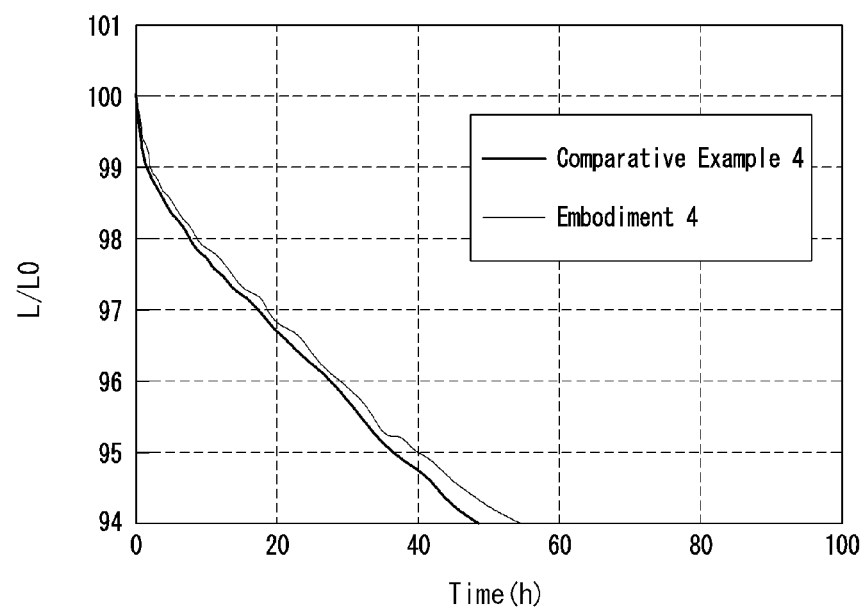
FIG. 20 is a graph of the rate of decrease in luminance over time of organic light emitting display devices according to Comparative Example 4 and Embodiment 4 of the present disclosure.

The current density vs. operating voltage of the organic light emitting display devices manufactured according to Comparative Example 4 and Embodiment 4 was shown in FIG. 17, the external quantum efficiency vs. luminance was shown in FIG. 18, the light emission spectra were shown in FIG. 19, and the rate of decrease in luminance over time was shown in FIG. 20.

TABLE 4

| | Operating voltage | Light emission efficiency | External quantum efficiency | Chromaticity coordinates | | Life-time |
|---|---|---|---|---|---|---|
| | | | | CIE_x | CIE_y | (T95) |
| Comparative Example 4 | 100 | 100 | 100 | 0.320 | 0.335 | 100 |
| Embodiment 4 | 100 | 100 | 100 | 0.320 | 0.336 | 112 |

Referring to Table 4, Embodiment 4 comprising Compound D of this disclosure showed similar chromaticity coordinate values, the same operating voltage, the same light emission efficiency, the same external quantum efficiency, and an about 12% increase in lifetime, compared to Comparative Example 4 using a phenanthroline compound as the N-type charge generation layer.

Referring to FIG. 17, the operating voltage of the device according to Embodiment 4 of the present disclosure was the same as the device according to Comparative Example 4. Referring to FIG. 18, the external quantum efficiency of the device according to Embodiment 4 of the present disclosure was the same as the device according to Comparative Example 4. Referring to FIG. 19, the light emission intensity in blue and yellow-green wavelength regions of the device according to Embodiment 4 of the present disclosure was almost similar to that of the device according to Comparative Example 4. Referring to FIG. 20, it was observed that it took a longer time for the device according to Embodiment 4 of the present disclosure to decrease to 95% of the initial luminance than the device according to Comparative Example 4, resulting in an improvement in lifetime.

From the results of the above-described Tests 1 through 4, it can be found out that the organic light emitting display devices according to the embodiments using a compound of this disclosure as the N-type charge generation layer showed at least similar operating voltage, light emission efficiency, external quantum efficiency, and chromaticity coordinates to those of the organic light emitting display devices according to Comparative Examples 1 through 4 using a phenanthroline compound as the N-type charge generation layer and showed a significant improvement, especially in lifetime.

As stated above, a compound of this disclosure may facilitate electron transport since it has high electron mobility by comprising a core having two electron-rich nitrogen (N) atoms. Moreover, the compound of this disclosure includes $sp^2$ hybrid orbitals of nitrogen (N) that are relatively rich in electrons, and the nitrogen binds to an alkali metal or alkali earth metal, i.e., a dopant for the N-type charge generation layer, thereby forming a gap state. This gap state may facilitate transfer of electrons from the N-type charge generation layer to the electron transport layer.

Also, an unshared electron pair of nitrogen binds well to the alkali metal or alkali earth metal included in the N-type charge generation layer, so the alkali metal or alkali earth metal is not diffused into the P-type charge generation layer, thereby improving lifetime. Moreover, the compound of this disclosure includes a high-crystallinity functional group with a plate-like structure, which allows electrons to easily move through the crystalline structure, thereby improving electron mobility.

Accordingly, the use of a compound of this disclosure as the N-type charge generation layer may improve electron mobility, thereby reducing the operating voltage of the device and improving its efficiency. Also, the compound of this disclosure may prevent the dopant of the N-type charge generation layer from being diffused into the P-type charge generation layer, thereby improving the lifetime of the device.

It will be apparent to those skilled in the art that various modifications and variations can be made in the organic light emitting display device of the present invention without departing from the spirit or scope of the invention. Thus, it is intended that the present invention cover the modifications and variations of this invention provided they come within the scope of the appended claims and their equivalents.

What is claimed is:

1. An organic light emitting display device, comprising:
at least two or more light emitting parts each comprising a light emitting layer and an electron transport layer; and
a charge generation layer between the at least two or more light emitting parts, wherein the charge generation layer comprises a compound that includes a core with two nitrogen atoms and a functional group having a crystallinity,
wherein the charge generation layer comprises a P-type charge generation layer and an N-type charge generation layer, and the compound is included in the N-type charge generation layer,
wherein the compound is represented by the following Chemical Formula 1:

[Chemical Formula 1]

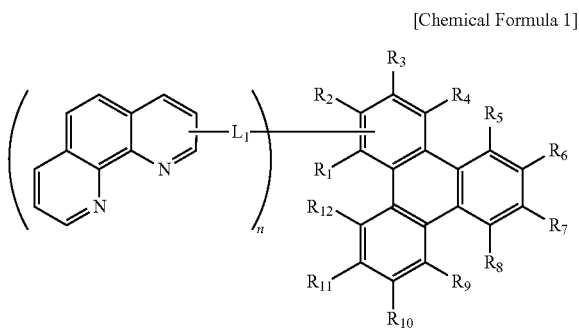

wherein:
$L_1$ includes one among a substituted or unsubstituted arylene group with 6 to 60 carbon atoms, a substituted or unsubstituted heteroarylene group with 3 to 60 carbon atoms, and a single bond;

one among $R_1$ to $R_{12}$ binds to $L_1$, and the others among $R_1$ to $R_{12}$ that do not bind to $L_1$ include independently one among a substituted or unsubstituted aryl group with 5 to 30 carbon atoms, a substituted or unsubstituted heteroaryl group with 4 to 30 carbon atoms, a halogen group, a nitrile group, heavy hydrogen, and hydrogen; and n includes one among 1 and 2.

2. The organic light emitting display device of claim 1, wherein the N-type charge generation layer further comprises a dopant, and the dopant includes one among an alkali metal, an alkali earth metal, an alkali metal compound, an alkali earth metal compound, an organic complex of alkali metals, or an organic complex of alkali earth metals.

3. The organic light emitting display device of claim 2, wherein the nitrogen atoms included in the core of the compound bind to the dopant to prevent the dopant from being diffused into another layer adjacent to the charge generation layer.

4. The organic light emitting display device of claim 1, wherein one of the at least two or more light emitting parts comprises a blue light emitting part, and the another one of the at least two or more light emitting parts is a yellow-green light emitting part.

5. The organic light emitting display device of claim 1, wherein the compound represented by Chemical Formula 1 includes one among the following compounds:

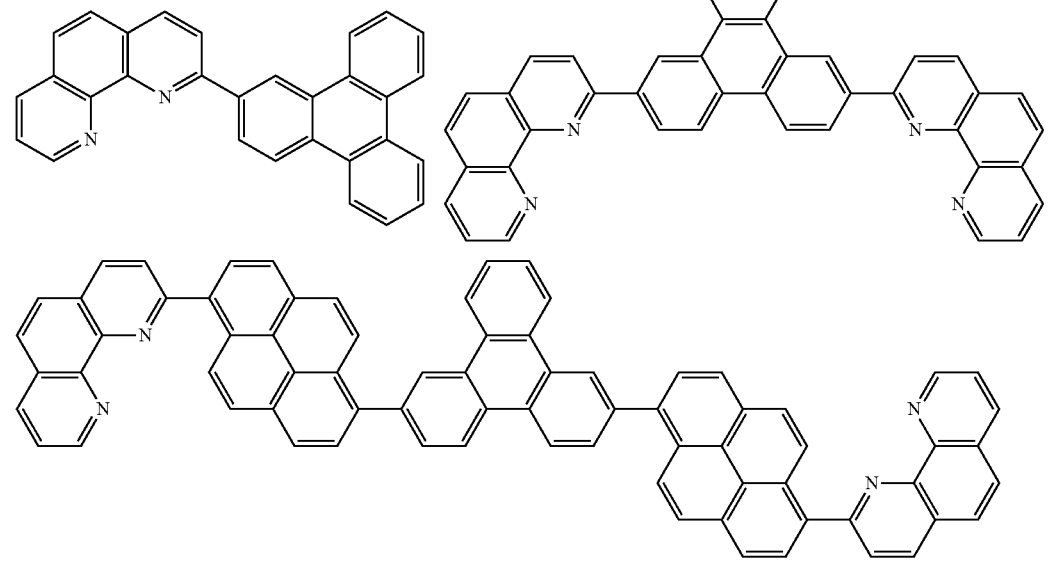

101
102
-continued
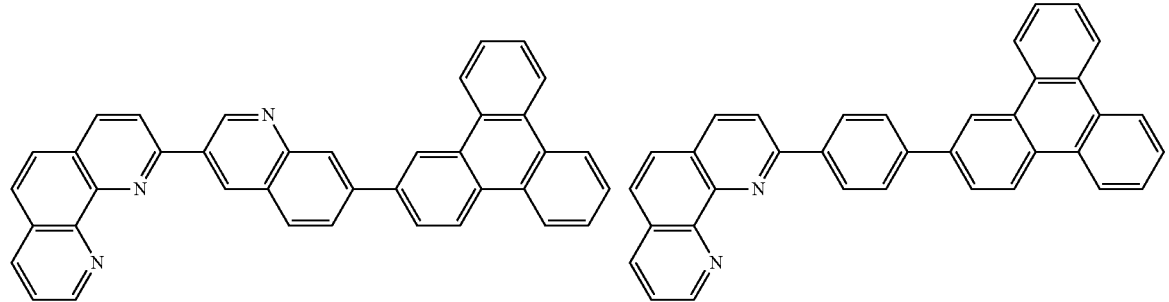
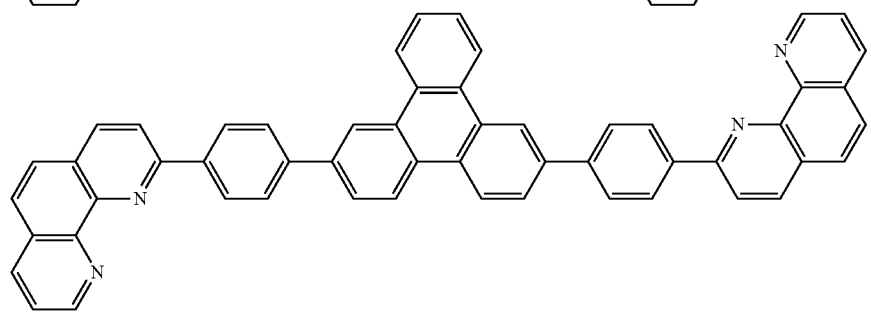
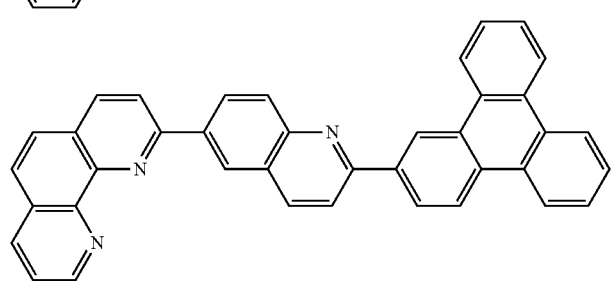
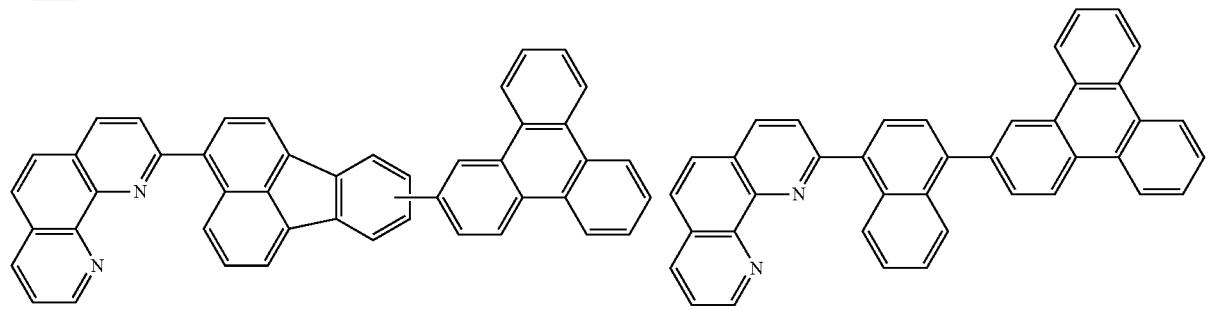
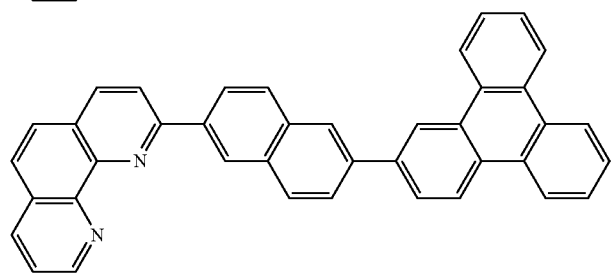
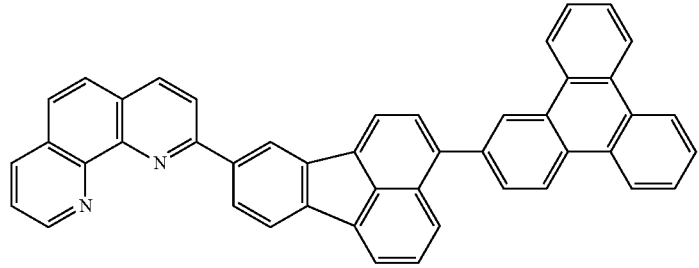

-continued
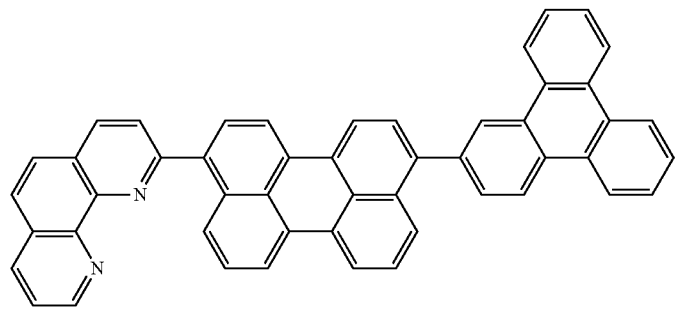
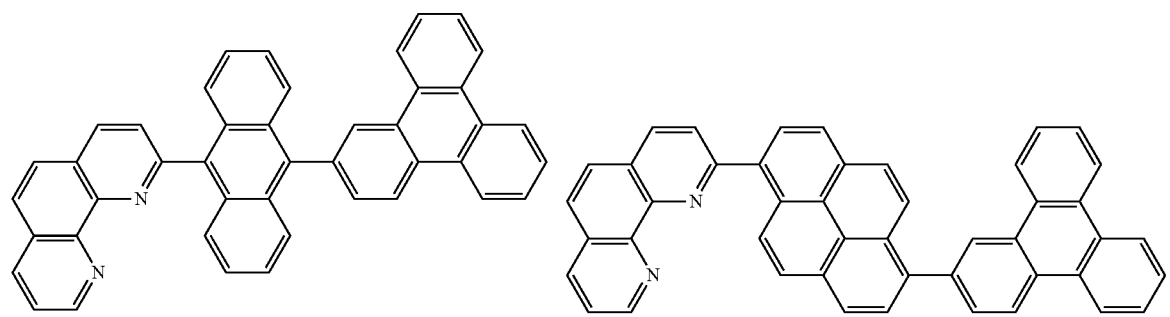
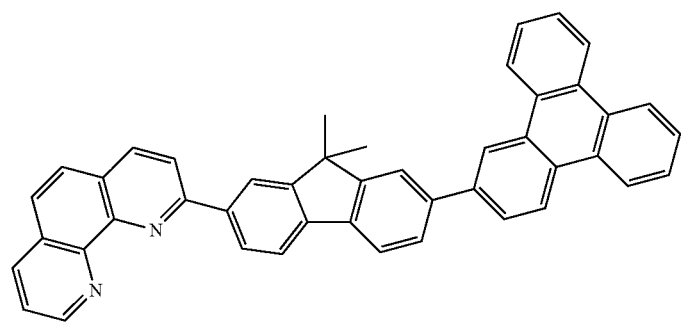
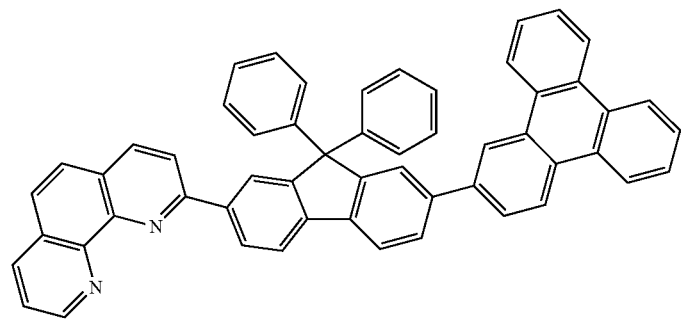
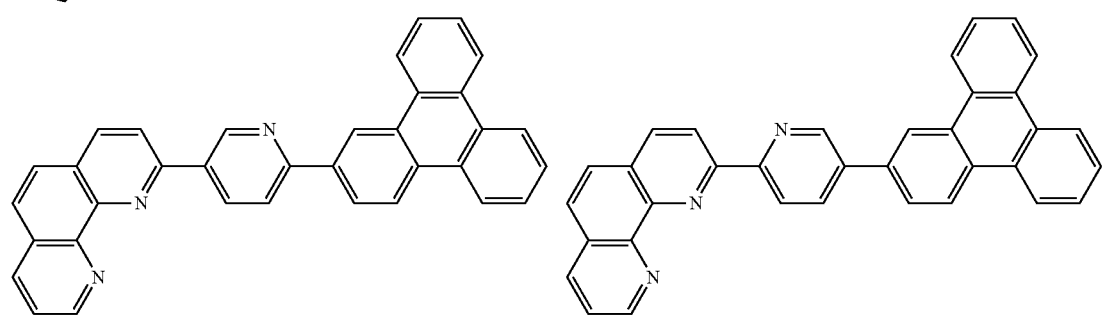

-continued
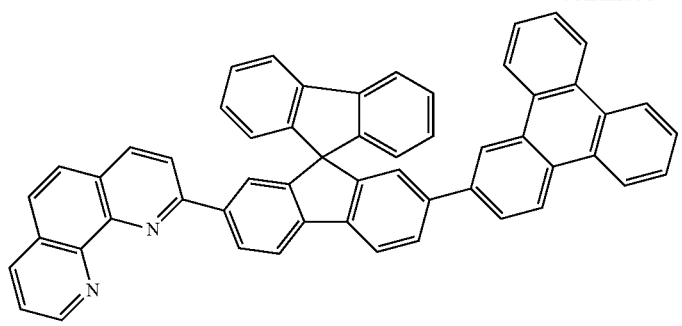
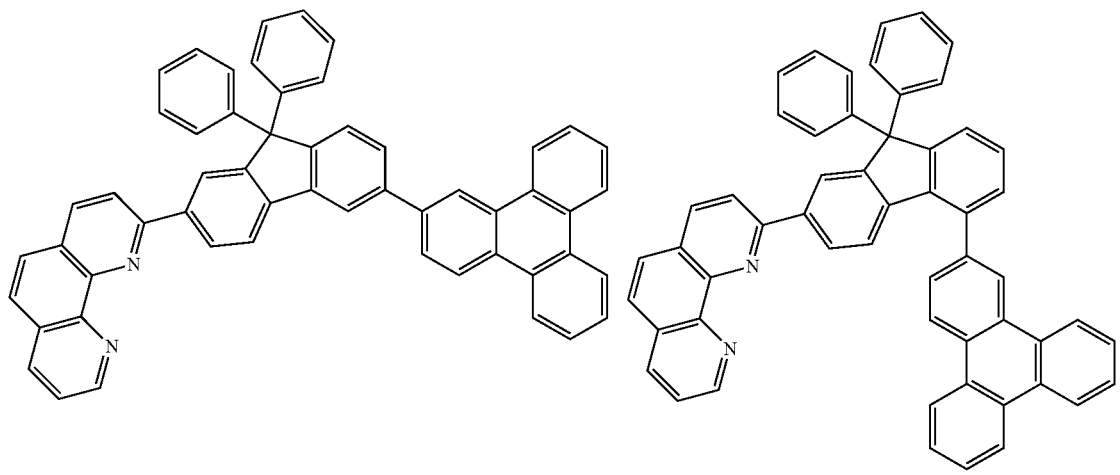
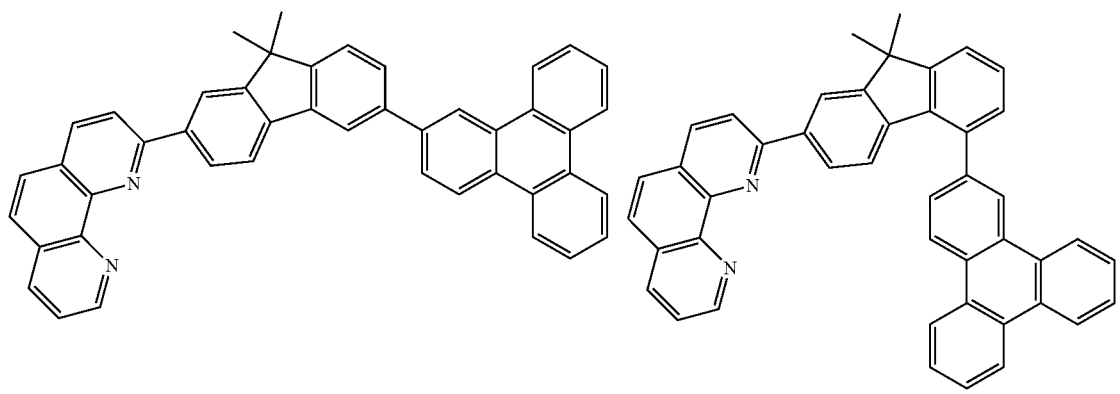
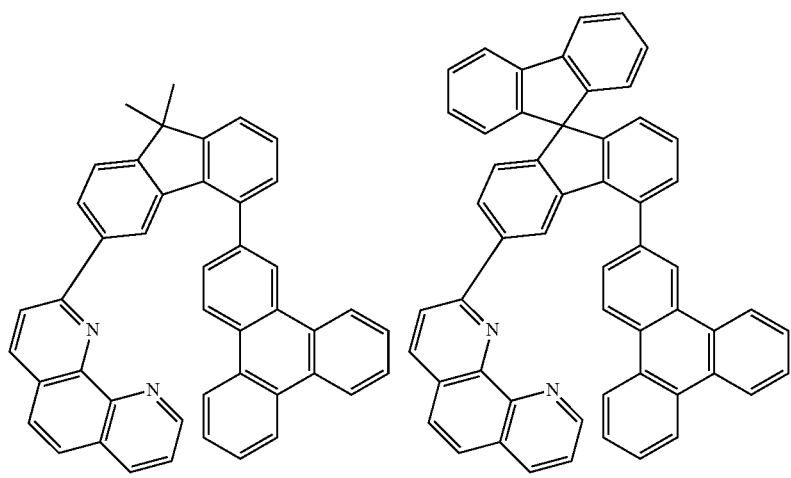

107 108
-continued
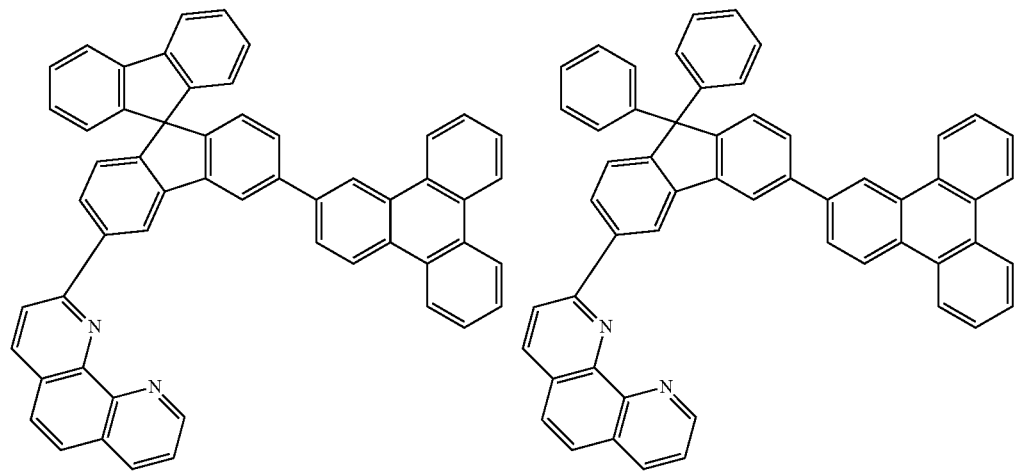
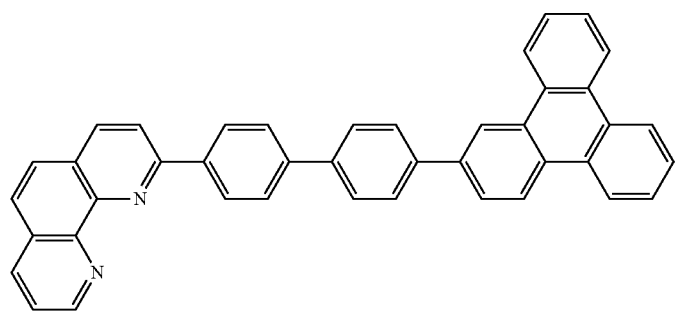
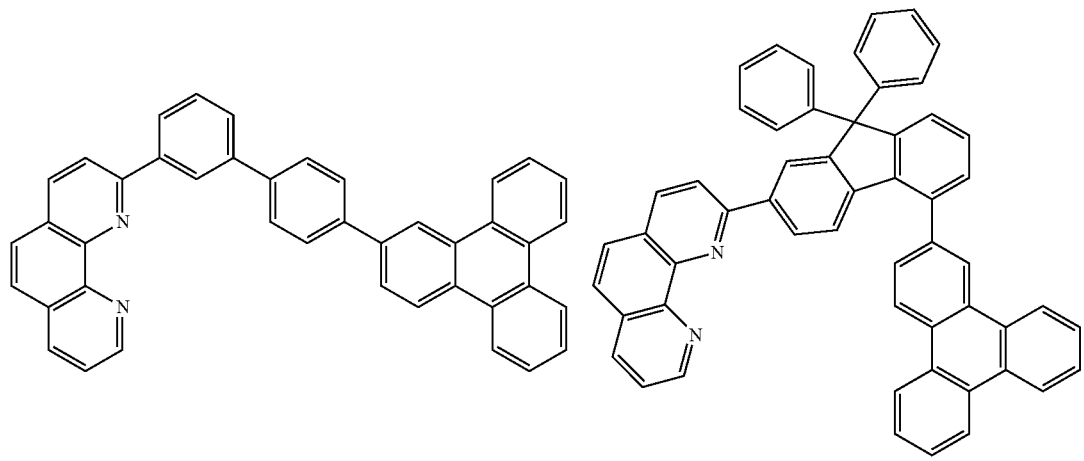
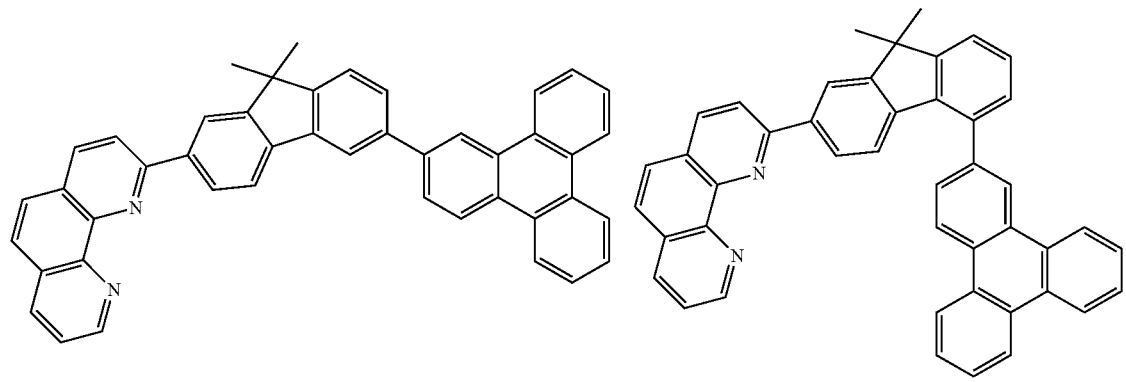

-continued
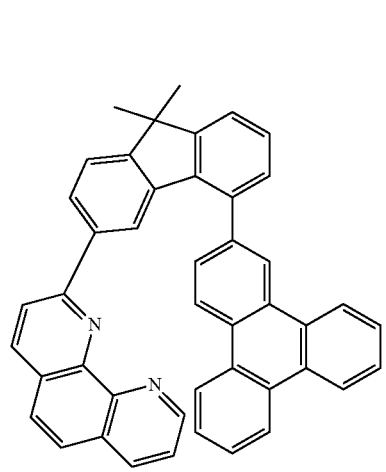
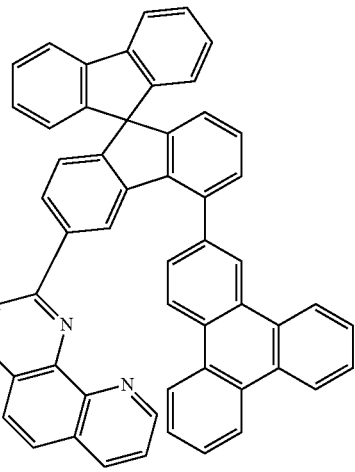
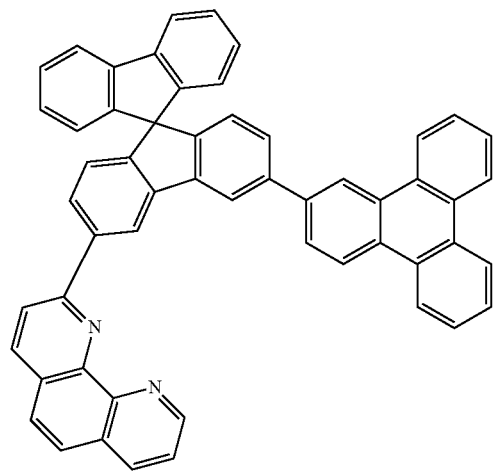
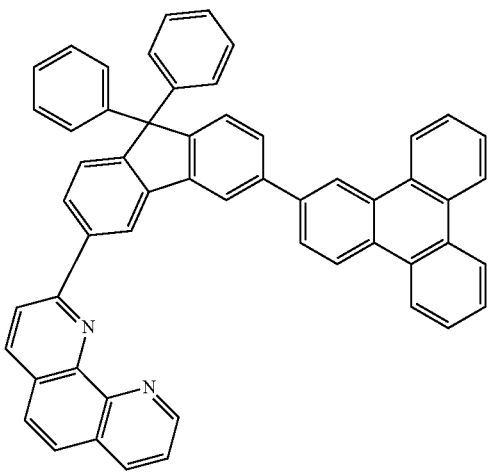
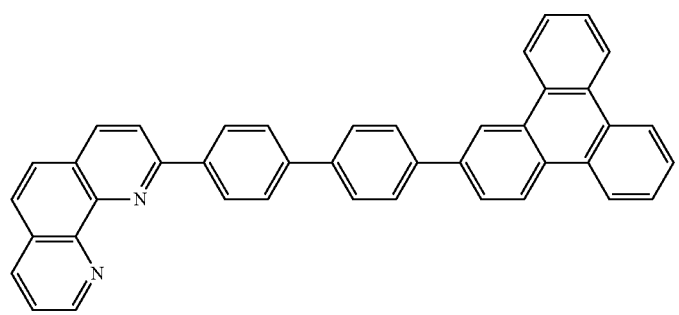
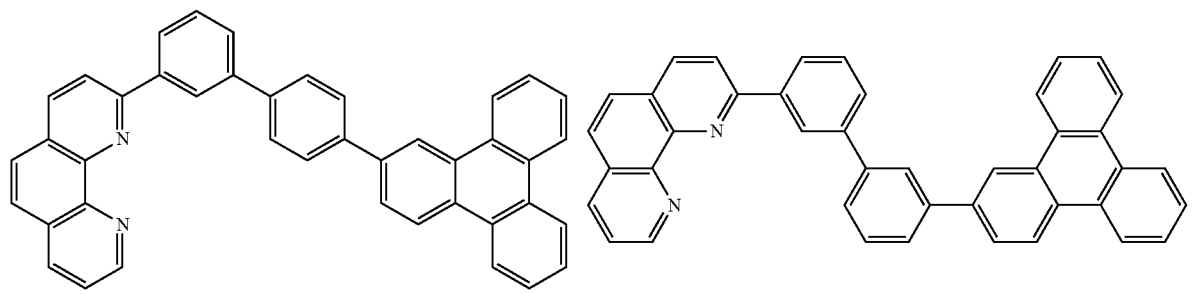

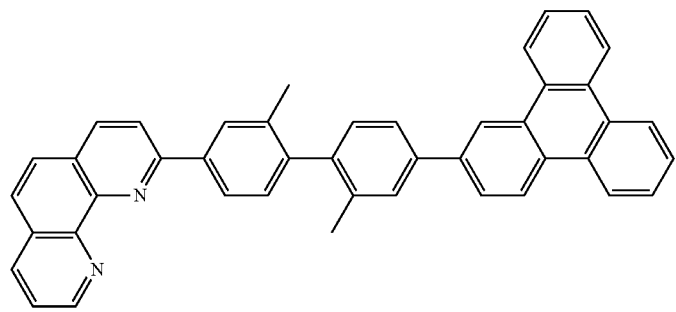
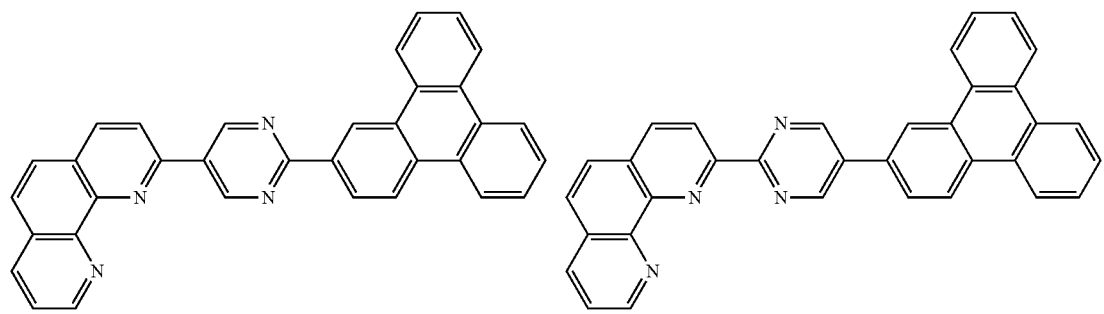
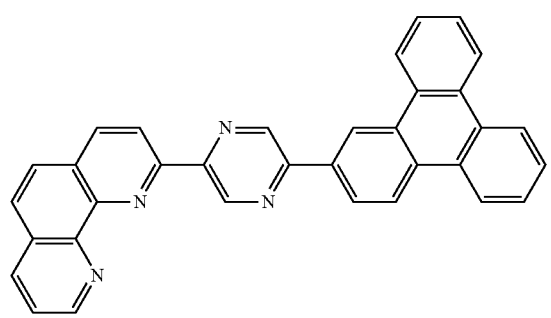
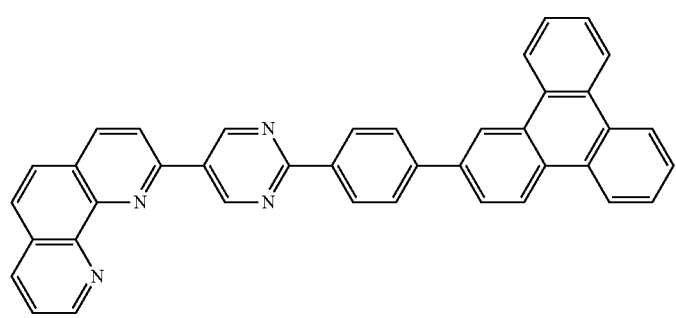
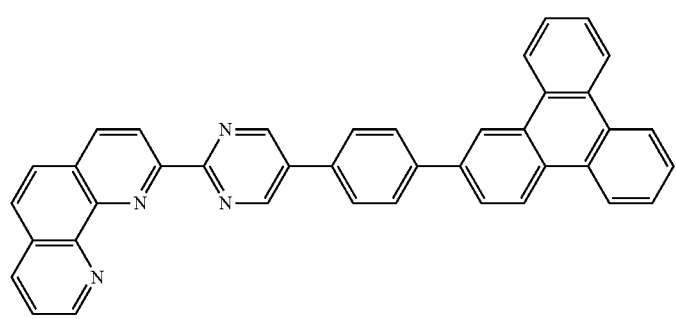

-continued
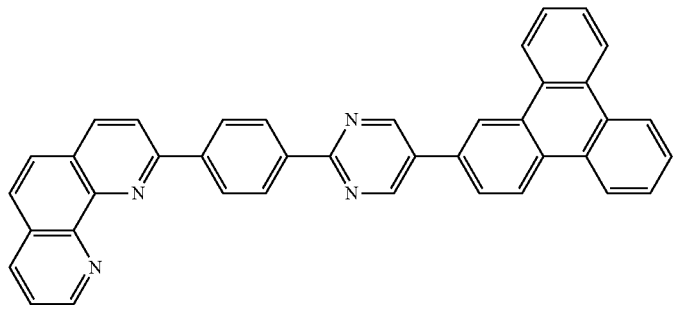
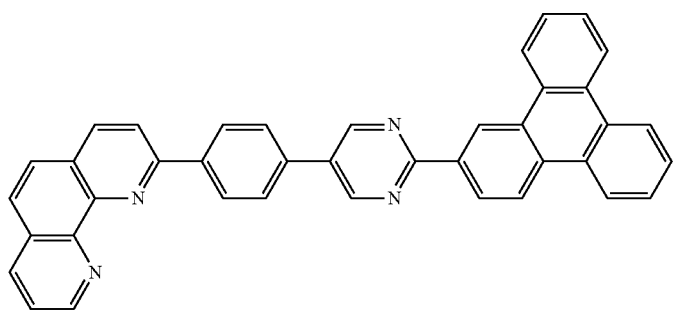
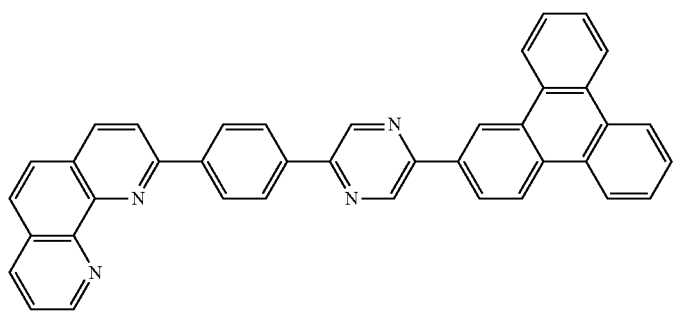
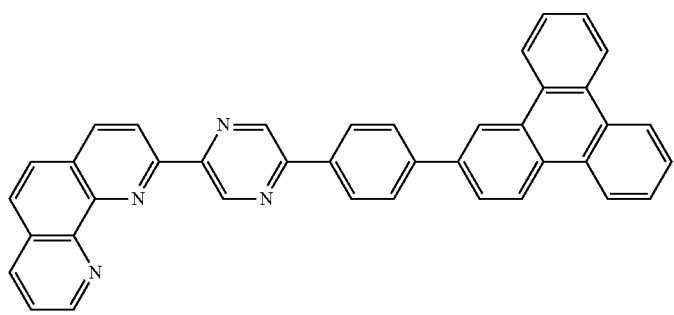
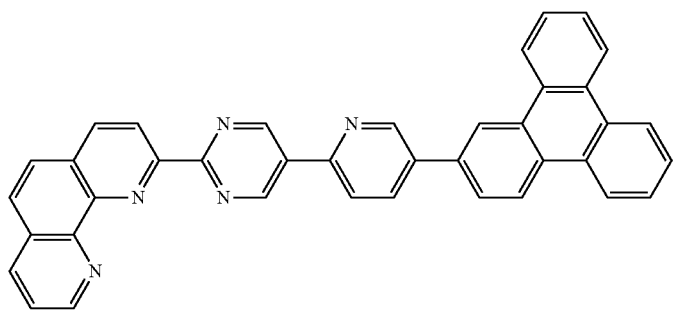

-continued
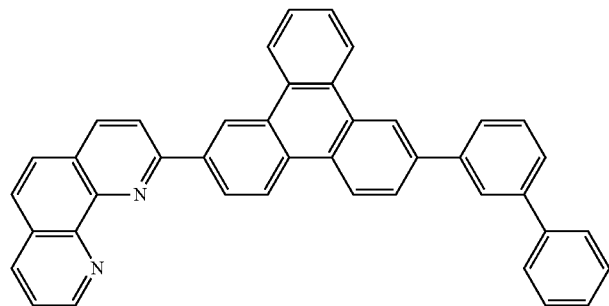
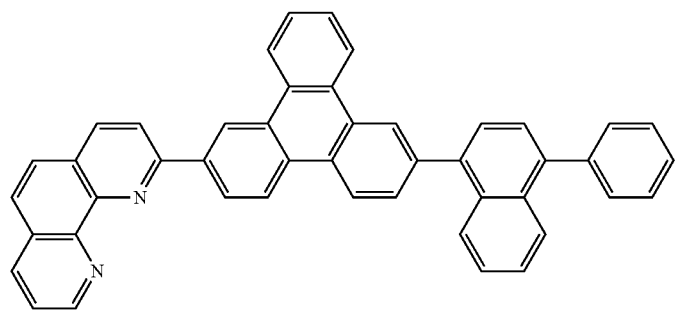
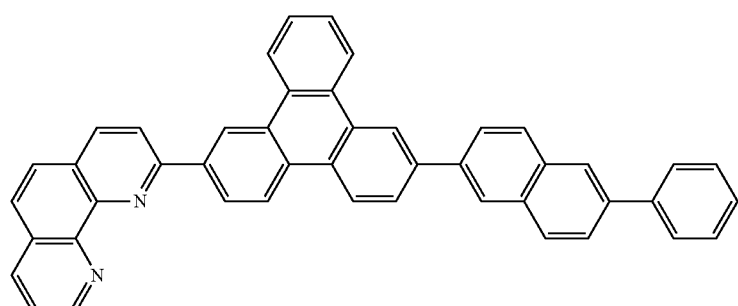
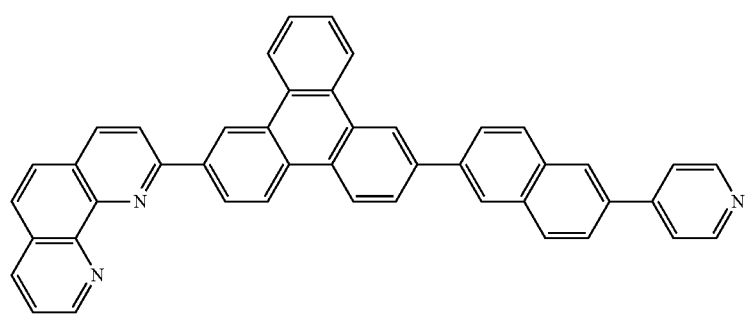
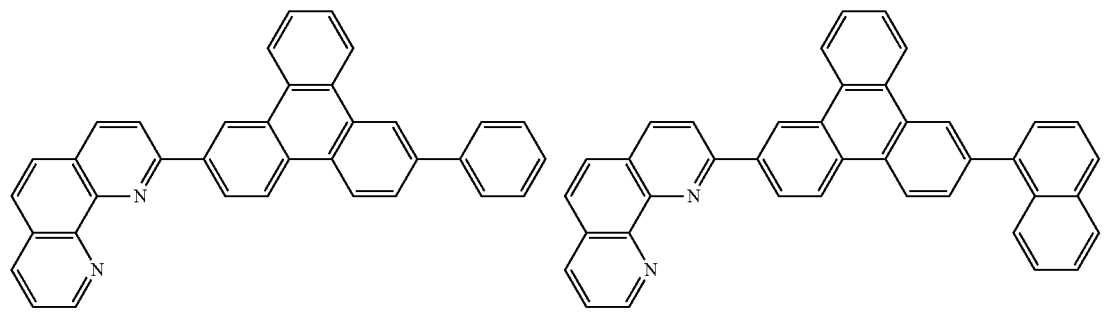

-continued
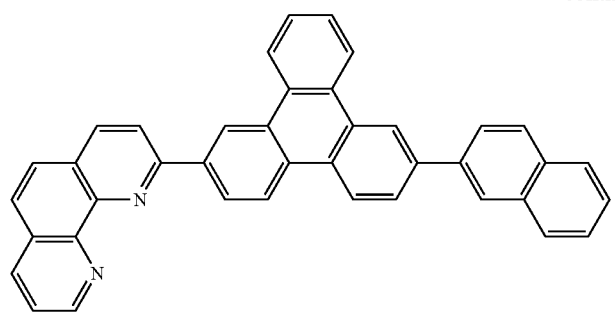
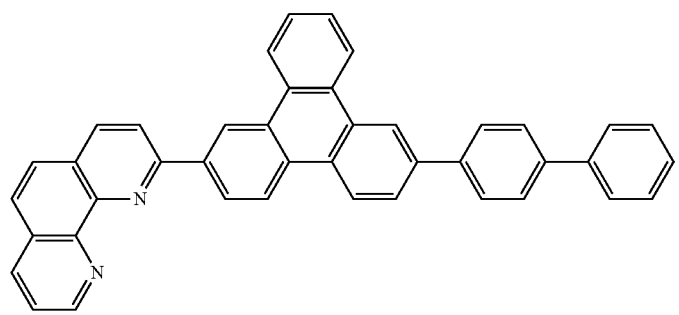
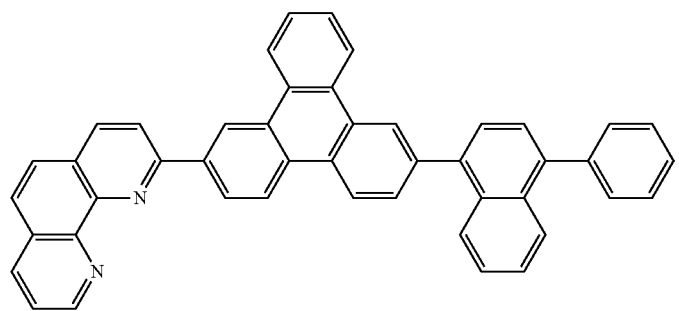
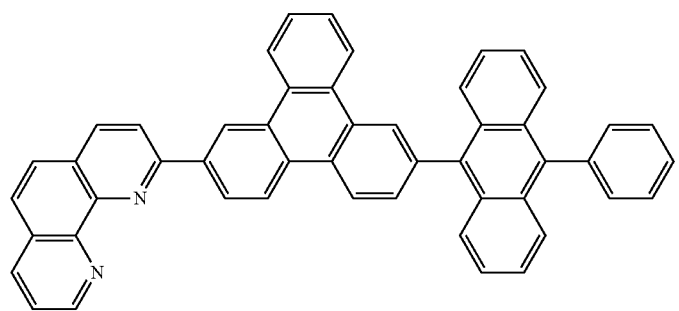
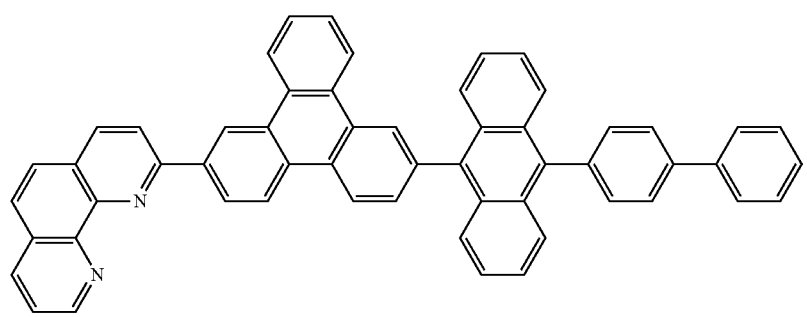

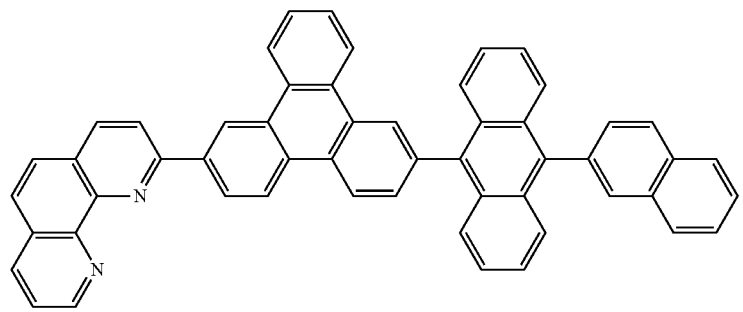
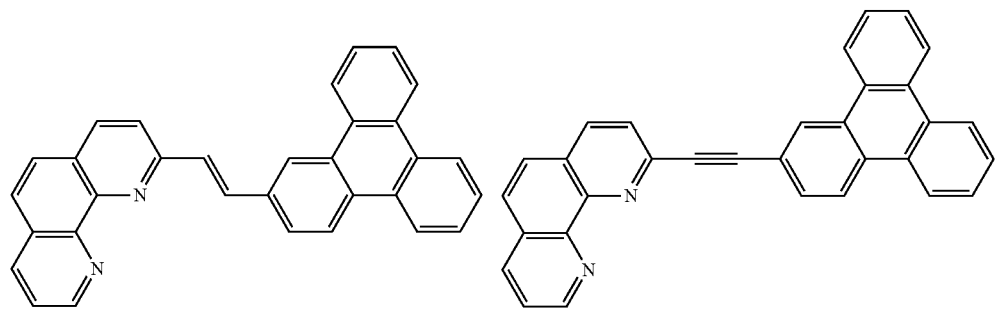
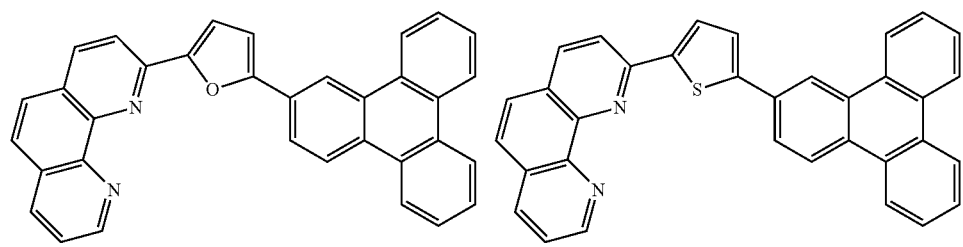
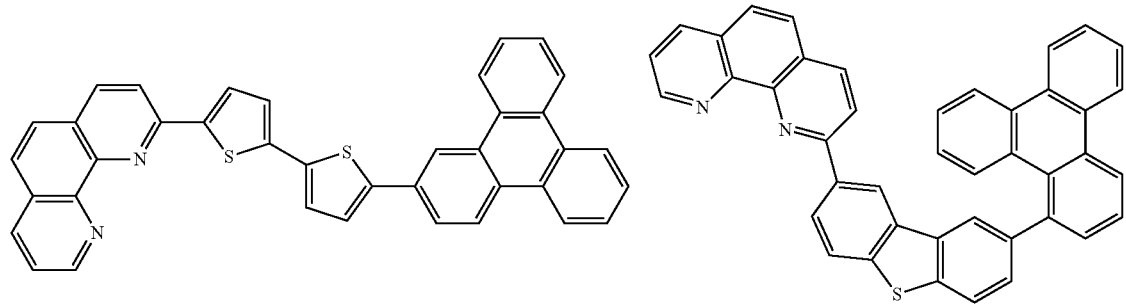
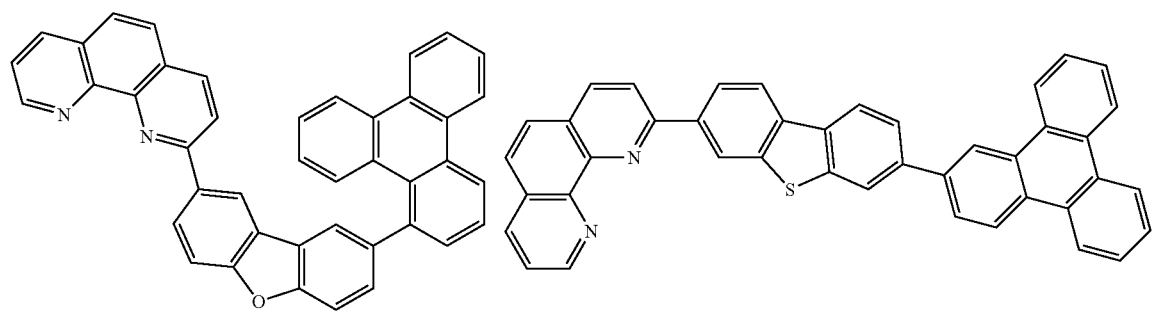
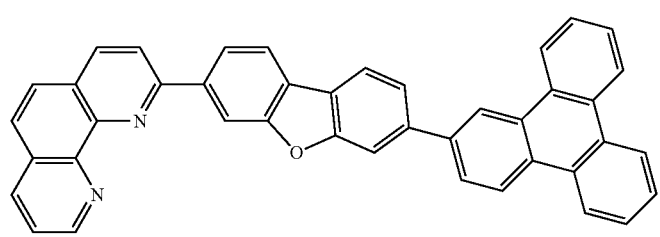

-continued
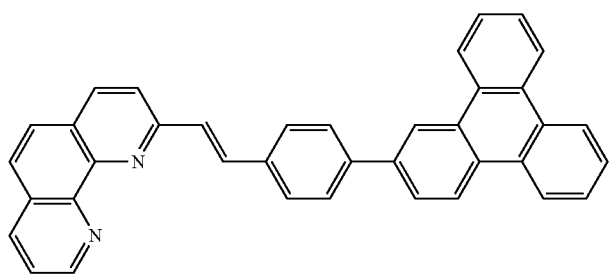
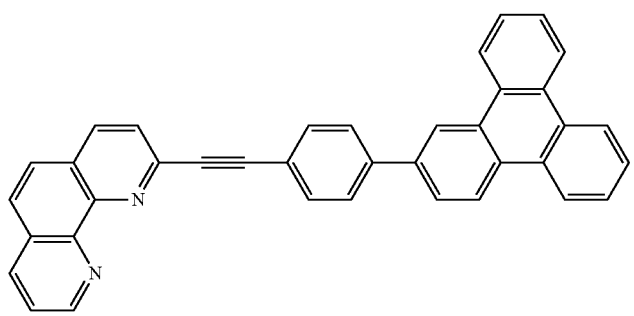
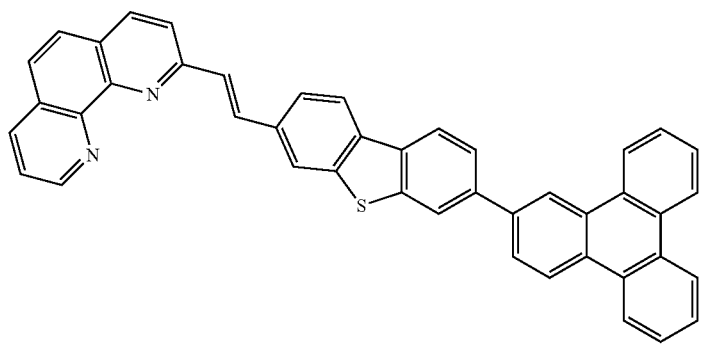
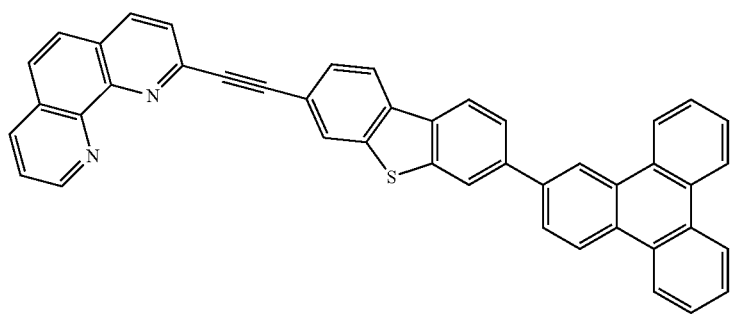
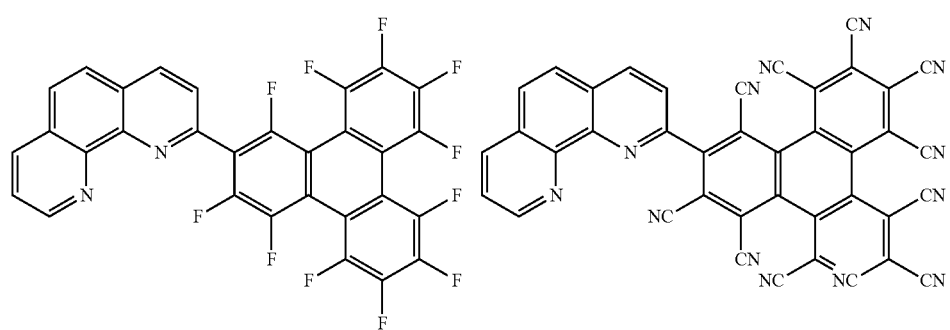

123 124
-continued
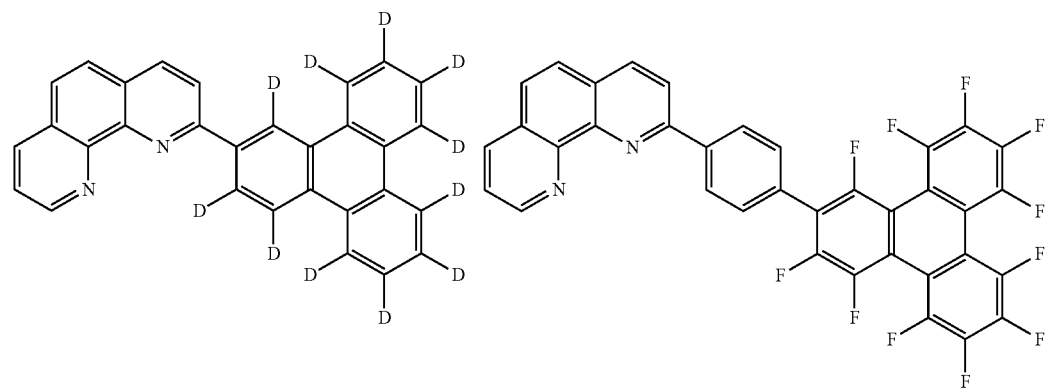
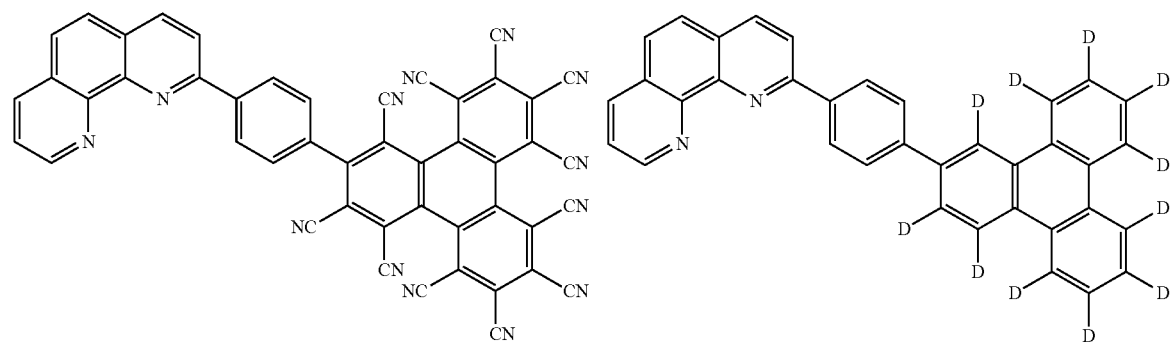
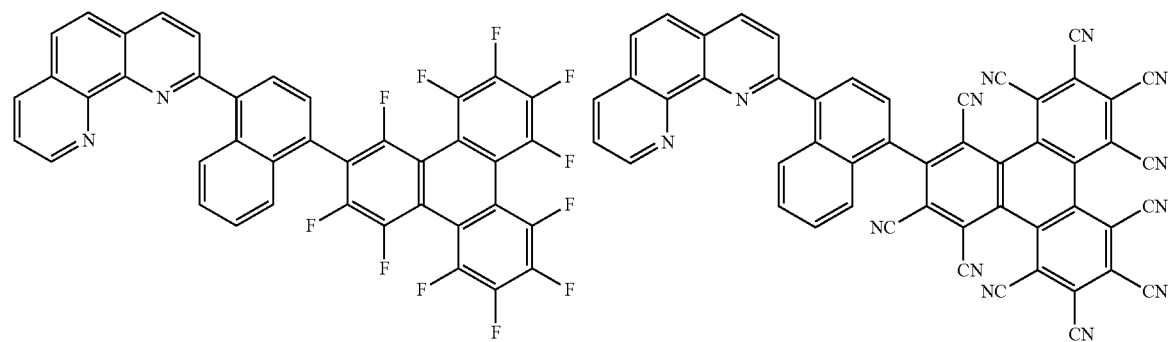
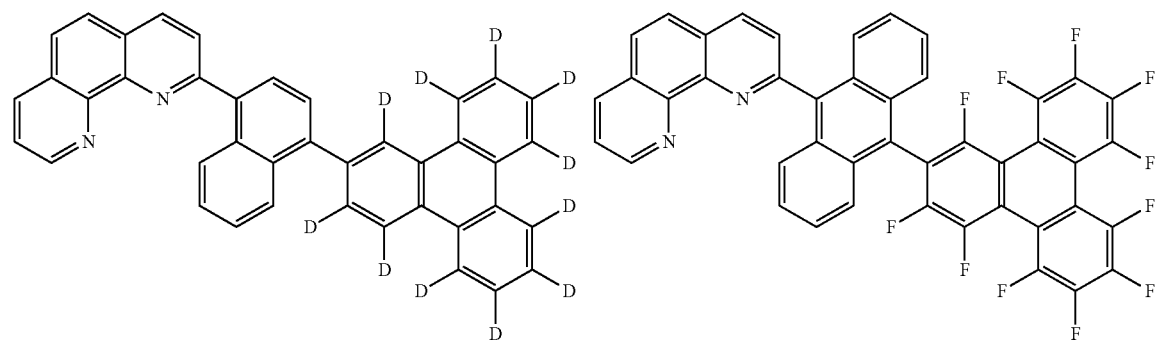

-continued

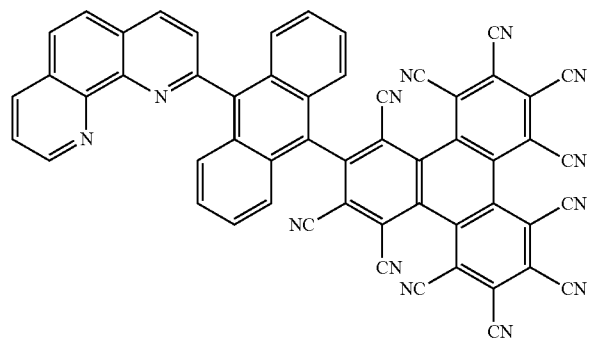 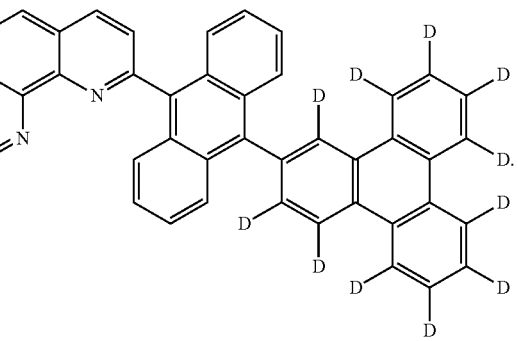

6. An organic light emitting display device, comprising:
at least two or more light emitting parts each comprising a light emitting layer and an electron transport layer; and
a charge generation layer between the at least two or more light emitting parts, wherein the charge generation layer comprises a P-type charge generation layer and an N-type charge generation layer, where the N-type charge generation layer includes a compound represented by the following Chemical Formula 1:

[Chemical Formula 1]

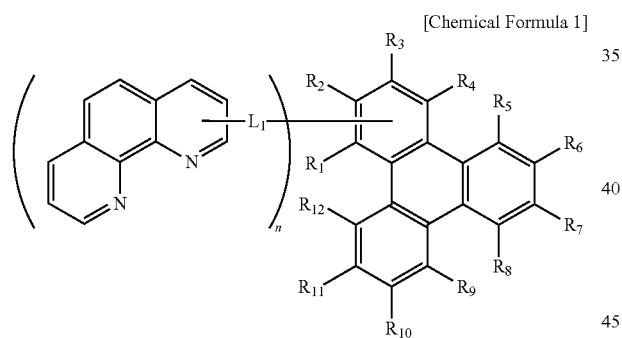

wherein $L_1$ includes one among a substituted or unsubstituted arylene group with 6 to 60 carbon atoms, a substituted or unsubstituted heteroarylene group with 3 to 60 carbon atoms, and a single bond;

one among $R_1$ to $R_{12}$ binds to $L_1$, and the others among $R_1$ to $R_{12}$ that do not bind to $L_1$ include independently one among a substituted or unsubstituted aryl group with 5 to 30 carbon atoms, a substituted or unsubstituted heteroaryl group with 4 to 30 carbon atoms, a halogen group, a nitrile group, heavy hydrogen, and hydrogen; and n includes one among 1 and 2.

7. The organic light emitting display device of claim 6, wherein the compound represented by Chemical Formula 1 includes one among the following compounds:

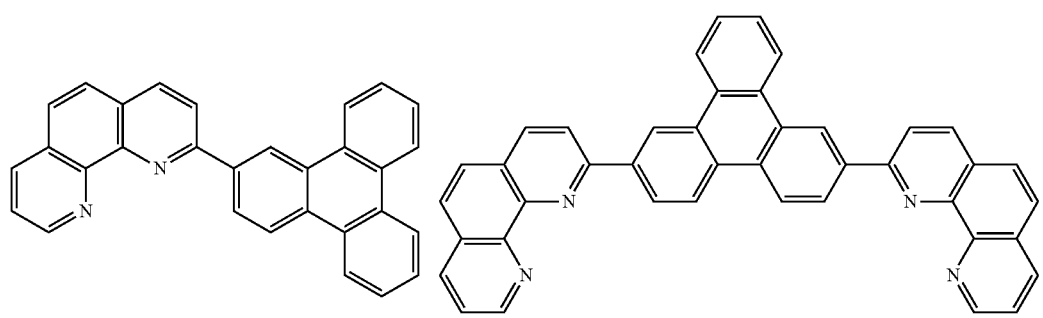

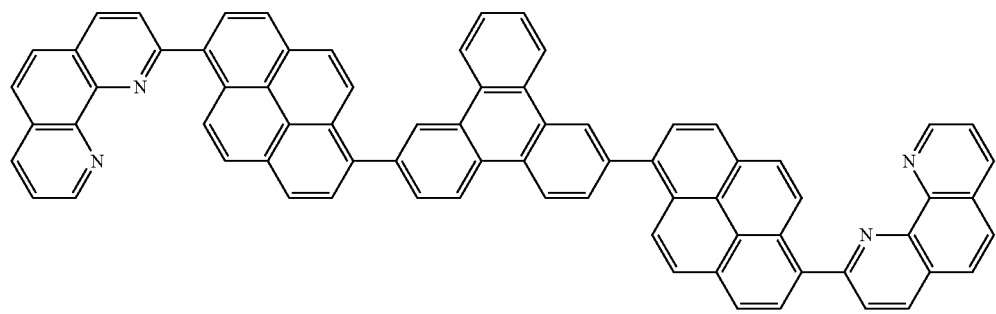
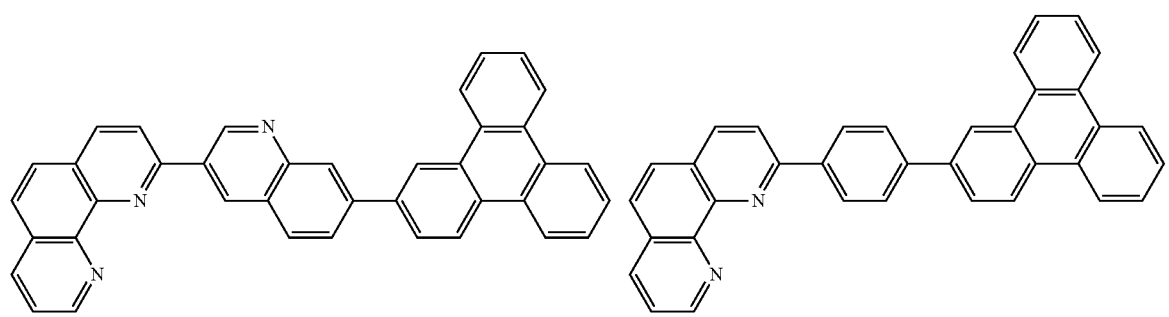
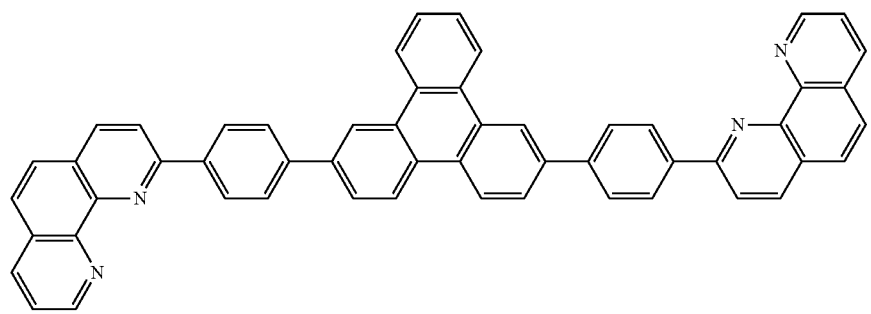
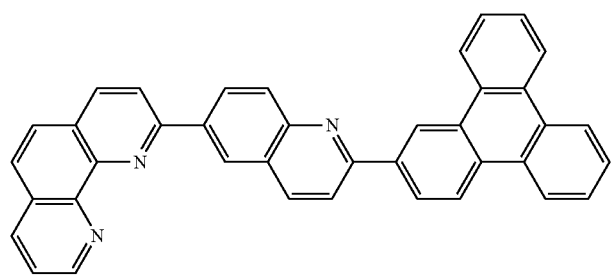
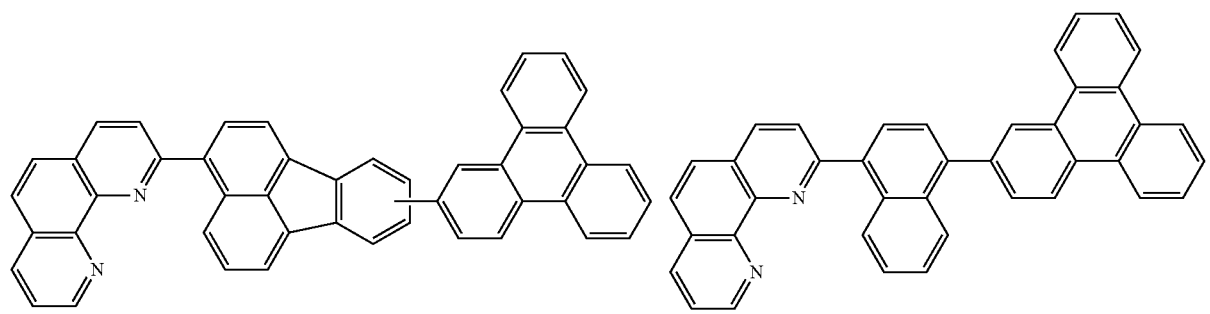

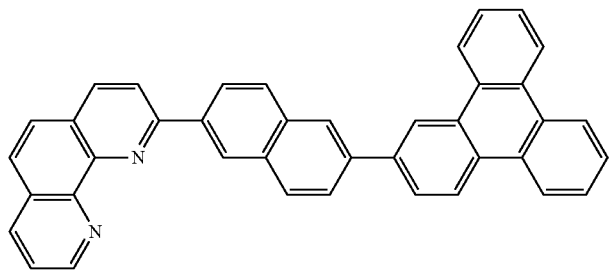
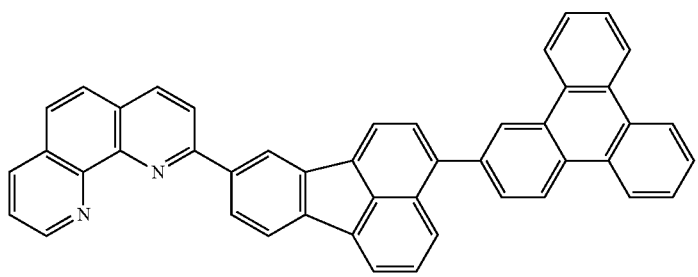
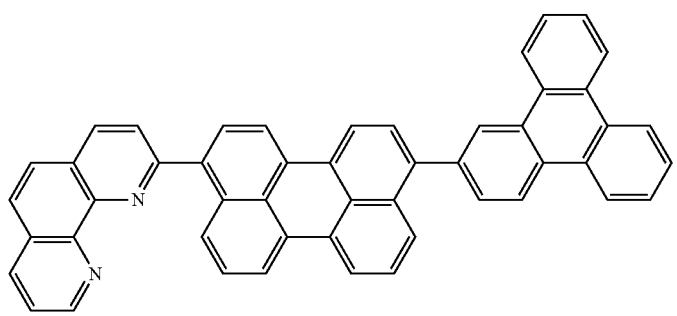
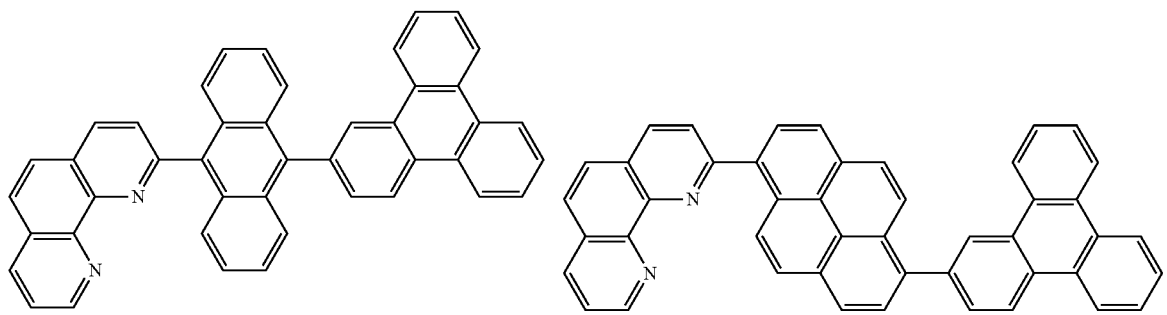
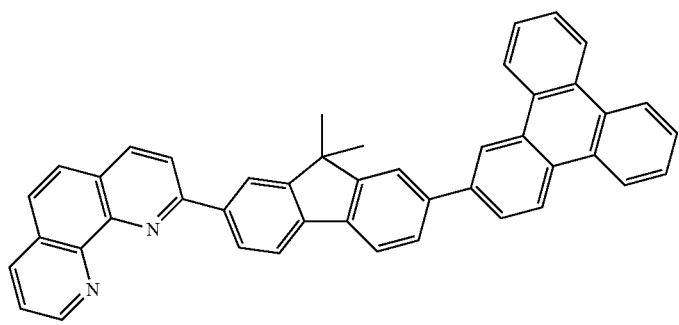

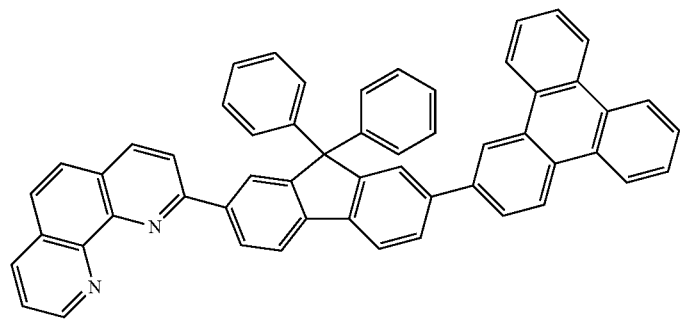
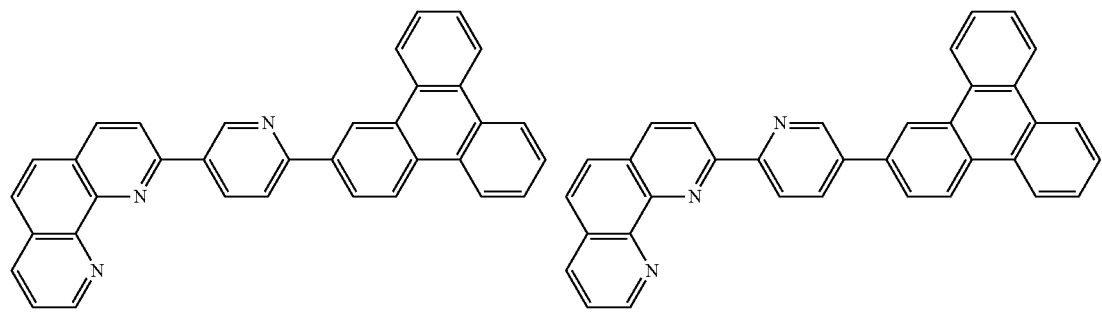
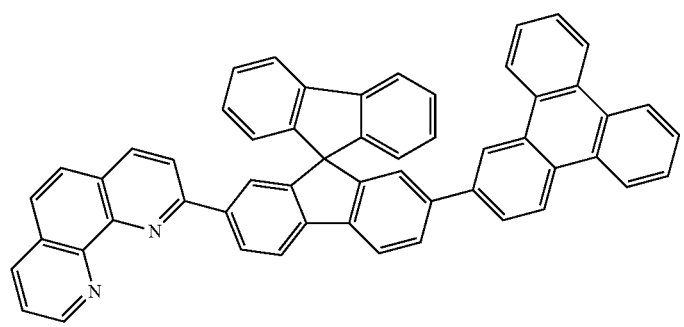
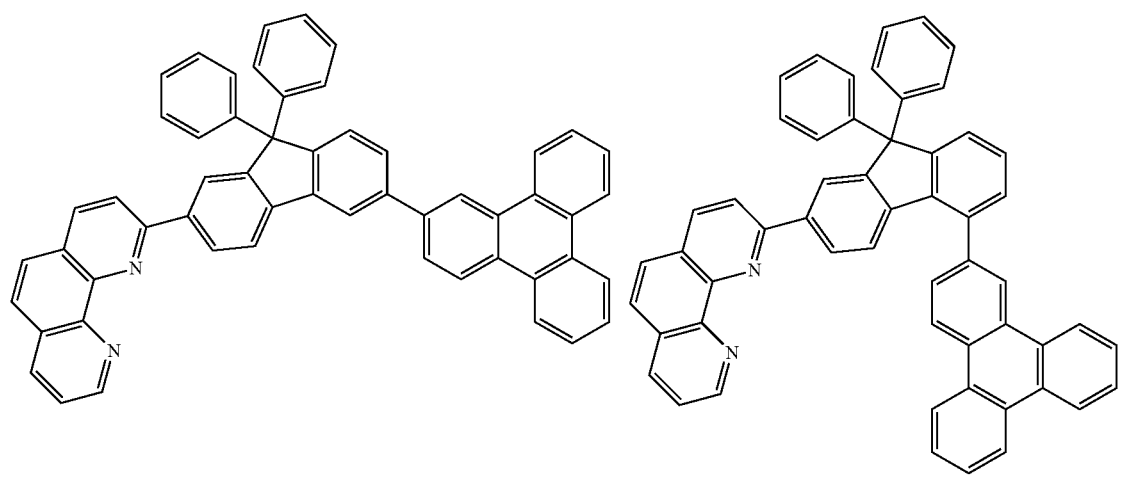

-continued
133  134
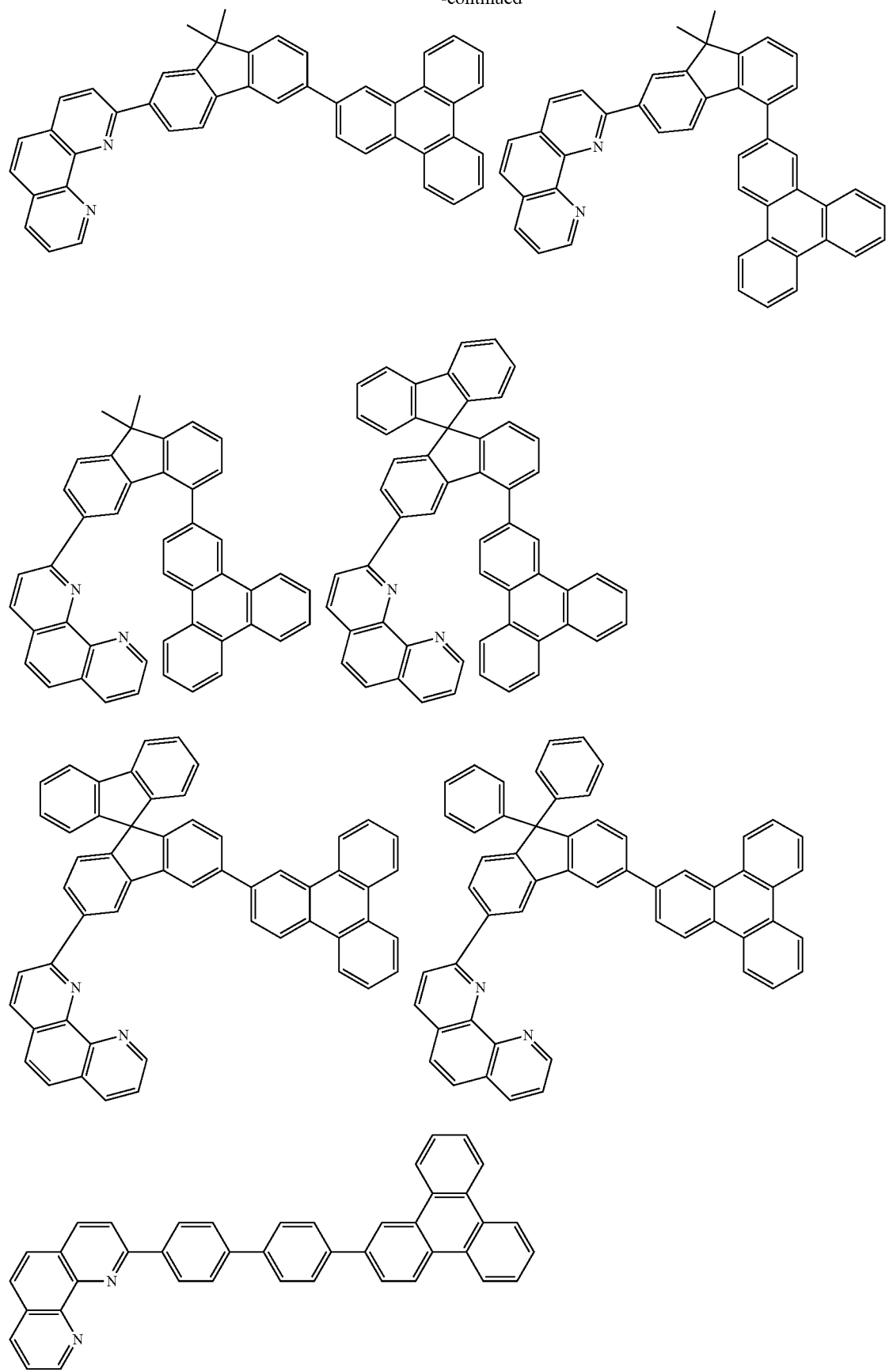

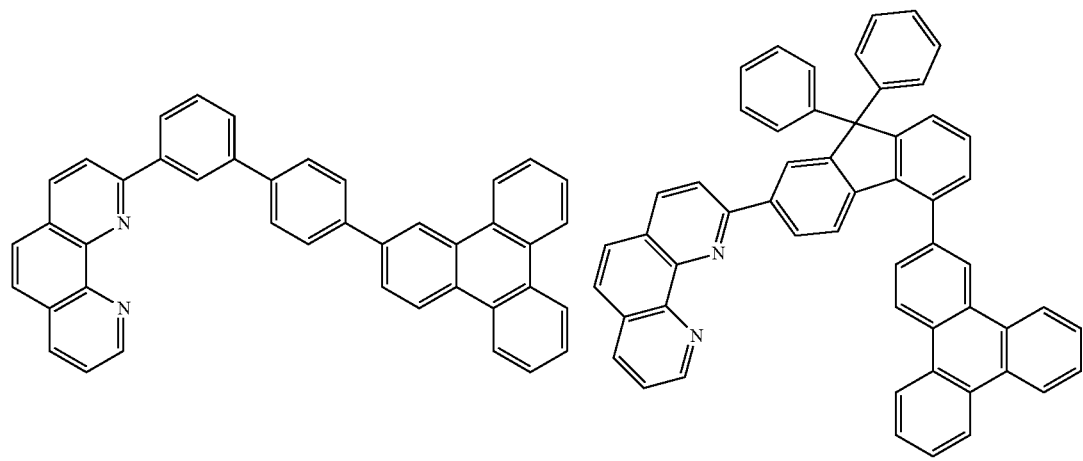
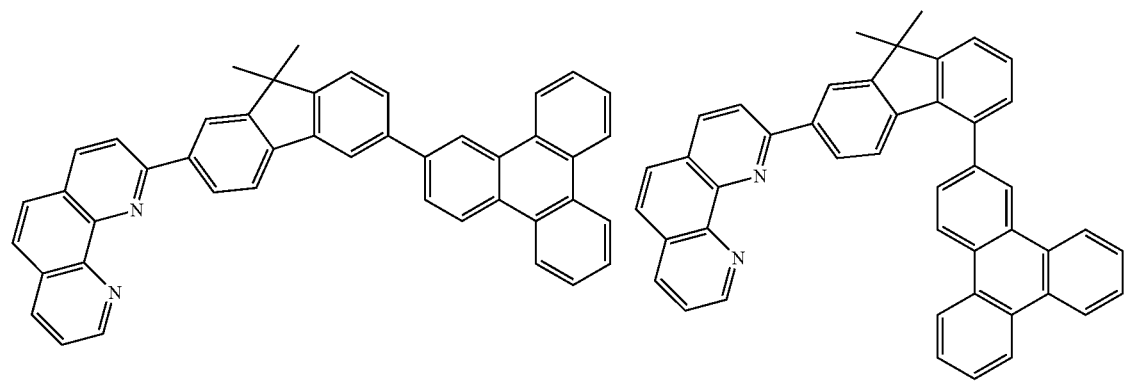
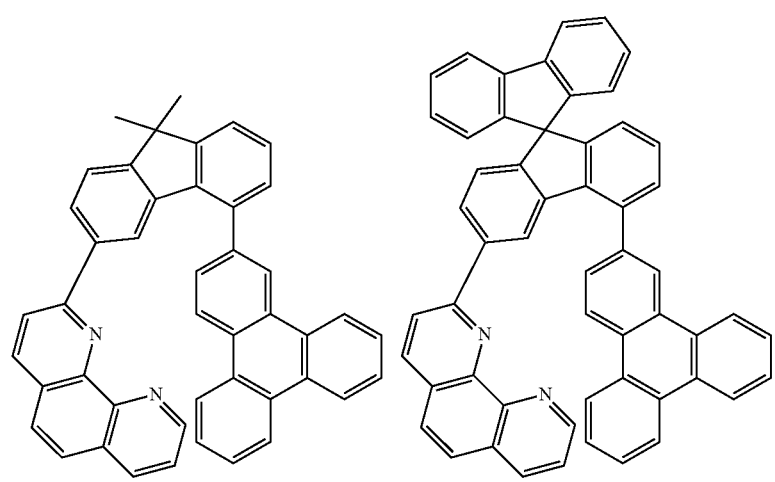

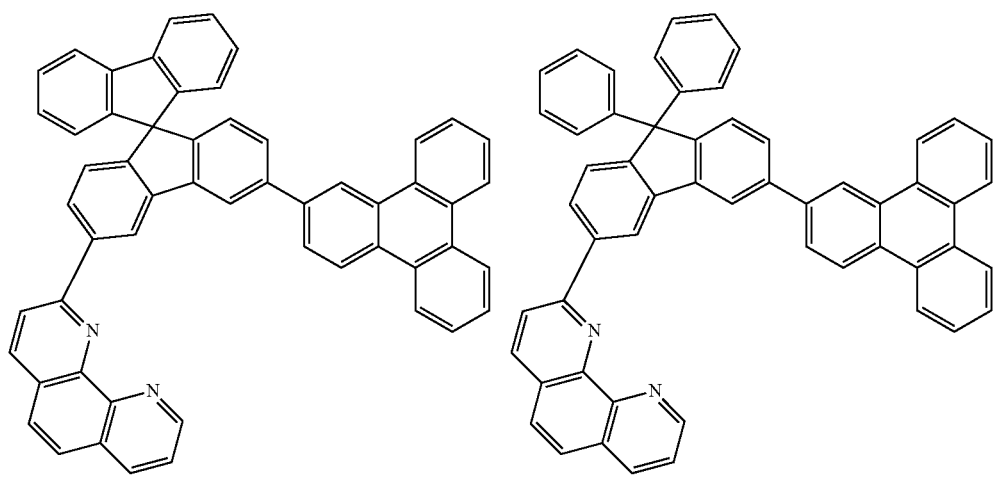
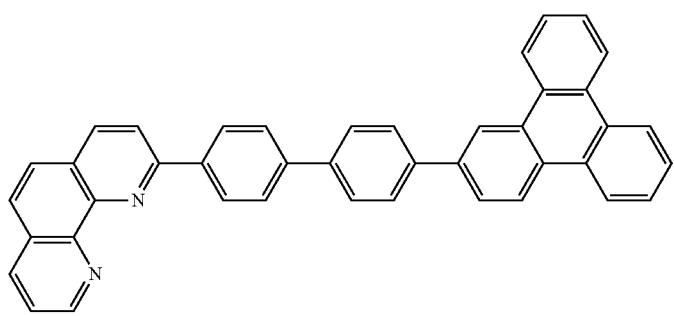
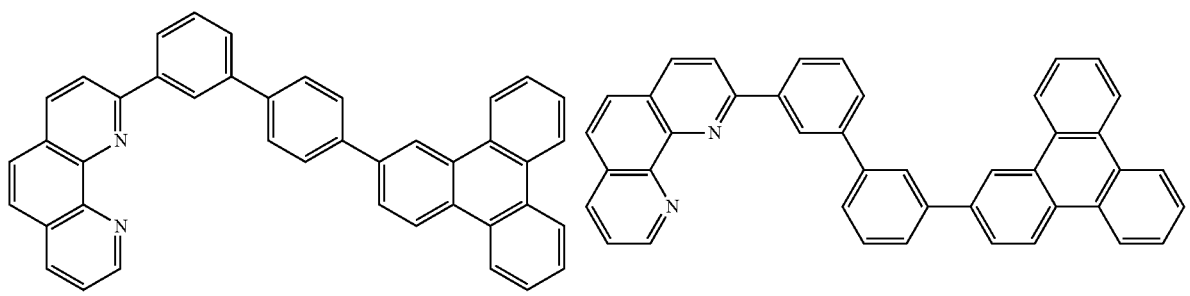
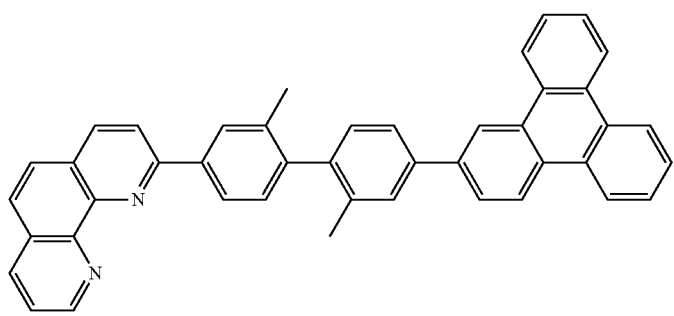
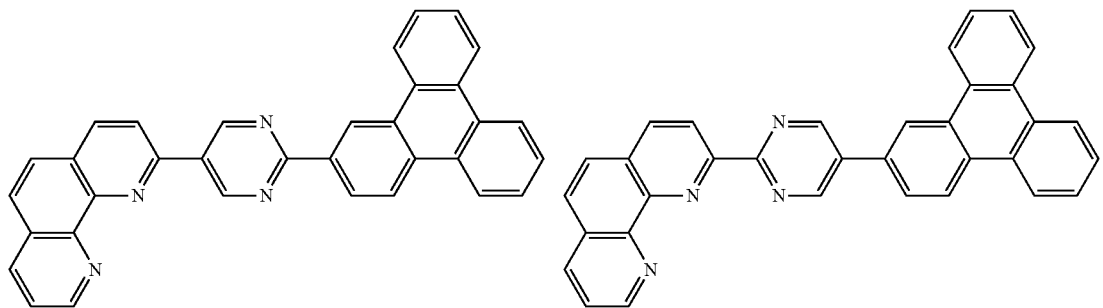

-continued
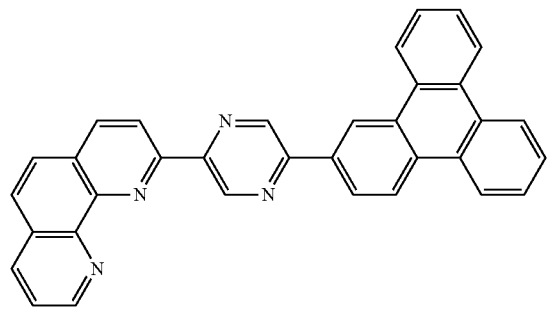
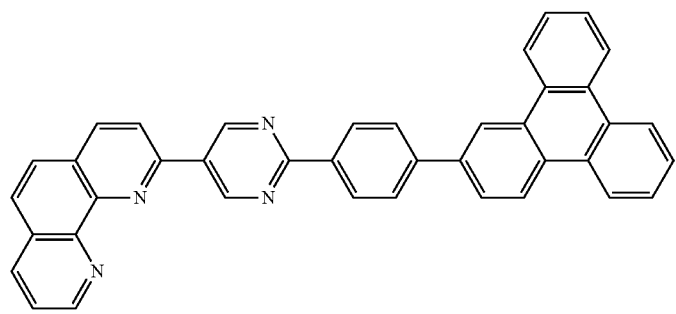
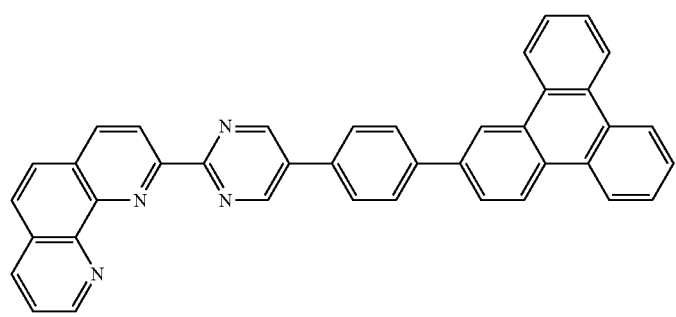
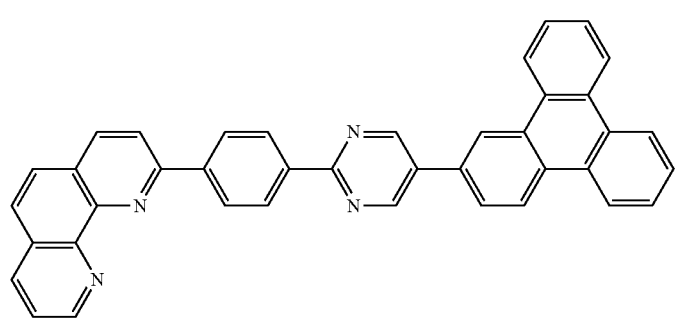
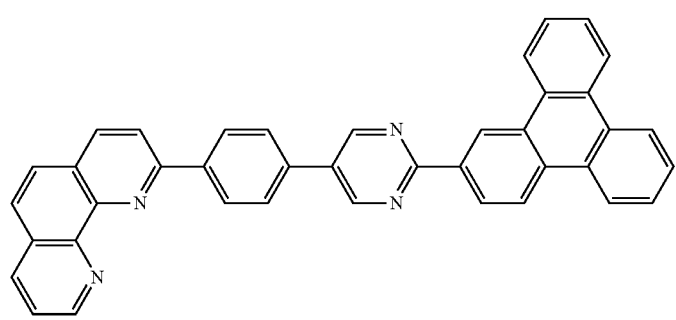

-continued
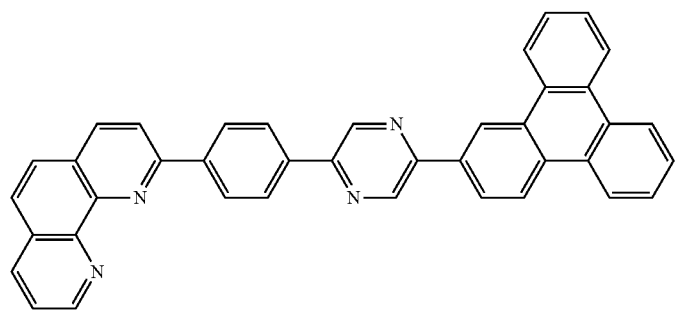
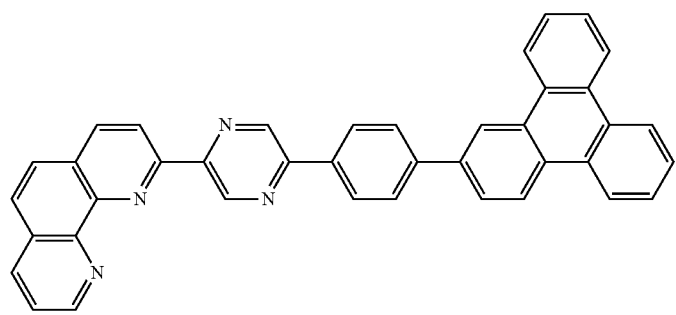
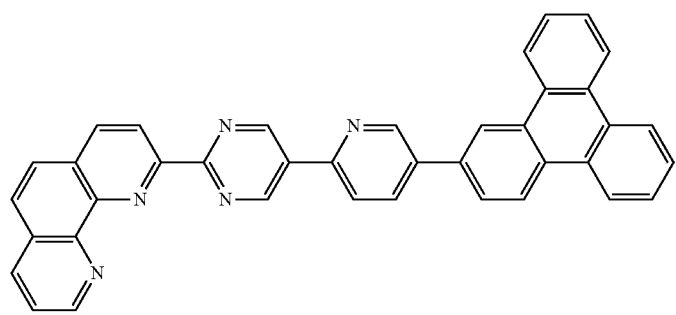
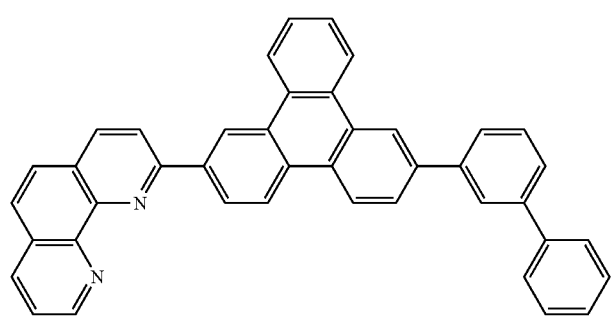
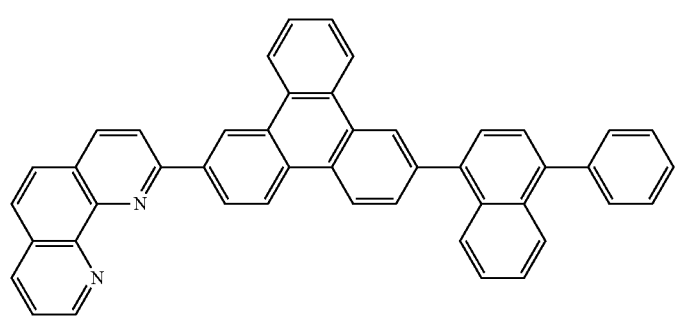

-continued
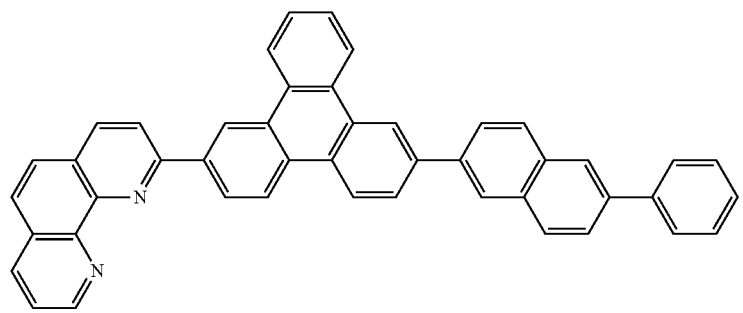
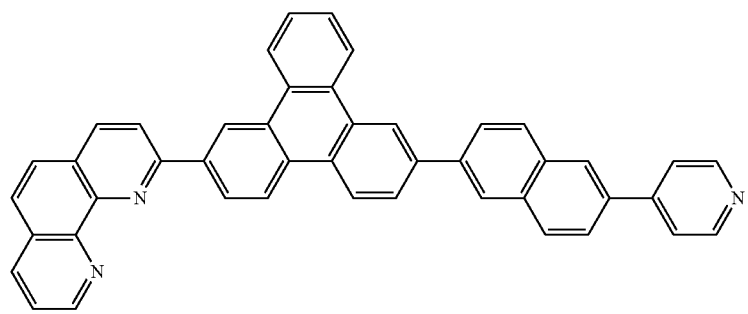
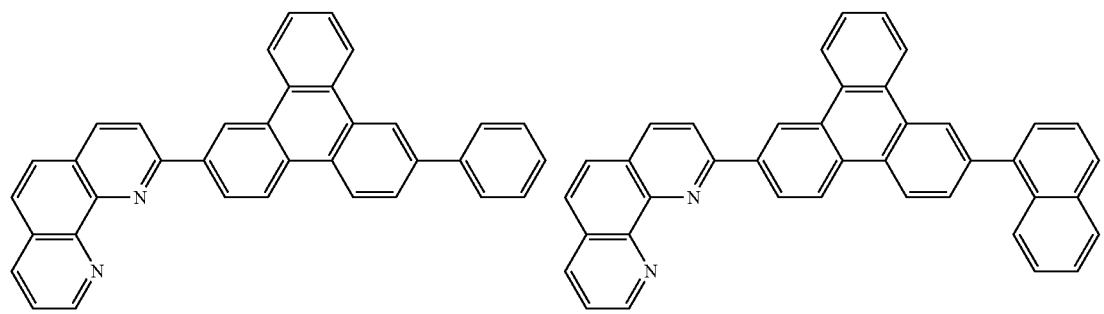
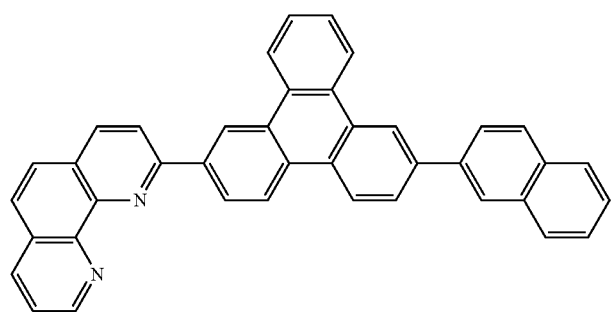
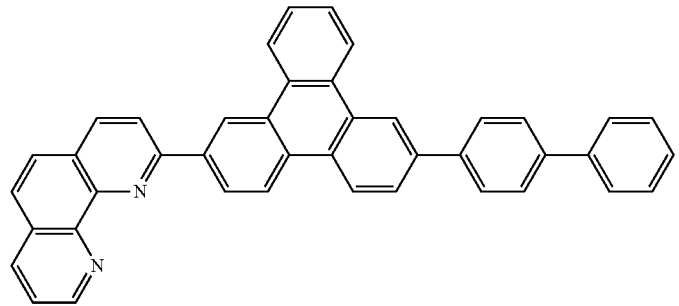

-continued
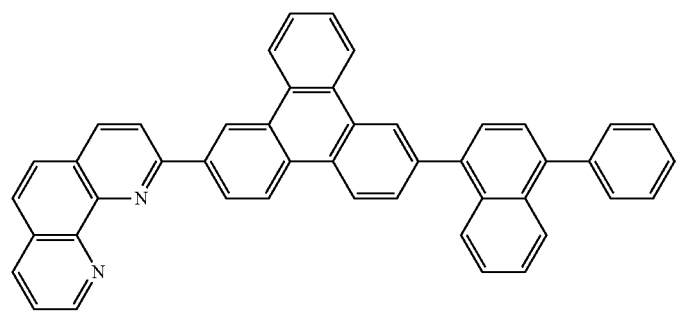
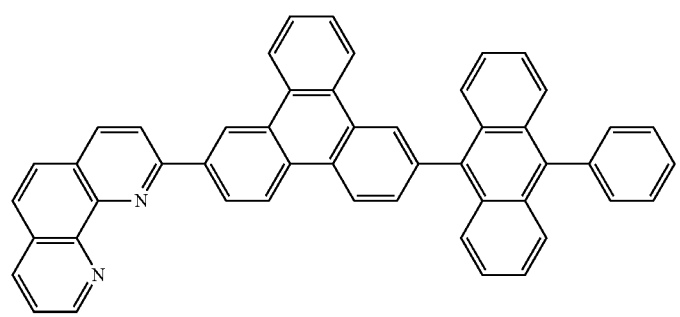
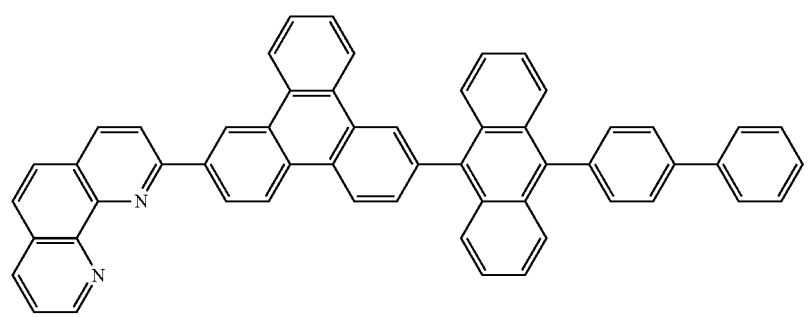
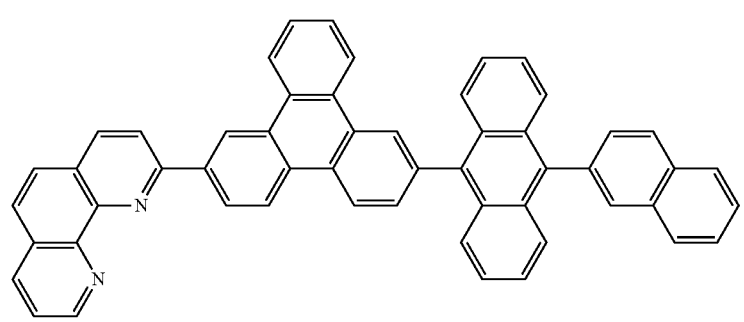
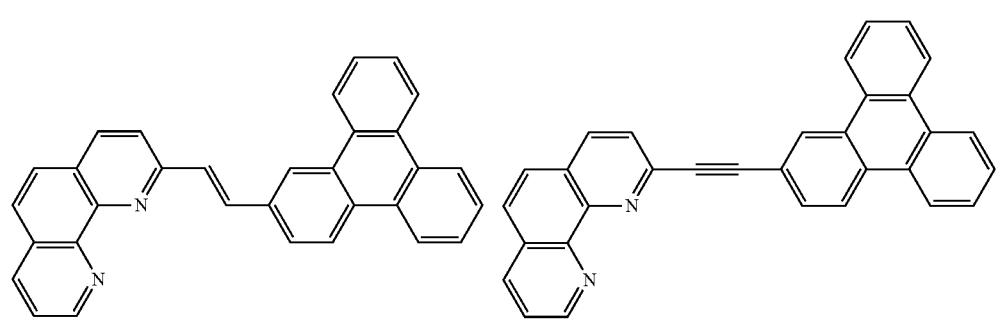

-continued
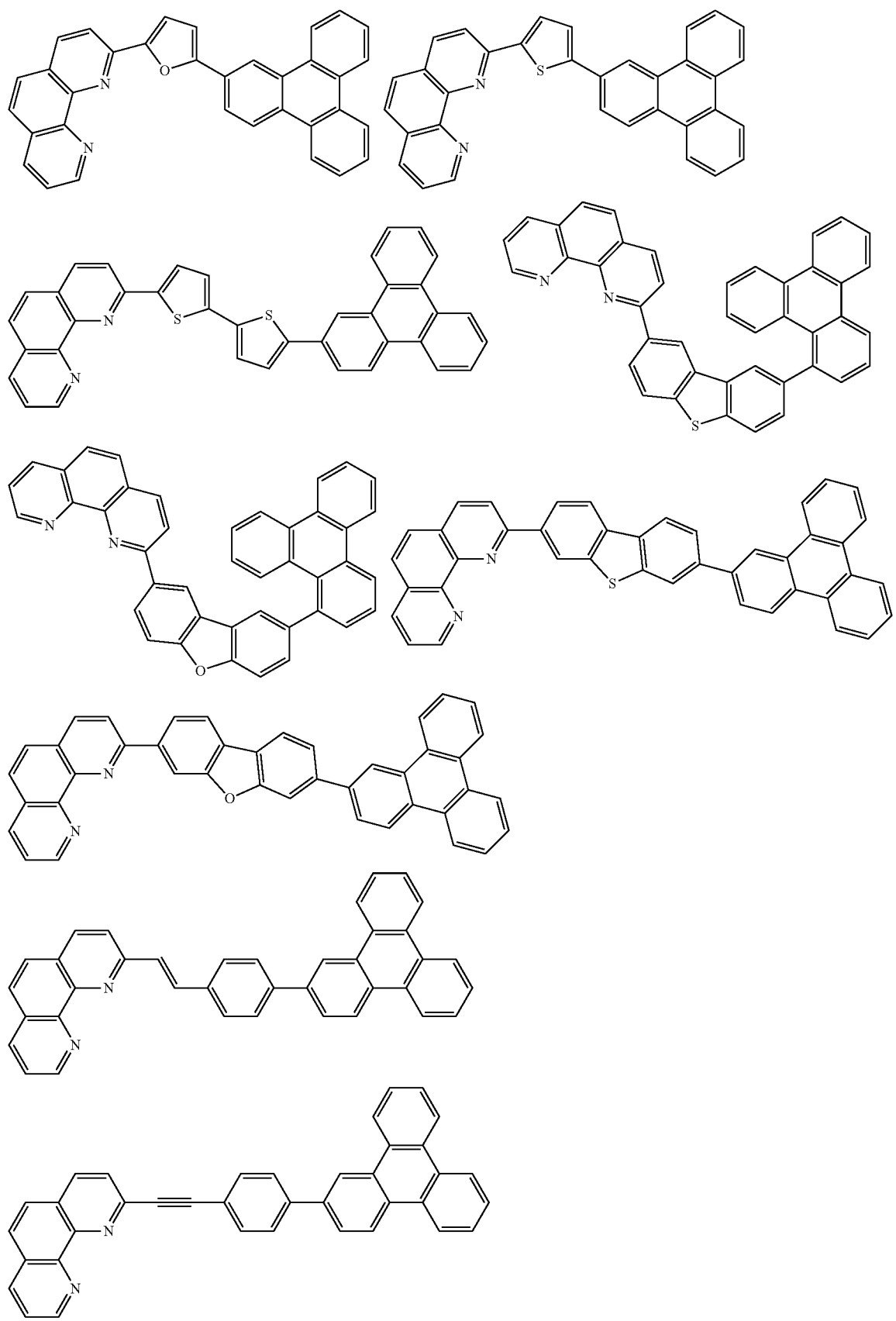

-continued
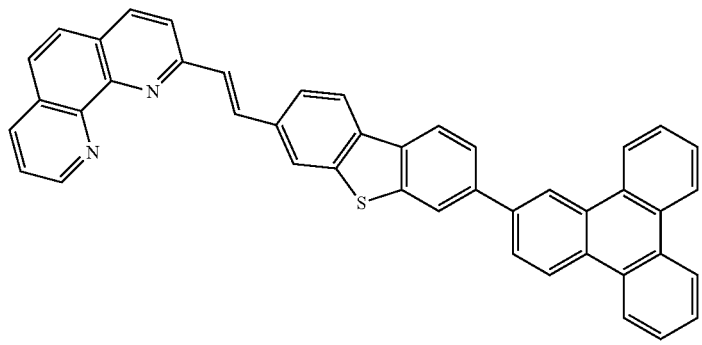
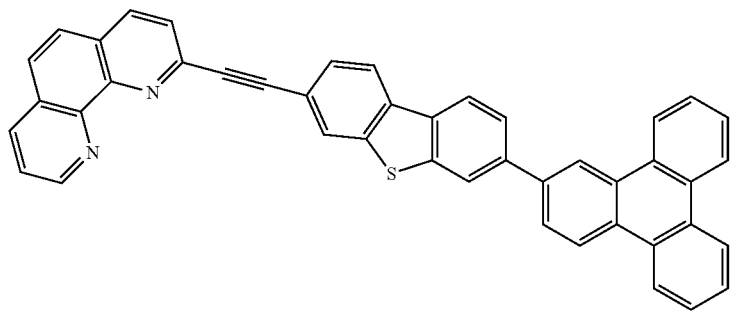
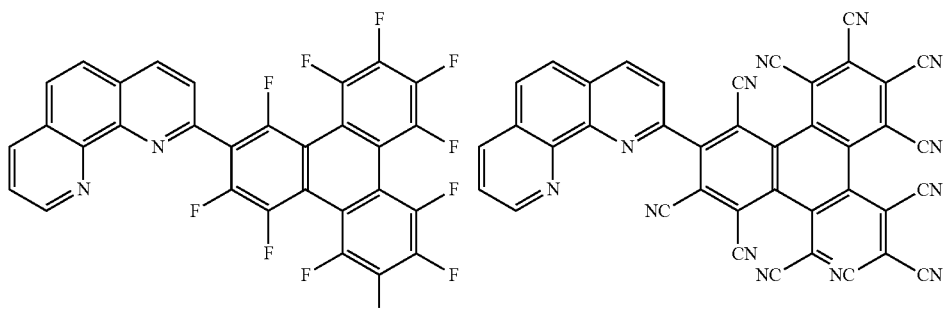
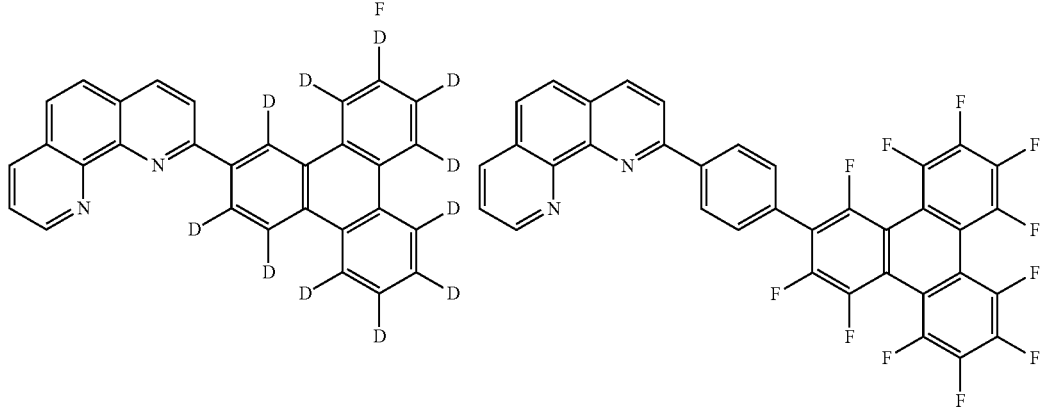
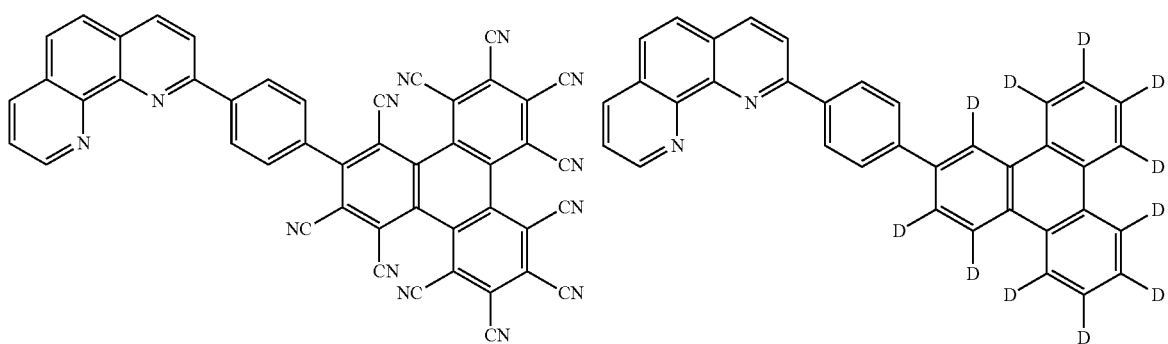

-continued
151
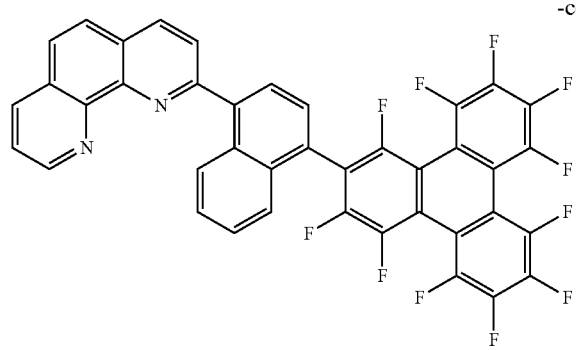
152
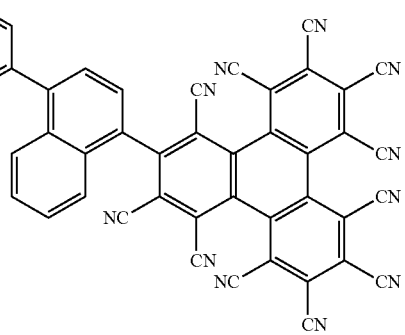
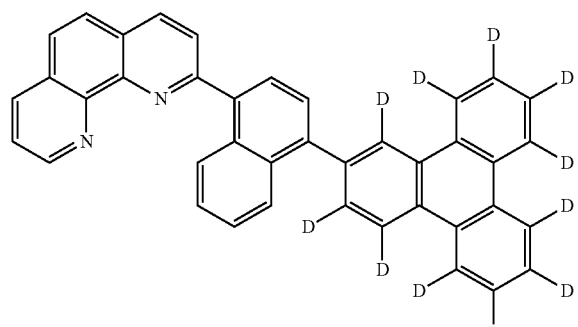
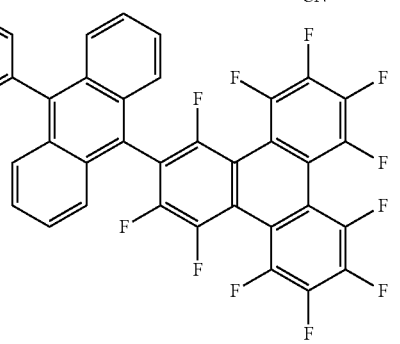
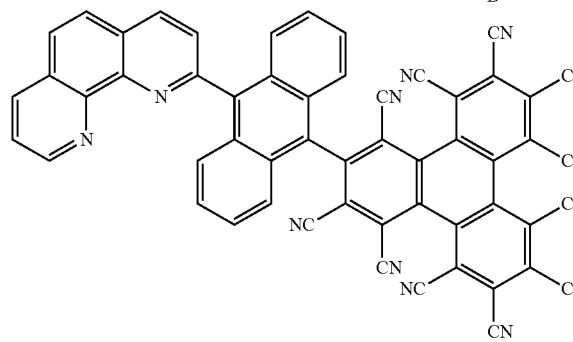
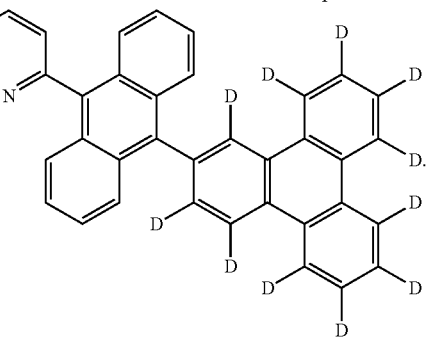
* * * * *